United States Patent
Suto et al.

(10) Patent No.: US 11,505,531 B2
(45) Date of Patent: Nov. 22, 2022

(54) PIPERAZINE-2,5-DIONES AS TGF-BETA INHIBITORS

(71) Applicants: SOUTHERN RESEARCH INSTITUTE, Birmingham, AL (US); UAB RESEARCH FOUNDATION, Birmingham, AL (US)

(72) Inventors: Mark J. Suto, Homewood, AL (US); Vandana V. Gupta, Birmingham, AL (US); Wei Zhang, Wilmington, MA (US); Joanne Murphy-Ullrich, Birmingham, AL (US)

(73) Assignees: UAB RESEARCH FOUNDATION, Birmingham, AL (US); SOUTHERN RESEARCH INSTITUTE, Birmingham, AL (US)

(*) Notice: Subject to any disclaimer, the term of this patent is extended or adjusted under 35 U.S.C. 154(b) by 0 days.

(21) Appl. No.: 17/265,357

(22) PCT Filed: Aug. 5, 2019

(86) PCT No.: PCT/US2019/045123
§ 371 (c)(1),
(2) Date: Feb. 2, 2021

(87) PCT Pub. No.: WO2020/033317
PCT Pub. Date: Feb. 13, 2020

(65) Prior Publication Data
US 2021/0323933 A1 Oct. 21, 2021

Related U.S. Application Data

(60) Provisional application No. 62/715,733, filed on Aug. 7, 2018.

(51) Int. Cl.
| | | |
|---|---|---|
| C07D 241/52 | (2006.01) |
| A61P 19/04 | (2006.01) |
| A61P 35/04 | (2006.01) |
| C07D 241/08 | (2006.01) |

(52) U.S. Cl.
CPC ............ *C07D 241/52* (2013.01); *A61P 19/04* (2018.01); *A61P 35/04* (2018.01); *C07D 241/08* (2013.01)

(58) Field of Classification Search
None
See application file for complete search history.

(56) References Cited

U.S. PATENT DOCUMENTS

2003/0207868 A1   11/2003   Orme et al.
2008/0242666 A1   10/2008   Leach et al.

FOREIGN PATENT DOCUMENTS

WO   PCT/US2019/045123   8/2019

OTHER PUBLICATIONS

Nguyen et al (Bioorg Med Chem Lett 19:3832-3835, 2009) (Year: 2009).*
CAS RN 160886-53-3 (entered into STN on Feb. 16, 1995) (Year: 1995).*
CAS RN 2166687-28-9 (entered into STN on Dec. 31, 2017) (Year: 2017).*
STN Accession No. 1995:285899, describing Blazickova et al (Int J Immunotherapy 10(3):89-93, 1994)) (Year: 1995).*
Yang et al. (2009) "Deficiency of thrombospondin-1 reduces Th17 differentiation and attenuates experimental autoimmune encephalomyelitis" *J Autoimmun* 32: 94-10.
Yehualaeshet et al. (1999) "Activation of rat alveolar macrophage-derived latent transforming growth factor beta-1 by plasmin requires interaction with thrombospondin-1 and its cell surface receptor, CD36" *Am J Pathol* 155:841-851.
Yehualaeshet et al. (2000) "A CD36 synthetic peptide inhibits bleomycin-induced pulmonary inflammation and connective tissue synthesis in the rat" *Am. J. Respir. Cell Mol. Biol.* 23: 204-12.
Yevdokimova et al. (2001) "Thrombospondin-1 is the key activator of TGF-beta1 in human mesangial cells exposed to high glucose" *J Am Soc Nephrol* 12:703-712.
Yoshida et al. (2014) "TGF-β/Smad signaling during hepatic fibro-carcinogenesis (review)" *Int J Oncol* 45:1363-1371.
Young and Murphy-Ullrich (2004) "Molecular interactions that confer latency to transforming growth factor-beta" *J Biol Chem* 279:38032-38039.
Zhou et al. (2004) "Thy-1 expression regulates the ability of rat lung fibroblasts to activate transforming growth factor-beta in response to fibrogenic stimuli" *Am J Pathol* 165:659-669.
Zhou et al. (2006) "Thrombospondin 1 mediates angiotensin II induction of TGF-beta activation by cardiac and renal cells under both high and low glucose conditions" *Biochem Biophys Res Commun* 339:633-641.
International Search Report and Written Opinion dated Feb. 13, 2020 by the International Search Authority for International Application No. PCT/US2019/045123, filed on Aug. 5, 2019, and published as WO 2020/033317 on May 7, 2020 (Applicant—Southern Research Institute, et al.) (14 pages).
Adams and Lawler (2004) "The thrombospondins" *Int J Biochem Cell Biol* 36:961-968.
Adams and Lawler (2011) "The thrombospondins" *Cold Spring Harb Perspect Biol* 3:a009712.
Agah et al. (2002) "The lack of thrombospondin-1 (TSP1) dictates the course of wound healing in double-TSP1/TSP2-null mice" *Am J Pathol* 161:831-839.

(Continued)

*Primary Examiner* — Craig D Ricci
(74) *Attorney, Agent, or Firm* — Ballard Spahr LLP

(57) ABSTRACT

The present disclosure is concerned with piperazine-2,5-diones that are capable of inhibiting TGF-β and methods of treating cancers such as, for example, multiple myeloma and a hematologic malignancy, and methods of treating fibrotic conditions using these compounds. This abstract is intended as a scanning tool for purposes of searching in the particular art and is not intended to be limiting of the present invention.

12 Claims, 7 Drawing Sheets

(56) References Cited

OTHER PUBLICATIONS

Belmadani et al. (2007) "A thrombospondin-1 antagonist of transforming growth factor-beta activation blocks cardiomyopathy in rats with diabetes and elevated angiotensin II" *Am J Pathol* 171:777-789.

Benzoubir et al. (2013) "HCV core-mediated activation of latent TGF-β via thrombospondin drives the crosstalk between hepatocytes and stromal environment" *J Hepatol* 59:1160-1168.

Breitkopf et al. (2005) "Thrombospondin 1 acts as a strong promoter of transforming growth factor beta effects via two distinct mechanisms in hepatic stellate cells" *Gut* 54:673-681.

Cauchard et al. (2004) "Activation of latent transforming growth factor beta 1 and inhibition of matrix metalloprotease activity by a thrombospondin-like tripeptide linked to elaidic acid" *Biochem Pharmacol* 67:2013-2022.

Chen et al. (2009) "A TSP-1 synthetic peptide inhibits bleomycin-induced lung fibrosis in mice" *Exp. Toxicol. Pathol.* 61: 59-65.

Chen et al. (2011) "Thrombospondin 1 is a key mediator of transforming growth factor β-mediated cell contractility in systemic sclerosis via a mitogen-activated protein kinase kinase (MEK)/extracellular signal-regulated kinase (ERK)-dependent mechanism" *Fibrogenesis Tissue Repair* 4:9.

Chipev et al. (2000) "Myofibroblast phenotype and apoptosis in keloid and palmar fibroblasts in vitro" *Cell Death Differ* 7:166-176.

Connolly et al. (2011) "Outgrowth of drug-resistant carcinomas expressing markers of tumor aggression after long-term TβRI/II kinase inhibition with LY2109761" *Cancer Res* 71:2339-2349.

Crawford et al. (1998) "Thrombospondin-1 is a major activator of TGF-beta1 in vivo" *Cell* 93:1159-1170.

Daniel et al. (2004) "Thrombospondin-1 is a major activator of TGF-beta in fibrotic renal disease in the rat in vivo" *Kidney Int* 65:459-468.

Daniel et al. (2007) "Thrombospondin-1 is an endogenous activator of TGF-beta in experimental diabetic nephropathy in vivo" *Diabetes* 56:2982-2989.

DiPietro et al. (1996) "Thrombospondin 1 synthesis and function in wound repair" *Am J Pathol* 148:1851-1860.

Dropmann et al. (2016) "TGF-β1 and TGF-β2 abundance in liver diseases of mice and men" *Oncotarget* 7:19499-19518.

El-Youssef (1999) "Increased expression of transforming growth factor-beta1 and thrombospondin-1 in congenital hepatic fibrosis: possible role of the hepatic stellate cell" *Journal of pediatric gastroenterology and nutrition* 28:386-392.

Fabregat et al. (2016) "TGF-β signalling and liver disease" *The FEBS journal* 283:2219-2232.

Hayashi et al. (2012) "Thrombospondin-1 is a novel negative regulator of liver regeneration after partial hepatectomy through transforming growth factor-beta1 activation in mice" *Hepatology* 55:1562-1573.

Hugo (2003) "The thrombospondin 1-TGF-beta axis in fibrotic renal disease" *Nephrol Dial Transplant* 18:1241-1245.

Katz et al. (2016) "TGF-β signaling in liver and gastrointestinal cancers" *Cancer letters* 379:166-172.

Kondou et al. (2003) "A blocking peptide for transforming growth factor-beta1 activation prevents hepatic fibrosis in vivo" *J Hepatol* 39:742-748.

Kuroki et al. (2015) "Effect of LSKL peptide on thrombospondin 1-mediated transforming growth factor β signal activation and liver regeneration after hepatectomy in an experimental model" *Br J Surg* 102:813-825.

Li et al. (2016) "Long Noncoding RNA EBLN3P Promotes the Progression of Liver Cancer via Alteration of microRNA-144-3p/DOCK4 Signal" *Hepatol Res*, doi: 10.1111/hepr.12787.

Lu et al. (2011) "Blockade of TSP1-dependent TGF-β activity reduces renal injury and proteinuria in a murine model of diabetic nephropathy" *Am J Pathol* 178:2573-2586.

Lu et al. (2016) "Inhibition of Transforming Growth Factor-β Activation Diminishes Tumor Progression and Osteolytic Bone Disease in Mouse Models of Multiple Myeloma" *Am J Pathol* 186:678-690.

Ludlow et al. (2005) "Characterization of integrin beta6 and thrombospondin-1 double-null mice" *J Cell Mol Med* 9:421-437.

Mimura et al. (2005) "Constitutive thrombospondin-1 overexpression contributes to autocrine transforming growth factor-beta signaling in cultured scleroderma fibroblasts" *Am J Pathol* 166:1451-1463.

Murphy-Ullrich and Mosher (1985) "Localization of thrombospondin in clots formed in situ" *Blood* 66:1098-1104.

Murphy-Ullrich and Poczatek (2000) "Activation of latent TGF-beta by thrombospondin-1: mechanisms and physiology" *Cytokine Growth Factor Rev* 11:59-69.

Myung et al. (2007) "Bile acid-mediated thrombospondin-1 induction in hepatocytes leads to transforming growth factor-beta-dependent hepatic stellate cell activation" *Biochem Biophys Res Commun* 353:1091-1096.

Narmada (2013) "HGF regulates the activation of TGF-β1 in rat hepatocytes and hepatic stellate cells" *J Cell Physiol* 228:393-401.

Nguyen, et al. (2009) "3-(aminomethyl)piperazine-2,5-dione as a novel NMDA glycine site inhibitor from the chemical universe database GDB" *Bioorganic & Medicinal Chemistry Letters*, 19: 3832-3835.

NIH Grant No. 1R01CA175012-01A.

Nor et al. (2005) "Activation of Latent TGF-β1 by Thrombospondin-1 is a Major Component of Wound Repair" *Oral Biosci Med* 2:153-161.

Poczatek et al. (2000) "Glucose stimulation of transforming growth factor-beta bioactivity in mesangial cells is mediated by thrombospondin-1" *Am J Pathol* 157:1353-136.

Pubmed Compound Summary for CID 101497257, (3S,6R)-3-(Aminomethyl)-6-methylpiperazine-2,5-dione, U.S. National Library of Medicine, Dec. 18, 2015, p. 1-11.

Pubmed Compound Summary for CID 18338633, 1-Benzyl-N-cyclohexyl-5,5,-dimethyl-3,6-dioxopiperazine-2-carboxamie, U.S. National Library of Medicine, Dec. 4, 2007, p. 1-17.

Prud'homme (2007) "Pathobiology of transforming growth factor beta in cancer, fibrosis and immunologic disease, and therapeutic considerations" *Lab Invest* 87:1077-1091.

Raugi et al. (1987) "Thrombospondin in early human wound tissue" *J Invest Dermatol* 89:551-554.

Reed et al. (1993) "Differential expression of SPARC and thrombospondin 1 in wound repair: immunolocalization and in situ hybridization" *J Histochem Cytochem* 41:1467-1477.

Sakai et al. (2003) "Thrombospondin-1 promotes fibroblast-mediated collagen gel contraction caused by activation of latent transforming growth factor beta-1" *J Dermatol Sci* 31:99-109.

Schultz-Cherry and Murphy-Ullrich (1993) "Thrombospondin causes activation of latent transforming growth factor-beta secreted by endothelial cells by a novel mechanism" *J Cell Biol* 122:923-932.

Smalling et al. (2013) "Genome-wide transcriptome analysis identifies novel gene signatures implicated in human chronic liver disease" *Am J Physiol Gastrointest Liver Physiol* 305:G364-374.

Sweetwyne and Murphy-Ullrich (2012) "Thrombospondin1 in tissue repair and fibrosis: TGF-β-dependent and independent mechanisms" *Matrix Biol* 31:178-186.

Wang et al. (2002) "Nitric oxide and cGMP-dependent protein kinase regulation of glucose-mediated thrombospondin 1-dependent transforming growth factor-beta activation in mesangial cells" *J Biol Chem* 277:9880-9888.

Wang et al. (2004) "Glucose up-regulates thrombospondin 1 gene transcription and transforming growth factor-beta activity through antagonism of cGMP-dependent protein kinase repression via upstream stimulatory factor 2" *J Biol Chem* 279:34311-34322.

Weiskirchen and Tacke (2016) "Liver Fibrosis: From Pathogenesis to Novel Therapies" *Dig Dis* 34:410-422.

Xu et al. (2016) "TGF-β/SMAD Pathway and Its Regulation in Hepatic Fibrosis" *J Histochem Cytochem* 64:157-167.

(56) References Cited

OTHER PUBLICATIONS

U.S. Appl. No. 62/715,733, filed Aug. 7, 2018, Mark J. Suto (Southern Research Institute, et al.).

* cited by examiner

PIPERAZINE-2,5-DIONES AS TGF-BETA INHIBITORS

CROSS-REFERENCE TO RELATED APPLICATION

This Application is a national stage filing under 35 U.S.C. § 371 of International Application No. PCT/US2019/045123, filed on Aug. 5, 2019, which claims the benefit of U.S. Application No. 62/715,733, filed on Aug. 7, 2018, the contents of which are incorporated herein by reference in their entireties.

STATEMENT REGARDING FEDERALLY SPONSORED RESEARCH

This invention was made with government support under grant number 1R01CA175012-01A awarded by the National Institutes of Health. The government has certain rights in the invention.

BACKGROUND

TGF-β is a central regulator of chronic liver disease through induction of fibrogenic responses (Weiskirchen and Tacke (2016) *Dig Dis* 34:410-422; Katz et al. (2016) *Cancer letters* 379:166-172; Yoshida et al. (2014) *Int J Oncol* 45:1363-1371; Fabregat et al. (2016) *The FEBS journal* 283:2219-2232; Xu et al. (2016) *J Histochem Cytochem* 64:157-167). Although infiltrating macrophages are a source of TGF-β, hepatic stellate cells are a significant source of TGF-β in liver fibrosis. TGF-β stimulates induction of myofibroblast-like properties of hepatic stellate cells to produce extracellular matrix, leading to fibrosis. Although TGF-β inhibits hepatocyte proliferation under basal conditions, it has pro-oncogenic properties during malignant progression through stimulating epithelial to mesenchymal transition, cell survival and migration, and reduced immune surveillance.

TSP1 expression is increased in human liver disease with the THBS1 gene identified as part of the characteristic gene signature of chronic liver disease, including cirrhosis, in humans (Smalling et al. (2013) *Am J Physiol Gastrointest Liver Physiol* 305:G364-374). In vitro studies show that bile acids increase expression of TSP1 by hepatocytes, resulting in increased TGF-β signaling in co-cultured hepatic stellate cells (Myung et al. (2007) *Biochem Biophys Res Commun* 353:1091-1096). Both TSP1 and TGF-β are increased in congenital hepatic fibrosis (El-Youssef (1999) *Journal of pediatric gastroenterology and nutrition* 28:386-392). TSP1 regulated TGF-β activation prevented hepatocyte proliferation and liver regeneration after partial hepatectomy in Thbs1 deficient mice (Hayashi et al. (2012) *Hepatology* 55:1562-1573) and TSP1 induction by obstructed portal flow in mice is thought to lead to TGF-β-dependent liver atrophy (Hayashi et al. (2016) *Hepatol Res* 55: 1562-1573). TSP1 has been shown to regulate latent TGF-β activation in animal models of liver fibrosis and in cell culture models (reviewed in Li et al. (2016) *Hepatol Res*, doi: 10.1111/hepr.1287). Treatment of rats with the TSP1 antagonist peptide LSKL prevented TGF-β activation and reduced liver fibrosis in the dimethylnitrosamine model (Kondou et al. (2003) *J Hepatol* 39:742-748). TSP1 is required for TGF-β signaling in both cultured hepatocytes and hepatic stellate cells, which is blocked by LSKL peptide (Breitkopf et al. (2005) *Gut* 54:673-681; Narmada (2013) *J Cell Physiol* 228:393-401). Interestingly, TSP1-dependent latent TGF-β activation might play a role in hepatitis C induced fibrosis and carcinogenesis as the hepatitis C core protein induces TSP1 expression by hepatocytes to increase active TGF-β and LSKL peptide blocks hepatitis C core protein activation of TGF-β (Benzoubir et al. (2013) *J Hepatol* 59:1160-1168). LSKL peptide administered early after injury also accelerated liver regeneration in mice following partial hepatectomy through blocking TGF-β activation and signaling (Kuroki et al. (2015) *Br J Surg* 102:813-825). Both the TGF-β1 and the TGF-β2 isoforms are upregulated in mouse models and in human tissues with liver fibrosis and also hepatocellular carcinoma (Dropmann et al. (2016) *Oncotarget* 7:19499-19518): this is interesting since TSP1 can activate both the β1 and β2 isoforms of latent TGF-β, whereas β2 cannot be activated by integrin-dependent mechanisms.

Genetic ablation of TGF-β, its receptors, or its signaling mediators results in developmental defects, inflammation, and increased carcinomas. Thus, it is therapeutically advantageous to target only adverse TGF-β activity in liver disease and spare homeostatic activity. Current anti-TGF-β therapeutics target the molecule itself or downstream signaling pathways and provide no mechanism for distinguishing between homeostatic and disease-related TGF-β activity, thereby increasing the potential for adverse effects. In fact, Smad 2 resistance and increased papilloma incidence in mice treated for 20 weeks with a TGF-β receptor kinase inhibitor have been identified (Connolly et al. (2011) *Cancer Res* 71:2339-2349) and the 1D11 pan-specific anti-TGF-β neutralizing antibody shows epithelial hyperplasia and progression to carcinoma in some models (Prud'homme (2007) *Lab Invest* 87:1077-1091).

TGF-β is secreted as a biologically inactive growth factor and control of the conversion of latent TGF-β to a biologically active growth factor is a major regulatory node. Binding of the N-terminal latency associated peptide (LAP) prevents TGF-β binding to its receptors and this interaction must be disrupted for TGF-β signaling to occur. Latent TGF-β can be converted to the active form through multiple mechanisms that include proteolysis, binding to integrins, mechanical forces, modifications of the latent complex by viral enzymes or by reactive oxygen species, or by binding to the secreted and ECM protein TSP1 (Sweetwyne and Murphy-Ullrich (2012)*Matrix Biol* 31:178-186; Murphy-Ullrich and Poczatek (2000) *Cytokine Growth Factor Rev* 11:59-69). The mechanism that regulates latent TGF-β activation can vary with tissue, cell type, and specific disease milieu. Blockade of the major activation mechanism in a particular disease typically attenuates adverse effects of TGF-β. Thus, it is important to identify the predominant mechanism of TGF-β activation in multiple myeloma.

Thrombospondin 1 (TSP1) is a complex multi-functional protein released from platelet α-granules, incorporated into the fibrin clot, and expressed by cell types that participate in wound healing responses in a temporally regulated manner (Agah et al. (2002) *Am J Pathol* 161:831-839; Murphy-Ullrich and Mosher (1985) *Blood* 66:1098-1104; DiPietro et al. (1996) *Am J Pathol* 148:1851-1860; Reed et al. (1993) *J Histochem Cytochem* 41:1467-1477; Raugi et al. (1987) *J Invest Dermatol* 89:551-554). TSP1 regulates multiple cellular events involved in tissue repair including hemostasis, cell adhesion, migration, proliferation, ECM expression and organization, and regulation of growth factor activity (Adams and Lawler (2004) *Int J Biochem Cell Biol* 36:961-968; Adams and Lawler (2011) *Cold Spring Harb Perspect Biol* 3:a009712). In addition to physiologic repair, TSP1 is also expressed at elevated levels in many tissues undergoing fibro-proliferative remodeling and blockade of specific actions of TSP1 or loss of TSP1 expression can attenuate pathologic tissue remodeling (Hugo (2003) *Nephrol Dial Transplant* 18:1241-1245; Poczatek et al. (2000) *Am J Pathol* 157:1353-1363; Daniel et al. (2007) *Diabetes* 56:2982-2989). TSP1 is a major regulator of latent TGF-β activation (Murphy-Ullrich and Poczatek (2000) *Cytokine Growth Factor Rev* 11:59-69). TSP1 also has TGF-β-independent functions in hemostasis, cell adhesion, migration, and growth factor regulation, e.g. regulation of epidermal growth factor (EGF), VEGF, and fibroblast growth factor (FGF) (Adams and Lawler (2011) *Cold Spring Harb Perspect Biol* 3:a009712). TSP1 is an endogenous angiogenesis inhibitor via inhibition of VEGF and FGF signaling. TSP1 binding to Cluster of Differentiation 47 (CD47) and Cluster of Differentiation 36 (CD36) blocks nitric oxide signaling.

TSP1 is a secreted ECM protein that controls TGF-β activity by binding and activating latent TGF-β (Sweetwyne and Murphy-Ullrich (2012) *Matrix Biol* 31:178-186; Murphy-Ullrich and Poczatek (2000) *Cytokine Growth Factor Rev* 11:59-69). TSP1 binds to latent TGF-β to activate TGF-β at the cell surface or in the extracellular milieu (Sweetwyne and Murphy-Ullrich (2012) *Matrix Biol* 31:178-186). Activation occurs through binding of the KRFK (-lysine-arginine-phenylalanine-lysine-) sequence in the TSP1 type 1 repeats (TSRs) to LSKL (-leucine-serine-lysine-leucine-) in the LAP of the latent complex, which disrupts LAP-mature domain interactions to expose the receptor binding sequences on the mature domain, rendering TGF-β capable of signaling (Young and Murphy-Ullrich (2004) *J Biol Chem* 279:38032-38039). Peptide mimetics of sequences involved in TSP1-TGF-β binding competitively inhibit TSP1-TGF-β activation and studies with these peptides have established TSP1 as a primary regulator of TGF-β bioactivity in different diseases (Sweetwyne and Murphy-Ullrich (2012)*Matrix Biol* 31:178-186). The tetrapeptide LSKL, which competitively blocks TSP-LAP binding, has been used in rodent models to inhibit TSP1-TGF-β activation and attenuate disease. Dose dependent intraperitoneal injection (i.p.) of LSKL improves end organ function in murine diabetic nephropathy and rat cardiomyopathy by blocking TGF-β signaling in target tissues (Belmadani et al. (2007) *Am J Pathol* 171:777-789; Lu et al. (2011) *Am J Pathol* 178:2573-2586). Animals necropsied after 15 weeks of treatment with 30 mg/kg i.p. LSKL, 3 times weekly, showed no inflammation, no tumors in all major organs, and no impairment of wound healing (Lu et al. (2011) *Am J Pathol* 178:2573-2586).

In vitro studies have shown that TSP1 activates latent TGF-β secreted by multiple cell types including endothelial cells, mesangial cells, hepatic stellate cells and skin, lung, and cardiac fibroblasts, T cells, and macrophages (Breitkopf et al. (2005) *Gut* 54:673-681; Murphy-Ullrich and Poczatek (2000) *Cytokine Growth Factor Rev* 11:59-69; et al. (2000) *Am J Pathol* 157:1353-1363; Mimura et al. (2005) *Am J Pathol* 166:1451-1463; Yehualaeshet et al. (1999) *Am J Pathol* 155:841-851; Zhou et al. (2006) *Biochem Biophys Res Commun* 339:633-641; Schultz-Cherry and Murphy-Ullrich (1993) *J Cell Biol* 122:923-932; Yevdokimova et al. (2001) *J Am Soc Nephrol* 12:703-712; Yang et al. (2009) *J Autoimmun* 32: 94-103; Zhou et al. (2004) *Am J Pathol* 165:659-669). Peptides such as LSKL or WxxW which block TSP1 binding to the latent complex or antibodies which block TSP1-dependent TGF-β activation such as monoclonal antibody 133 (Mab 133) have been used to establish the involvement of endogenous TSP1 in TGF-β activation in a number of disease conditions and physiologic processes (Belmadani et al. (2007) *Am J Pathol* 171:777-789; Lu et al. (2011) *Am J Pathol* 178:2573-2586; Crawford et al. (1998) *Cell* 93:1159-1170; Daniel et al. (2004) *Kidney Int* 65:459-468; Kondou et al. (2003) *J Hepatol* 39:742-748).

Initial evidence for an in vivo role of TSP1 in latent TGF-β activation was shown by the ability of the KRFK peptide administered in the perinatal period to partially rescue the abnormal TSP-1 null phenotype, in particular airway epithelial hyperplasia and pancreatic islet hyperplasia/acinar hypoplasia (Crawford et al. (1998) *Cell* 93:1159-1170). Furthermore, treatment of wild type mice with the LSKL blocking peptide in the perinatal period replicated features of the TSP1 knockout phenotype in the airways and pancreas. Double knockout of both $\beta_6$ integrin and TSP1 results in a phenotype distinct from either single knockout that is characterized by severe inflammation, cardiac degeneration, and epithelial hyperplasia, suggesting both separate and synergistic roles in regulating latent TGF-β activation (Ludlow et al. (2005) *J Cell Mol Med* 9:421-437). However, it is likely that the primary role for TSP1 in controlling TGF-β activation is during injury, under stress, and in pathologic conditions, rather than during development. The expression of TSP1 is induced by factors associated with systemic diseases with fibrotic end organ involvement including high glucose, reactive oxygen species, and angiotensin II (Zhou et al. (2006) *Biochem Biophys Res Commun* 339:633-641; Yevdokimova et al. (2001) *J Am Soc Nephrol* 12:703-712; Wang et al. (2002) *J Biol Chem* 277:9880-9888; Wang et al. (2004) *J Biol Chem* 279:34311-34322). Indeed there is evidence from studies utilizing TSP1 antagonist peptides and diabetic TSP1 knockout mice that TSP1 is a major factor in the development of fibrotic end organ complications in diabetes (Daniel et al. (2007) *Diabetes* 56:2982-2989; Belmadani et al. (2007) *Am J Pathol* 171: 777-789; Lu et al. (2011) *Am J Pathol* 178:2573-2586). Treatment with i.p. injections of LSKL, but not LSAL (leucine-serine-alanine-leucine) control peptide, reduced cardiac fibrosis, Smad phosphorylation, and improved left ventricular function (Belmadani et al. (2007) *Am J Pathol* 171:777-789). Similarly, treatment of Akita mice, a model of type 1 diabetes, with i.p. LSKL reduced urinary TGF-β activity and renal phospho-Smad 2/3 levels and improved markers of tubulointerstitial injury and podocyte function. (Lu et al. (2011) *Am J Pathol* 178:2573-2586). Interestingly, several studies have shown that TSP1 is involved in alveolar macrophage-dependent TGF-β activation in mouse and rat models of bleomycin-induced pulmonary fibrosis and treatment with either TSP1 or CD36 antagonist peptides can ameliorate lung fibrosis and reduce active TGF-β (Chen et al. (2009) *Exp. Toxicol. Pathol.* 61: 59-65; Yehualaeshet et al. (2000) *Am. J. Respir. Cell Mol. Biol.* 23: 204-12).

One of the roles of TSP1 in dermal wound healing appears to be regulating the activation of latent TGF-β. The phenotype of excisional wound healing in the TSP1 null mouse is consistent with a decrease in local TGF-β activation (Agah et al. (2002) *Am J Pathol* 161:831-839) and is characterized by a delay in macrophage recruitment and capillary angiogenesis and a persistence of granulation tissue, neovascularization, and inflammation (Nor et al. (2005) *Oral Biosci Med* 2:153-161). Topical treatment of TSP1 null wounds with the KRFK activating peptide largely rescued the TSP1 null wound phenotype (Nor et al. (2005) *Oral Biosci Med* 2:153-161). TGF-β levels in these wounds were increased following KRFK treatment and the effects of the KRFK peptide were blocked by a pan-specific anti-TGF-β antibody. While these data suggest that TSP1 plays a role in local activation of TGF-β during wounding, the studies of Agah et al., concluded that the decreased active and total TGF-β in the wounds of TSP1 or TSP1/TSP2 null mice is indirect and primarily due to defects in macrophage recruitment to wounds (a major source of TGF-β in wounds) leading to an overall reduction in TGF-β rather than a defect in activation (Agah et al. (2002) *Am J Pathol* 161:831-839). Despite this controversy, it is clear that TSP1 has the potential to modify the wound healing process. Subcutaneous implantation of TSP1 soaked sponges increased levels of active TGF-β, gel contraction and fibroblast migration (Sakai et al. (2003) *J Dermatol Sci* 31:99-109). Overexpression of TSP1 in keloids and in scleroderma correlates with increased TGF-β activity (Mimura et al. (2005) *Am J Pathol* 166:1451-1463; et al. (2000) *Cell Death Differ* 7:166-176; Chen et al. (2011) *Fibrogenesis Tissue Repair* 4:9). Others have used a derivative of the KRFK sequence, KFK (lysine-phenylalanine-lysine) coupled to a fatty acyl moiety to locally activate TGF-β and increase TIMP-1, which reduces MMP-induced elastin and collagen degradation when applied to dermal fibroblast cultures (Cauchard et al. (2004) *Biochem Pharmacol* 67:2013-2022). Systemic administration of the LSKL blocking peptide did not reduce Smad signaling or impair dermal wound healing in diabetic mice, although, these studies did not address the effects of direct LSKL administration to the wounds and it is not known if local dermal levels of LSKL following systemic intraperitoneal peptide administration are sufficient to alter local TGF-β activation (Lu et al. (2011) *Am J Pathol* 178:2573-2586).

Although peptides comprising the amino acid sequence LSKL capable of stimulating TGF-β activity are known, these peptides are often costly and difficult to synthesize. Moreover, small molecules such as LSKL have an extremely short plasma stability half-life, only 2.1 minutes. Thus, there remains a need for small molecules capable of altering TGF-β activity that are less expensive, easier to synthesize, and have an extended plasma stability half-life and methods of making and using same.

SUMMARY

In accordance with the purpose(s) of the invention, as embodied and broadly described herein, the invention, in one aspect, relates to piperazine-2,5-diones compounds useful in the treatment of disorders associated with a dysregulation of TGF-β including, but not limited to, cancers, immune dysfunction, and fibrotic conditions.

Disclosed are compounds having a structure represented by a formula:

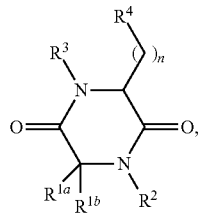

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —NR$^{20a}$R$^{20b}$ and Cy$^1$; wherein each of $R^{20a}$ and $R^{20b}$, when present, is independently selected from hydrogen, C1-C4 alkyl, C1-C4 haloalkyl, cycloalkyl, and heteroaryl; wherein Cy$^1$, when present, is selected from C5-C6 cycloalkyl, monocyclic heteroaryl, and —C$_6$H$_4$R$^{21}$ and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein R$^{21}$, when present, is selected from —(CH$_2$)$_q$NR$^{31a}$R$^{31b}$ and —C(O) NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$, or wherein R$^{1a}$ is hydrogen, R$^{1b}$ is —CH$_2$Cy$^2$, and R$^4$ is —C$_6$H$_4$R$^{21}$; wherein Cy$^2$ is selected from C3-C6 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; provided that when n is 1 and each of R$^{1a}$ and R$^{1b}$ together comprise a 3-membered cycloalkyl then Cy$^1$, when present, is not monocyclic heteroaryl, and provided that when R$^4$ is —NR$^{20a}$R$^{20b}$ then each of R$^{1a}$ and R$^{1b}$ is independently C1-C4 alkyl, or a pharmaceutically acceptable salt thereof.

Also disclosed are pharmaceutical compositions comprising a therapeutically effective amount of at least one disclosed compound and a pharmaceutically acceptable carrier.

Also disclosed are methods for inhibiting TGF-β activity in a subject, the method comprising the step of administering to the subject an effective amount of at least one compound having a structure represented by a formula:

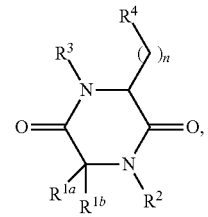

wherein n is selected from 1, 2, 3, and 4; wherein each of R$^{1a}$ and R$^{1b}$ is independently C1-C4 alkyl; or wherein each of R$^{1a}$ and R$^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of R$^2$ and R$^3$ is independently selected from hydrogen and C1-C4 alkyl; and wherein R$^4$ is selected from —NHR$^{20}$ and Cy$^1$; wherein R$^{20}$, when present, is selected from hydrogen and C1-C4 alkyl; wherein Cy$^1$, when present, is selected from C5-C6 cycloalkyl, monocyclic heteroaryl, and —C$_6$H$_4$R$^{21}$ and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein R$^{21}$, when present, is selected from —(CH$_2$)$_q$NR$^{31a}$R$^{31b}$ and —C(O)NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$; or wherein R$^{1a}$ is hydrogen, R$^{1b}$ is —CH$_2$Cy$^3$ and R$^4$ is —C$_6$H$_4$R$^{21}$; wherein Cy$^3$ is selected from C3-C6 cycloalkyl, monocyclic heteroaryl, and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof, thereby inhibiting TGF-β activity in the subject.

Also disclosed are methods for inhibiting TGF-β activity in a subject, the method comprising the step of administering to the subject an effective amount of at least one compound having a structure selected from:

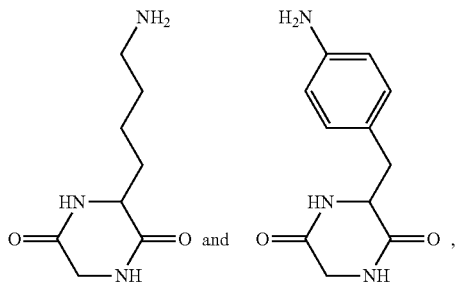 [SMILES: NCCCCC1NC(=O)CNC1=O ; Nc1ccc(CC2NC(=O)CNC2=O)cc1]

or a pharmaceutically acceptable salt thereof, thereby inhibiting TGF-β activity in the subject.

Also disclosed are methods for inhibiting TGF-β activity in at least one cell, the method comprising the step of contacting the cell with an effective amount of at least one compound having a structure represented by a formula:

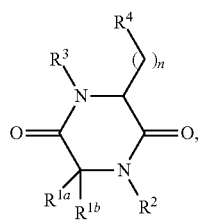

wherein n is selected from 1, 2, 3, and 4; wherein each of R$^{1a}$ and R$^{1b}$ is independently C1-C4 alkyl; or wherein each of R$^{1a}$ and R$^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of R$^2$ and R$^3$ is independently selected from hydrogen and C1-C4 alkyl; and wherein R$^4$ is selected from —NHR$^{20}$ and Cy$^1$; wherein R$^{20}$, when present, is selected from hydrogen and C1-C4 alkyl; wherein Cy$^1$, when present, is selected from C5-C6 cycloalkyl, monocyclic heteroaryl, and —C$_6$H$_4$R$^{21}$ and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein R$^{21}$, when present, is selected from —(CH$_2$)$_q$NR$^{31a}$R$^{31b}$ and —C(O)NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$, or wherein R$^{1a}$ is hydrogen, R$^{1b}$ is —CH$_2$Cy$^3$ and R$^4$ is —C$_6$H$_4$R$^{21}$; wherein Cy$^3$ is selected from C3-C6 cycloalkyl, monocyclic heteroaryl, and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof, thereby TGF-β activity in the cell.

Also disclosed are methods for inhibiting TGF-β activity in at least one cell, the method comprising the step of contacting the cell with an effective amount of at least one compound selected from:

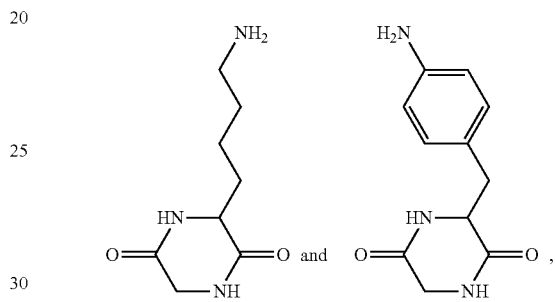

or a pharmaceutically acceptable salt thereof, thereby TGF-β activity in the cell.

Also disclosed are kits comprising at least one disclosed compound and one or more of: (a) at least one agent known to increase TGF-β activity; (b) at least one agent known to treat cancer; (c) at least one agent known to treat a fibrotic disorder; (d) at least one agent known to treat an immune dysfunction; (e) instructions for treating a disorder associated with TGF-β dysfunction; (f) instructions for treating cancer; (g) instructions for treating a fibrotic disorder; and (h) instructions for treating an immune dysfunction.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

Figure 1A:
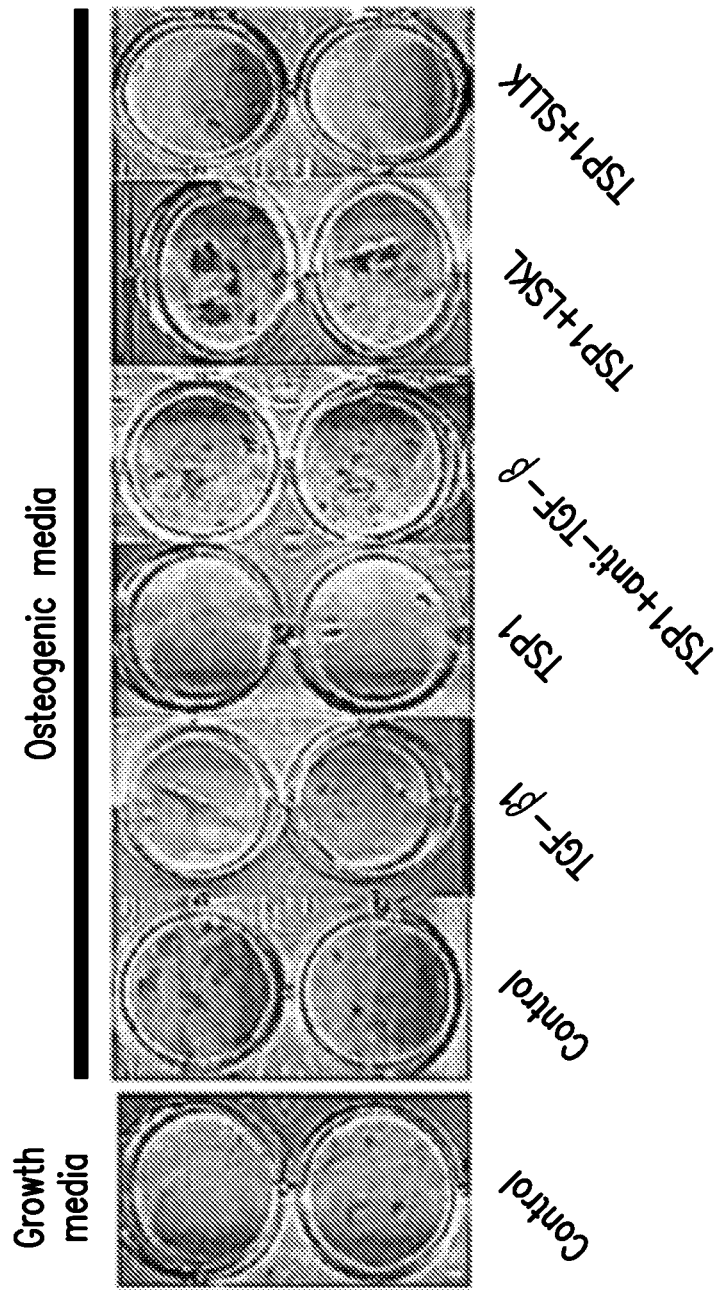
FIG. 1A and FIG. 1B show representative data illustrating the impact of TSP1, LSKL and TGF-β on osteoblast differentiation by MSCs under osteogenic conditions.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a viral infection. The term "patient" includes human and veterinary subjects. In some aspects of the disclosed methods, the subject has been diagnosed with a need for treatment of one or more viral infections prior to the administering step. In various aspects, the one or more disorders is selected from chikungunya, Venezuelan equine encephalitis, dengue, influenza, and zika.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzene-sulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A$^1$C(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula -SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$ N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C1-4 straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)O$_2$R●, -(haloR●), —(CH$_2$)$_{0-2}$OH, —(CH$_2$)$_{0-2}$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

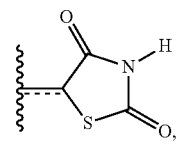

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thiohaloal-kyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

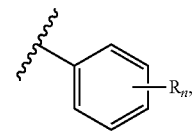

which is understood to be equivalent to a formula:

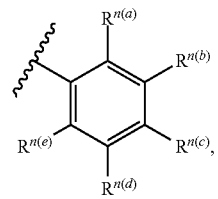

wherein n is typically an integer. That is, $R^n$ is understood to represent five independent substituents, $R^{n(a)}$, $R^{n(b)}$, $R^{n(e)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

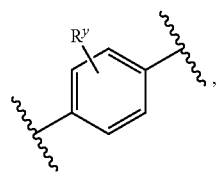

wherein $R^y$ represents, for example, 0-2 independent substituents selected from $A^1$, $A^2$, and $A^3$, which is understood to be equivalent to the groups of formulae:

wherein $R^y$ represents 0 independent substituents

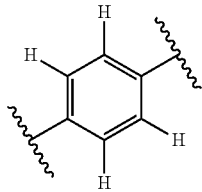

wherein $R^y$ represents 1 independent substituent

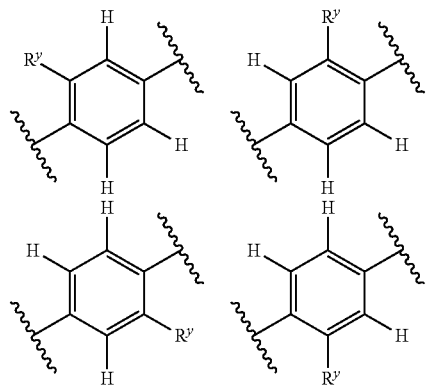

wherein $R^y$ represents 2 independent substituents

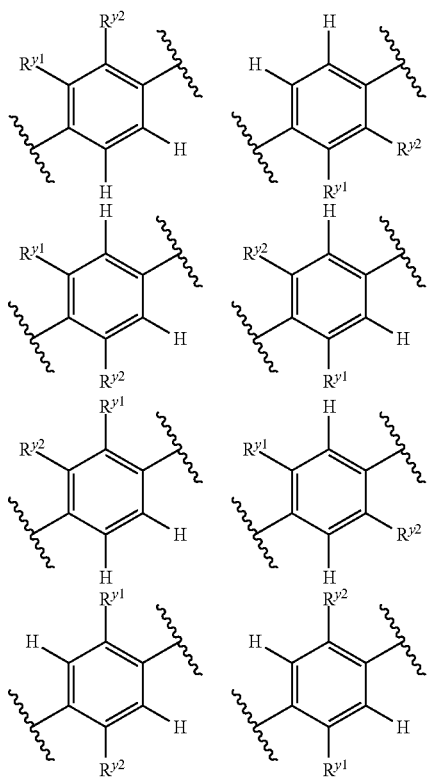

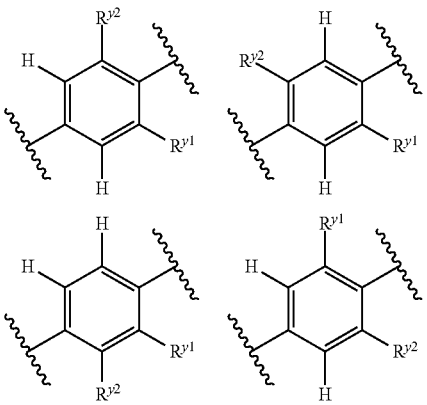

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

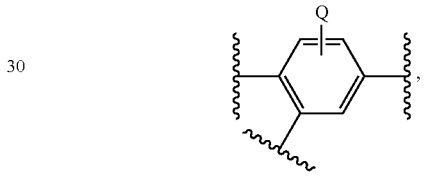

wherein, for example, Q comprises three substituents independently selected from hydrogen and A, which is understood to be equivalent to a formula:

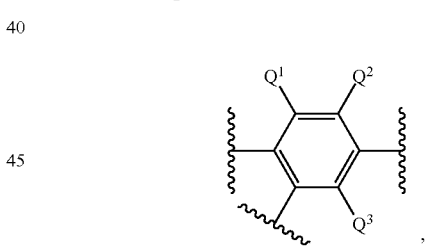

Again, by "independent substituents," it is meant that each Q substituent is independently defined as hydrogen or A, which is understood to be equivalent to the groups of formulae:

wherein Q comprises three substituents independently selected from H and A

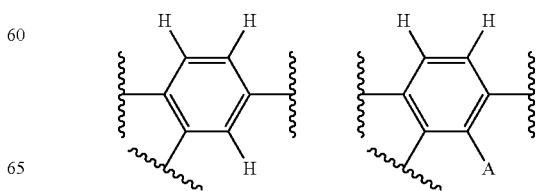

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are compounds useful in treating disorders associated with dysregulation of TGF-β, in particular, cancers, immune dysfunction, and fibrotic conditions.

In one aspect, the disclosed compounds exhibit inhibition of TGF-β.

In one aspect, the disclosed compounds are useful in inhibiting TGF-β in a mammal. In a further aspect, the disclosed compounds are useful in inhibiting TGF-β activity in at least one cell.

In one aspect, the disclosed compounds are useful in the treatment of cancers, as further described herein.

In one aspect, the disclosed compounds are useful in the treatment of fibrotic conditions, as further described herein.

In one aspect, the disclosed compounds are useful in the treatment of immune dysfunction, as described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

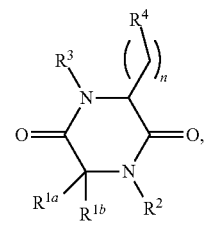

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from $—NR^{20a}R^{20b}$ and $Cy^1$; wherein each of $R^{20a}$ and $R^{20b}$, when present, is independently selected from hydrogen, C1-C4 alkyl, C1-C4 haloalkyl, cycloalkyl, and heteroaryl; wherein $Cy^1$, when present, is selected from C5-C6 cycloalkyl, monocyclic heteroaryl, and $—C_6H_4R^{21}$ and is substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from $—(CH_2)_qNR^{31a}R^{31b}$ and $—C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is $—C_6H_4C(O)NR^{32a}R^{32b}$, or wherein $R^{1a}$ is hydrogen, $R^{1b}$ is $—CH_2Cy^2$, and $R^4$ is $—C_6H_4R^{21}$; wherein $Cy^2$ is selected from C3-C6 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; provided that when n is 1 and each of $R^{1a}$ and $R^{1b}$ together comprise a 3-membered cycloalkyl then $Cy^1$, when present, is not monocyclic heteroaryl, and provided that when $R^4$ is $—NR^{20a}R^{20b}$ then each of $R^{1a}$ and $R^{1b}$ is independently C1-C4 alkyl, or a pharmaceutically acceptable salt thereof.

In one aspect, disclosed are compounds having a structure represented by a formula:

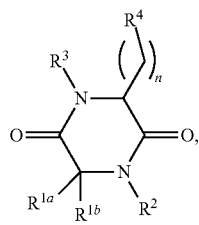

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from $—NR^{20a}R^{20b}$ and $Cy^1$; wherein each of $R^{20a}$ and $R^{20b}$, when present, is independently selected from hydrogen, C1-C4 alkyl, C1-C4 haloalkyl, cycloalkyl, and heteroaryl; wherein $Cy^1$, when present, is selected from C5-C6 cycloalkyl, monocyclic heteroaryl, and $—C_6H_4R^{21}$ and is substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from $—(CH_2)_qNR^{31a}R^{31b}$ and $—C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is $—C_6H_4C(O)NR^{32a}R^{32b}$, provided that when n is 1 and each of $R^{1a}$ and $R^{1b}$ together comprise a 3-membered cycloalkyl then $Cy^1$, when present, is not monocyclic heteroaryl, and provided that when $R^4$ is $—NR^{20a}R^{20b}$ then each of $R^{1a}$ and $R^{1b}$ is independently C1-C4 alkyl, or a pharmaceutically acceptable salt thereof.

In a further aspect, the compound has a structure represented by a formula selected from:

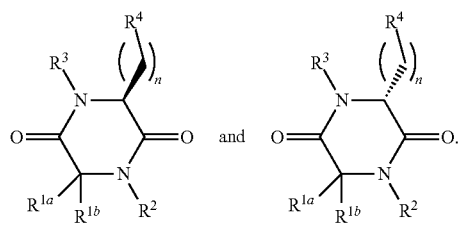

In a further aspect, the compound has a structure represented by a formula:

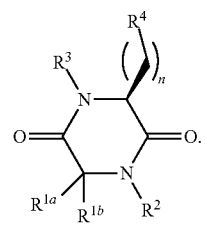

In a further aspect, the compound has a structure represented by a formula:

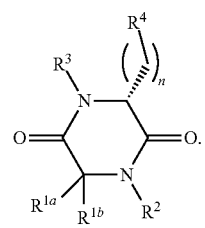

In a further aspect, the compound has a structure represented by a formula selected from:

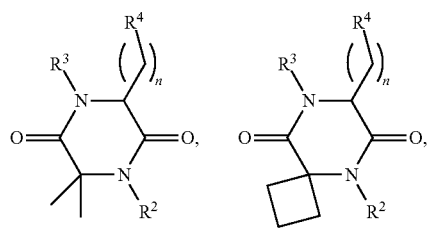

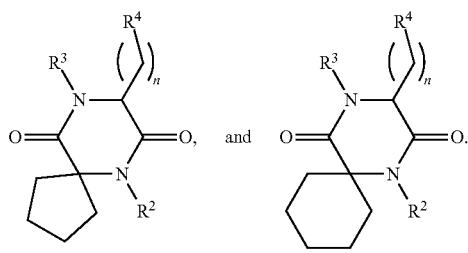

In a further aspect, the compound has a structure represented by a formula:

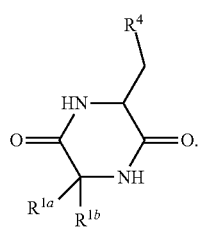

In a further aspect, a structure represented by a formula:

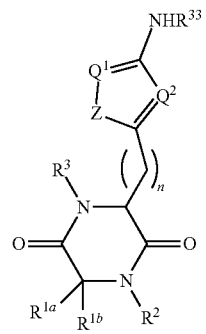

wherein Z is selected from O, S, and NR$^{40}$; wherein R$^{40}$, when present, is selected from hydrogen and C1-C4 alkyl; wherein each of Q$^1$ and Q$^2$ is independently selected from CH and N; and wherein R$^{33}$ is selected from hydrogen and C1-C4 alkyl.

In a further aspect, the compound has a structure represented by a formula:

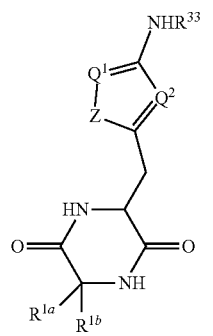

In a further aspect, the compound has a structure represented by a formula selected from:

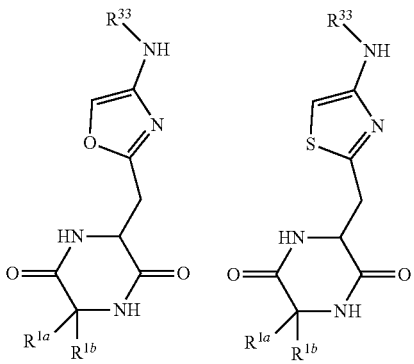

In a further aspect, the compound has a structure represented by a formula:

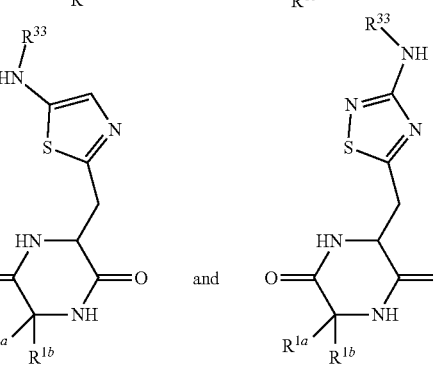

In a further aspect, the compound has a structure represented by a formula:

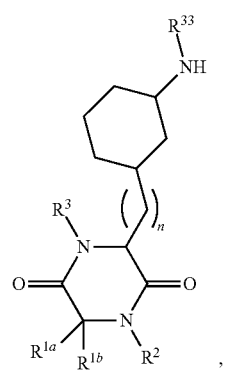

wherein R$^{33}$ is selected from hydrogen and C1-C4 alkyl.

In a further aspect, the compound has a structure represented by a formula:

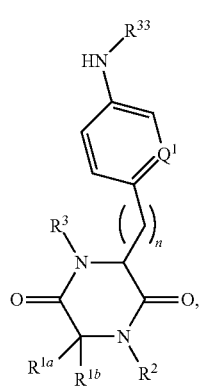

wherein $Q^1$ and $Q^2$ is independently selected from CH and N; and wherein $R^{33}$ is selected from hydrogen and C1-C4 alkyl.
In a further aspect, the compound has a structure selected from:
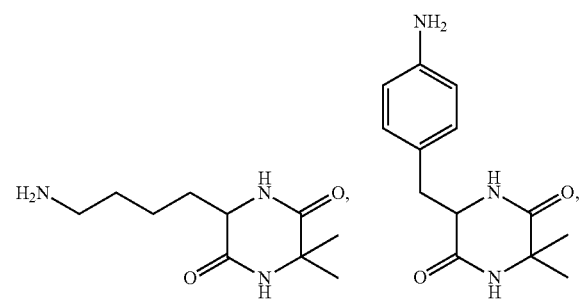
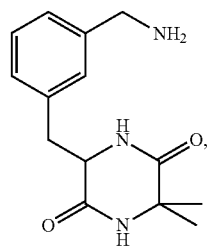
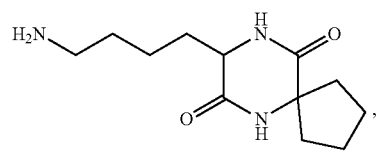
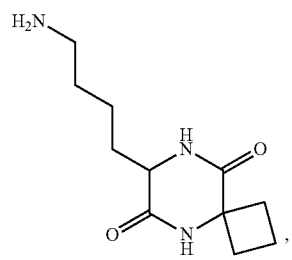
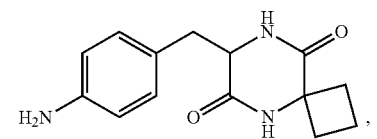
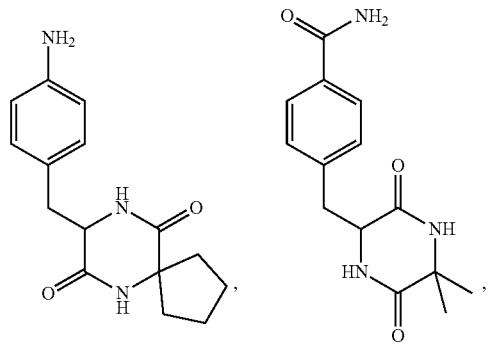
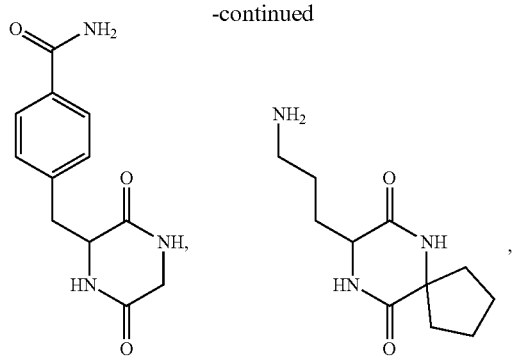
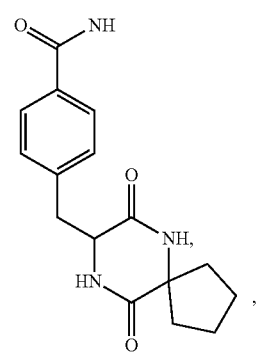
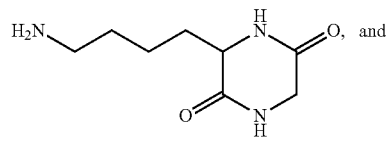
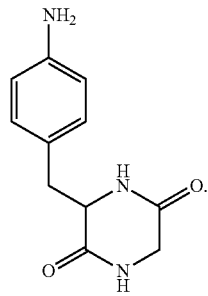
In a further aspect, the compound has a structure selected from:
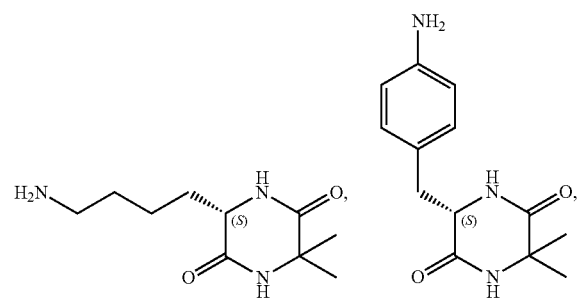

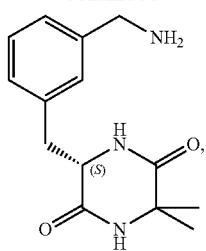
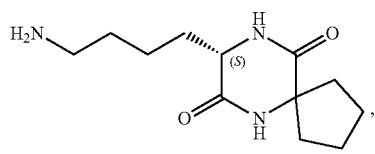
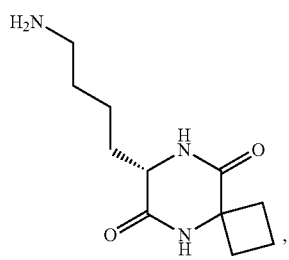
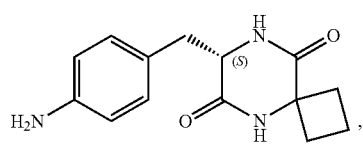
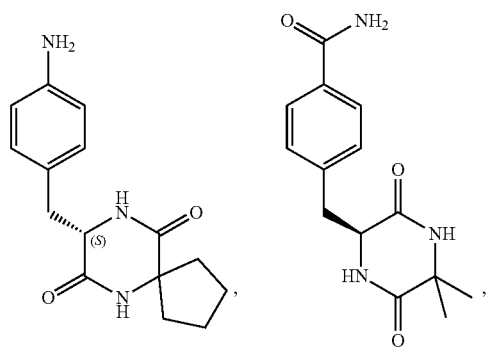
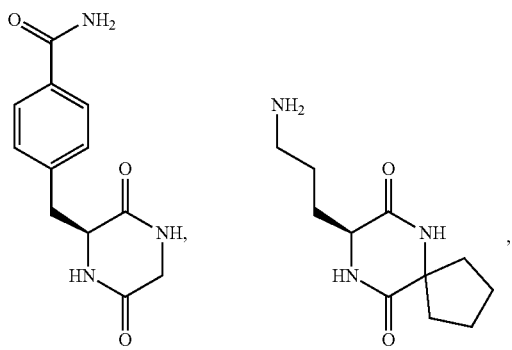

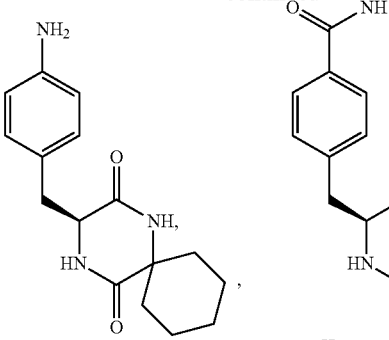
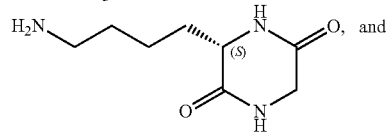
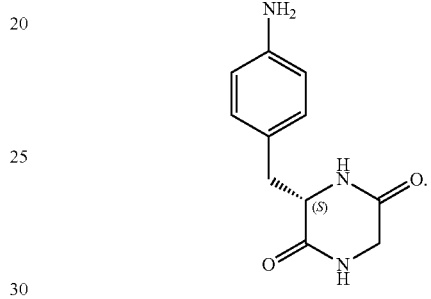

In one aspect, n is selected from 1, 2, 3, and 4. In a further aspect, n is selected from 1, 2, and 3. In a still further aspect, n is selected from 1 and 2. In yet a further aspect, n is 4. In an even further aspect, n is 3. In a still further aspect, n is 2. In yet a further aspect, n is 1.

In one aspect, q, when present, is selected from 0 and 1. In a further aspect, q, when present, is 0. In a still further aspect, q, when present, is 1.

a. $Q^1$ and $Q^2$ Groups

In one aspect, each of $Q^1$ and $Q^2$ is independently selected from CH and N. In a further aspect, each of $Q^1$ and $Q^2$ is CH. In a still further aspect, each of $Q^1$ and $Q^2$ is N.

In a further aspect, $Q^1$ is CH and $Q^2$ is N. In a still further aspect, $Q^1$ is N and $Q^2$ is CH.

b. Z Groups

In a further aspect, Z is selected from O, S, and $NR^{40}$. In a still further aspect, Z is O. In yet a further aspect, Z is S. In an even further aspect, Z is $NR^{40}$.

c. $R^{1A}$ and $R^{1B}$ Groups

In one aspect, each of $R^{1a}$ and $R^{1b}$ is independently C1-C4 alkyl; or each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or each of $R^{1a}$ and $R^{1b}$ is hydrogen; or $R^{1a}$ is hydrogen, $R^{1b}$ is —$CH_2Cy^2$, and $R^4$ is —$C_6H_4R^{21}$.

In a further aspect, each of $R^{1a}$ and $R^{1b}$ is independently selected from methyl, ethyl, n-propyl, i-propyl, n-butyl, i-butyl, s-butyl, and t-butyl. In a still further aspect, each of $R^{1a}$ and $R^{1b}$ is independently selected from methyl, ethyl, n-propyl, and i-propyl. In yet a further aspect, each of $R^{1a}$ and $R^{1b}$ is independently selected from methyl and ethyl. In an even further aspect, each of $R^{1a}$ and $R^{1b}$ is ethyl. In a still further aspect, each of $R^{1a}$ and $R^{1b}$ is methyl.

In a further aspect, each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 3- to 7-membered cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise a 3- to 7-membered cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of $R^{1a}$ and $R^{1b}$ are optionally covalently bonded together and, together with the intermediate atoms, comprise a 3- to 7-membered cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 3- to 7-membered cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise an unsubstituted 3- to 7-membered cycloalkyl.

In a further aspect, each of $R^{1a}$ and $R^{1b}$ are optionally covalently bonded together and, together with the intermediate atoms, comprise a 3- to 6-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 3- to 5-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise a 3- to 4-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of $R^{1a}$ and $R^{1b}$ are optionally covalently bonded together and, together with the intermediate atoms, comprise a 4- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 5- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise a 6- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of $R^{1a}$ and $R^{1b}$ are optionally covalently bonded together and, together with the intermediate atoms, comprise a 4- to 6-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, each of $R^{1a}$ and $R^{1b}$ are optionally covalently bonded together and, together with the intermediate atoms, comprise a 4-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 3-membered cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise a 4-membered cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of $R^{1a}$ and $R^{1b}$ are optionally covalently bonded together and, together with the intermediate atoms, comprise a 4-membered cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 4-membered cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise an unsubstituted 4-membered cycloalkyl.

In a further aspect, each of $R^{1a}$ and $R^{1b}$ are optionally covalently bonded together and, together with the intermediate atoms, comprise a 5-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{1a}$ and $R^{1b}$ are optionally covalently bonded together and, together with the intermediate atoms, comprise a 5-membered cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{1a}$ and $R^{1b}$ are optionally covalently bonded together and, together with the intermediate atoms, comprise a 5-membered cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of R$^{1a}$ and R$^{1b}$ are optionally covalently bonded together and, together with the intermediate atoms, comprise a 5-membered cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{1a}$ and R$^{1b}$ are optionally covalently bonded together and, together with the intermediate atoms, comprise a 5-membered cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{1a}$ and R$^{1b}$ are optionally covalently bonded together and, together with the intermediate atoms, comprise an unsubstituted 5-membered cycloalkyl.

In a further aspect, each of R$^{1a}$ and R$^{1b}$ are optionally covalently bonded together and, together with the intermediate atoms, comprise a 6-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{1a}$ and R$^{1b}$ are optionally covalently bonded together and, together with the intermediate atoms, comprise a 6-membered cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{1a}$ and R$^{1b}$ are optionally covalently bonded together and, together with the intermediate atoms, comprise a 6-membered cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of R$^{1a}$ and R$^{1b}$ are optionally covalently bonded together and, together with the intermediate atoms, comprise a 6-membered cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{1a}$ and R$^{1b}$ are optionally covalently bonded together and, together with the intermediate atoms, comprise a 6-membered cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{1a}$ and R$^{1b}$ are optionally covalently bonded together and, together with the intermediate atoms, comprise an unsubstituted 6-membered cycloalkyl.

In a further aspect, each of R$^{1a}$ and R$^{1b}$ is hydrogen.

In a further aspect, R$^{1a}$ is hydrogen and R$^{1b}$ is —CH$_2$Cy$^2$.

d. R$^2$ and R$^3$ Groups

In one aspect, each of R$^2$ and R$^3$ is independently selected from hydrogen and C1-C4 alkyl. In a further aspect, each of R$^2$ and R$^3$ is hydrogen.

In a further aspect, each of R$^2$ and R$^3$ is independently selected from hydrogen, methyl, ethyl, n-propyl, and i-propyl. In a still further aspect, each of R$^2$ and R$^3$ is independently selected from hydrogen, methyl, and ethyl. In yet a further aspect, each of R$^2$ and R$^3$ is independently selected from hydrogen and ethyl. In an even further aspect, each of R$^2$ and R$^3$ is independently selected from hydrogen and methyl.

In a further aspect, each of R$^2$ and R$^3$ is independently C1-C4 alkyl. In a still further aspect, each of R$^2$ and R$^3$ is independently selected from methyl, ethyl, n-propyl, and i-propyl. In yet a further aspect, each of R$^2$ and R$^3$ is independently selected from methyl and ethyl. In an even further aspect, each of R$^2$ and R$^3$ is ethyl. In a still further aspect, each of R$^2$ and R$^3$ is methyl.

e. R$^4$ Groups

In one aspect, R$^4$ is selected from —NR$^{20a}$R$^{20b}$ and Cy$^1$; or R$^4$ is —C$_6$H$_4$C(O)NR$^{32a}$R$^{32b}$.

In a further aspect, R$^4$ is selected from —NR$^{20a}$R$^{20b}$ and Cy$^1$. In a still further aspect, R$^4$ is —NR$^{20a}$R$^{20b}$. In yet a further aspect, R$^4$ is —NHR$^{20a}$. In an even further aspect, R$^4$ is —NH$_2$. In an even further aspect, R$^4$ is Cy$^1$.

In a further aspect, R$^4$ is —C$_6$H$_4$C(O)NR$^{32a}$R$^{32b}$.

f. R$^{20a}$ and R$^{20b}$ Groups

In one aspect, each of R$^{20a}$ and R$^{20b}$, when present, is independently selected from hydrogen, C1-C4 alkyl, C1-C4 haloalkyl, cycloalkyl, and heteroaryl. In a further aspect, each of R$^{20a}$ and R$^{20b}$, when present, is hydrogen.

In a further aspect, each of R$^{20a}$ and R$^{20b}$, when present, is independently selected from hydrogen, C1-C4 alkyl, and C1-C4 haloalkyl. In a still further aspect, each of R$^{20a}$ and R$^{20b}$, when present, is independently selected from hydrogen, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, and —CH(CH$_2$F)(CH$_3$). In yet a further aspect, each of R$^{20a}$ and R$^{20b}$, when present, is independently selected from hydrogen, methyl, ethyl, —CH$_2$Cl, —CH$_2$CH$_2$Cl, —CH$_2$F, and —CH$_2$CH$_2$F. In an even further aspect, each of R$^{20a}$ and R$^{20b}$, when present, is independently selected from hydrogen, methyl, —CH$_2$Cl, and —CH$_2$F.

In a further aspect, each of R$^{20a}$ and R$^{20b}$, when present, is independently selected from hydrogen and C1-C4 alkyl. In a still further aspect, each of R$^{20a}$ and R$^{20b}$, when present, is independently selected from hydrogen, methyl, ethyl, n-propyl, and i-propyl. In yet a further aspect, each of R$^{20a}$ and R$^{20b}$, when present, is independently selected from hydrogen, methyl, and ethyl. In an even further aspect, each of R$^{20a}$ and R$^{20b}$, when present, is independently selected from hydrogen and ethyl. In a still further aspect, each of R$^{20a}$ and R$^{20b}$, when present, is independently selected from hydrogen and methyl.

In a further aspect, each of R$^{20a}$ and R$^{20b}$, when present, is C1-C4 alkyl. In a still further aspect, each of R$^{20a}$ and R$^{20b}$, when present, is independently selected from methyl, ethyl, n-propyl, and i-propyl. In yet a further aspect, each of R$^{20a}$ and R$^{20b}$, when present, is independently selected from methyl and ethyl. In an even further aspect, each of R$^{20a}$ and R$^{20b}$, when present, is ethyl. In a still further aspect, each of R$^{20a}$ and R$^{20b}$, when present, is methyl.

In a further aspect, each of R$^{20a}$ and R$^{20b}$, when present, is independently selected from hydrogen and C1-C4 haloalkyl. In a still further aspect, each of R$^{20a}$ and R$^{20b}$, when present, is independently selected from hydrogen, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, and —CH(CH$_2$F)(CH$_3$). In yet a further aspect, each of R$^{20a}$ and R$^{20b}$, when present, is independently selected from hydrogen, —CH$_2$Cl, —CH$_2$CH$_2$Cl, —CH$_2$F, and —CH$_2$CH$_2$F. In an even further aspect, each of R$^{20a}$ and R$^{20b}$, when present, is independently selected from hydrogen, —CH$_2$Cl, and —CH$_2$F.

In a further aspect, each of $R^{20a}$ and $R^{20b}$, when present, is independently selected from hydrogen, cycloalkyl, and heteroaryl. In a still further aspect, each of $R^{20a}$ and $R^{20b}$, when present, is independently selected from hydrogen, cyclopropyl, cyclobutyl, cyclopentyl, cyclohexyl, g. $R^{21}$ Groups In one aspect, $R^{21}$, when present, is selected from $-(CH_2)_qNR^{31a}R^{31b}$ and $-C(O)NR^{32a}R^{32b}$. In a further aspect, $R^{21}$, when present, is $-(CH_2)_qNR^{31a}R^{31b}$. In a still further aspect, $R^{21}$, when present, is $-C(O)NR^{32a}R^{32b}$.

h. $R^{31a}$, $R^{31b}$, $R^{32a}$, and $R^{32b}$ Groups

In one aspect, each of $R^{31a}$, $R^{31b}$, $R^{32a}$, and $R^{32b}$, when present, is independently selected from hydrogen and C1-C4 alkyl. In a further aspect, each of $R^{31a}$, $R^{31b}$, $R^{32a}$, and $R^{32b}$, when present, is hydrogen.

In a further aspect, each of $R^{31a}$, $R^{31b}$, $R^{32a}$, and $R^{32b}$, when present, is independently selected from hydrogen, methyl, ethyl, n-propyl, i-propyl, n-butyl, i-butyl, s-butyl, and t-butyl. In a still further aspect, each of $R^{31a}$, $R^{31b}$, $R^{32a}$, and $R^{32b}$, when present, is independently selected from hydrogen, methyl, ethyl, n-propyl, and i-propyl. In yet a further aspect, each of $R^{31a}$, $R^{31b}$, $R^{32a}$, and $R^{32b}$, when present, is independently selected from hydrogen, methyl, and ethyl. In an even further aspect, each of $R^{31a}$, $R^{31b}$, $R^{32a}$ and $R^{32b}$, when present, is independently selected from hydrogen and ethyl. In a still further aspect, each of $R^{31a}$, $R^{31b}$, $R^{32a}$, and $R^{32b}$, when present, is independently selected from hydrogen and methyl.

In a further aspect, each of $R^{31a}$, $R^{31b}$, $R^{32a}$, and $R^{32b}$, when present, is independently selected from methyl, ethyl, n-propyl, i-propyl, n-butyl, i-butyl, s-butyl, and t-butyl. In a still further aspect, each of $R^{31a}$, $R^{31b}$, $R^{32a}$, and $R^{32b}$, when present, is independently selected from methyl, ethyl, n-propyl, and i-propyl. In yet a further aspect, each of $R^{31a}$, $R^{31b}$, $R^{32a}$, and $R^{32b}$, when present, is independently selected from methyl, and ethyl. In an even further aspect, each of $R^{31a}$, $R^{31b}$, $R^{32a}$, and $R^{32b}$, when present, is ethyl. In a still further aspect, each of $R^{31a}$, $R^{31b}$, $R^{32a}$, and $R^{32b}$, when present, is methyl.

i. $R^{33}$ Groups

In one aspect, $R^{33}$ is selected from hydrogen and C1-C4 alkyl. In a further aspect, $R^{33}$ is hydrogen.

In a further aspect, $R^{33}$ is selected from hydrogen, methyl, ethyl, n-propyl, i-propyl, n-butyl, i-butyl, s-butyl, and t-butyl. In a still further aspect, $R^{33}$ is selected from hydrogen, methyl, ethyl, n-propyl, and i-propyl. In yet a further aspect, $R^{33}$ is selected from hydrogen, methyl, and ethyl. In an even further aspect, $R^{33}$ is selected from hydrogen and ethyl. In a still further aspect, $R^{33}$ is selected from hydrogen and methyl.

In a further aspect, $R^{33}$ is selected from methyl, ethyl, n-propyl, i-propyl, n-butyl, i-butyl, s-butyl, and t-butyl. In a still further aspect, $R^{33}$ is selected from methyl, ethyl, n-propyl, and i-propyl. In yet a further aspect, $R^{33}$ is selected from methyl and ethyl. In an even further aspect, $R^{33}$ is ethyl. In a still further aspect, $R^{33}$ is methyl.

j. $R^{40}$ Groups

In one aspect, $R^{40}$, when present, is selected from hydrogen and C1-C4 alkyl. In a further aspect, $R^{40}$ is hydrogen.

In a further aspect, $R^{40}$ is selected from hydrogen, methyl, ethyl, n-propyl, i-propyl, n-butyl, i-butyl, s-butyl, and t-butyl. In a still further aspect, $R^{40}$ is selected from hydrogen, methyl, ethyl, n-propyl, and i-propyl. In yet a further aspect, $R^{40}$ is selected from hydrogen, methyl, and ethyl. In an even further aspect, $R^{40}$ is selected from hydrogen and ethyl. In a still further aspect, $R^{40}$ is selected from hydrogen and methyl.

In a further aspect, $R^{40}$ is selected from methyl, ethyl, n-propyl, i-propyl, n-butyl, i-butyl, s-butyl, and t-butyl. In a still further aspect, $R^{40}$ is selected from methyl, ethyl, n-propyl, and i-propyl. In yet a further aspect, $R^{40}$ is selected from methyl and ethyl. In an even further aspect, $R^{40}$ is ethyl. In a still further aspect, $R^{40}$ is methyl.

k. $Cy^1$ Groups

In one aspect, $Cy^1$, when present, is selected from C5-C6 cycloalkyl, monocyclic heteroaryl, and $-C_6H_4R^{21}$ and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^1$, when present, is selected from C5-C6 cycloalkyl, monocyclic heteroaryl, and $-C_6H_4R^{21}$ and is substituted with 0-3 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is selected from C5-C6 cycloalkyl, monocyclic heteroaryl, and $-C_6H_4R^{21}$ and is substituted with 0-2 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is selected from C5-C6 cycloalkyl, monocyclic heteroaryl, and $-C_6H_4R^{21}$ and is substituted with 0-1 non-hydrogen group selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is selected from C5-C6 cycloalkyl, monocyclic heteroaryl, and $-C_6H_4R^{21}$ and is monosubstituted with a non-hydrogen group selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is selected from C5-C6 cycloalkyl, monocyclic heteroaryl, and $-C_6H_4R^{21}$ and is unsubstituted.

In a further aspect, $Cy^1$, when present, is selected from C5-C6 cycloalkyl, monocyclic heteroaryl, and $-C_6H_4R^{21}$ and is monosubstituted with a group selected from $-NH_2$, C1-C4 alkylamino, and (C1-C4)(C1-C4) dialkylamino. In a still further aspect, $Cy^1$, when present, is selected from C5-C6 cycloalkyl, monocyclic heteroaryl, and $-C_6H_4R^{21}$ and is monosubstituted with a group selected from $-NH_2$ and C1-C4 alkylamino. In yet a further aspect, $Cy^1$, when present, is selected from C5-C6 cycloalkyl, monocyclic heteroaryl, and $-C_6H_4R^{21}$ and is monosubstituted with a $-NH_2$ group.

In a further aspect, $Cy^1$, when present, is C5-C6 cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C5-C6 cycloalkyl substituted with 0-3 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is C5-C6 cycloalkyl substituted with 0-2 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is C5-C6 cycloalkyl substituted with 0-1 non-hydrogen group selected from halogen, $-NH_2$, C1-C4 alkyl, C1-C4 haloalkyl, C1-C4 hydroxyalkyl, C1-C4 alkoxy, C1-C4 alkylamino, and (C1-

C4)(C1-C4) dialkylamino. In a still further aspect, Cy$^1$, when present, is C5-C6 cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$, when present, is unsubstituted C5-C6 cycloalkyl.

In a further aspect, Cy$^1$, when present, is selected from cyclopentyl and cyclohexyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$, when present, is cyclopentyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$, when present, is cyclohexyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, Cy$^1$ is monocyclic heteroaryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$ is monocyclic heteroaryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$ is monocyclic heteroaryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^1$ is monocyclic heteroaryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$ is monocyclic heteroaryl monosubstituted with a group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$ is unsubstituted monocyclic heteroaryl.

In a further aspect, Cy$^1$ is selected from pyridinyl, thiophenyl, furanyl, oxazolyl, thiazolyl, and 1,2,4-thiazolyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$ is selected from pyridinyl, oxazolyl, thiazolyl, and 1,2,4-thiazolyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$ is selected from oxazolyl, thiazolyl, and 1,2,4-thiazolyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^1$ is pyridinyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, Cy$^1$ is —C$_6$H$_4$R$^{21}$ substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$ is —C$_6$H$_4$R$^{21}$ substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$ is —C$_6$H$_4$R$^{21}$ substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^1$ is —C$_6$H$_4$R$^{21}$ substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^1$ is —C$_6$H$_4$R$^{21}$ monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^1$ is unsubstituted —C$_6$H$_4$R$^{21}$.

In a further aspect, Cy$^1$ is —C$_6$H$_4$NH$_2$. In a still further aspect, Cy$^1$ is —C$_6$H$_4$CH$_2$NH$_2$.

In a further aspect, Cy$^1$ is monocyclic heteroaryl substituted with a group selected from —(CH$_2$)$_q$NR$^{31a}$R$^{31b}$ and —C(O)NR$^{32a}$R$^{32b}$. In a still further aspect, Cy$^1$ is monocyclic heteroaryl substituted with a group selected from —NH$_2$ and —C(O)NH$_2$. In yet a further aspect, Cy$^1$ is monocyclic heteroaryl substituted with a —C(O)NH$_2$ group. In an even further aspect, Cy$^1$ is monocyclic heteroaryl substituted with a —NH$_2$ group.

1. Cy$^2$ Groups

In one aspect, Cy$^2$ is selected from C3-C6 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, Cy$^2$ is selected from C3-C6 cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$ is selected from C3-C6 cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$ is selected from C3-C6 cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^2$ is selected from C3-C6 cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$ is unsubstituted C3-C6 cycloalkyl.

In a further aspect, Cy$^2$ is cyclobutyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$ is cyclobutyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is cyclobutyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$ is cyclobutyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$ is cyclobutyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is unsubstituted cyclobutyl.

In a further aspect, $Cy^2$ is cyclopentyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$ is cyclopentyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is cyclopentyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$ is cyclopentyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$ is cyclopentyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is unsubstituted cyclopentyl.

In a further aspect, $Cy^2$ is cyclohexyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$ is cyclohexyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is cyclohexyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$ is cyclohexyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$ is cyclohexyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$ is unsubstituted cyclohexyl.

m. $Cy^3$ Groups

In one aspect, $Cy^3$ is selected from C3-C6 cycloalkyl, monocyclic heteroaryl, and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^3$ is selected from C3-C6 cycloalkyl, monocyclic heteroaryl, and aryl and is substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is selected from C3-C6 cycloalkyl, monocyclic heteroaryl, and aryl and is substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is selected from C3-C6 cycloalkyl, monocyclic heteroaryl, and aryl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is selected from C3-C6 cycloalkyl, monocyclic heteroaryl, and aryl and is monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is selected from C3-C6 cycloalkyl, monocyclic heteroaryl, and aryl and is unsubstituted.

In a further aspect, $Cy^3$ is C3-C6 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is C3-C6 cycloalkyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is C3-C6 cycloalkyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is C3-C6 cycloalkyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is C3-C6 cycloalkyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted C3-C6 cycloalkyl.

In a further aspect, $Cy^3$ is cyclobutyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is Cyclobutyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is cyclobutyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is Cyclobutyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is cyclobutyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted cyclobutyl.

In a further aspect, $Cy^3$ is cyclopentyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is Cyclopentyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is cyclopentyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is Cyclopentyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is cyclopentyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted cyclopentyl.

In a further aspect, $Cy^3$ is cyclohexyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is Cyclohexyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is cyclohexyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is Cyclohexyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is cyclohexyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted cyclohexyl.

In a further aspect, $Cy^3$ is selected from monocyclic heteroaryl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is selected from monocyclic heteroaryl and aryl and is substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is selected from monocyclic heteroaryl and aryl and is substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is selected from monocyclic heteroaryl and aryl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is selected from monocyclic heteroaryl and aryl and is monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is selected from monocyclic heteroaryl and aryl and is unsubstituted.

In a further aspect, $Cy^3$ is monocyclic heteroaryl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is Monocyclic heteroaryl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is monocyclic heteroaryl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is Monocyclic heteroaryl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is monocyclic heteroaryl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted monocyclic heteroaryl.

In a further aspect, $Cy^3$ is aryl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is Aryl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is aryl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$ is Aryl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$ is aryl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$ is unsubstituted aryl.

In a further aspect, Cy$^3$ is C6-aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$ is C6-aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^3$ is C6-aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^3$ is C6-aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$ is C6-aryl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^3$ is unsubstituted C6-aryl.

2. Example Compounds

In one aspect, a compound can be present as one or more of the following structures:

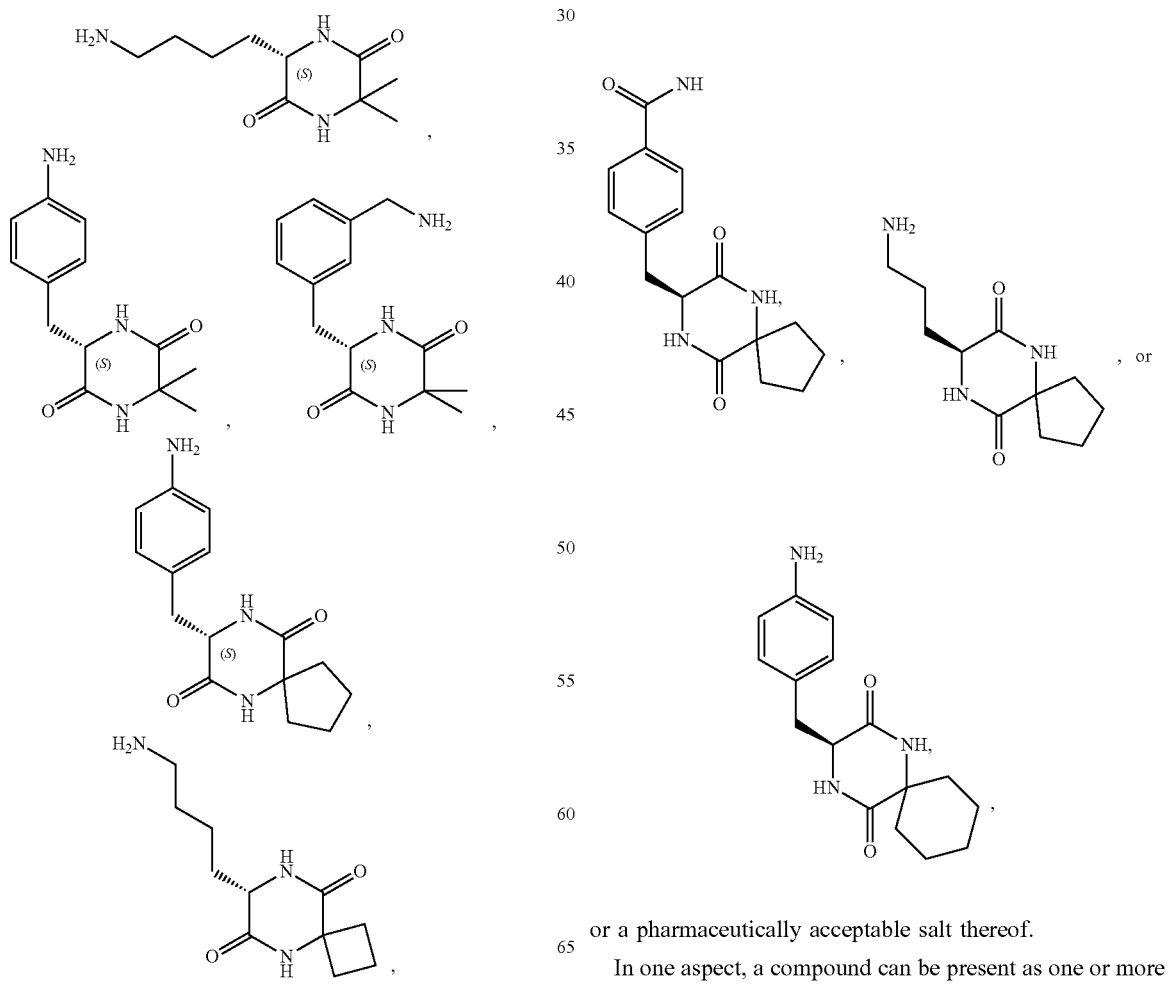

-continued

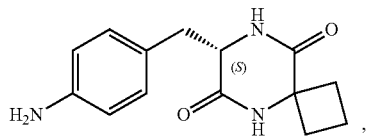

or a pharmaceutically acceptable salt thereof.

In one aspect, a compound can be present as one or more of the following structures:

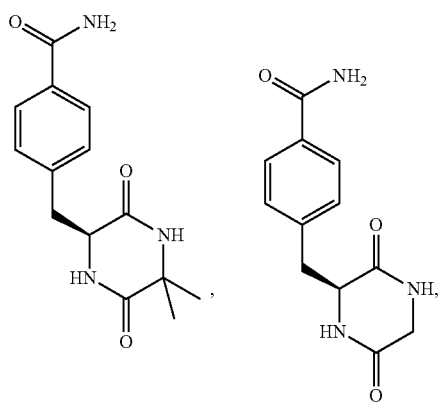

or a pharmaceutically acceptable salt thereof.

In one aspect, a compound can be present as one or more of the following structures:

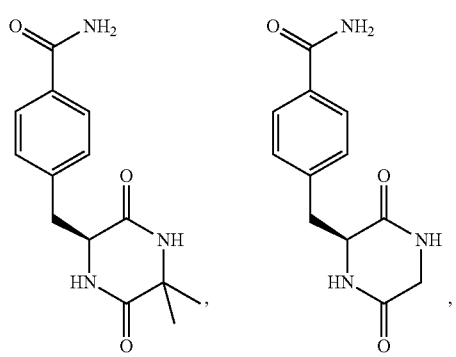

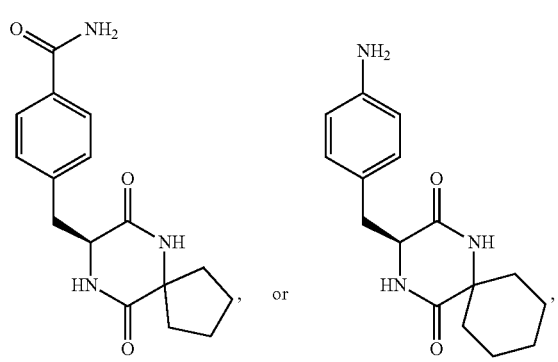

or a pharmaceutically acceptable salt thereof.

In one aspect, a compound can be present as one or more of the following structures:

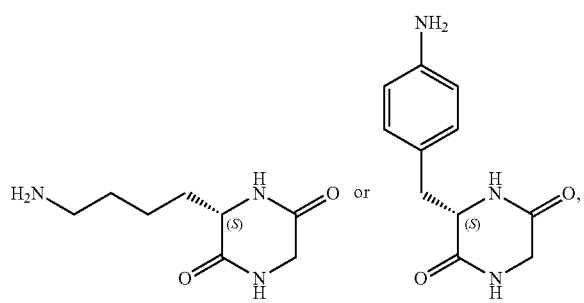

or a pharmaceutically acceptable salt thereof.

In one aspect, a compound can be present as:

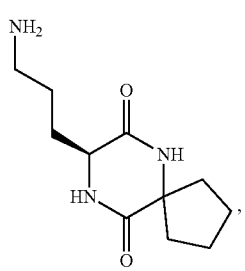 [SMILES: NCCC[C@@H]1NC(=O)C2(CCCC2)NC1=O]

or a pharmaceutically acceptable salt thereof.

In one aspect, a compound cannot be:

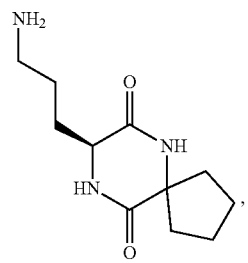 [SMILES: NCCC[C@@H]1NC(=O)C2(CCCC2)NC1=O]

or a pharmaceutically acceptable salt thereof.

In one aspect, a compound cannot be:

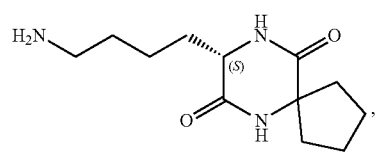

or a pharmaceutically acceptable salt thereof.

In one aspect, a compound cannot be:

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of TGF-β, and such activity can be determined using the assay methods described herein.

In one aspect, a compound can be selected from:

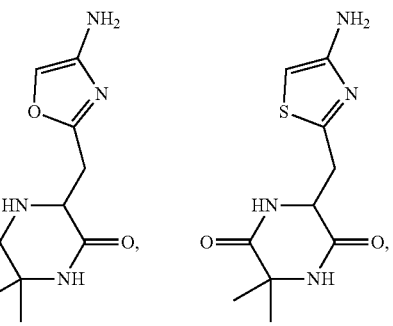

-continued
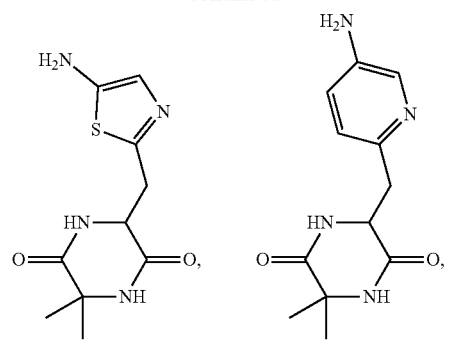
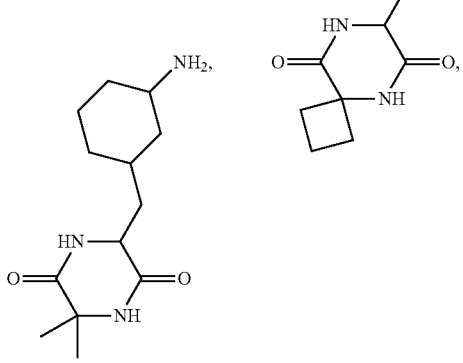
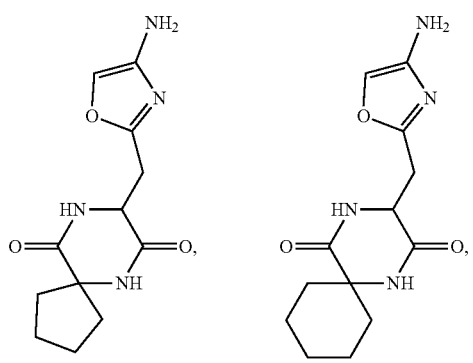
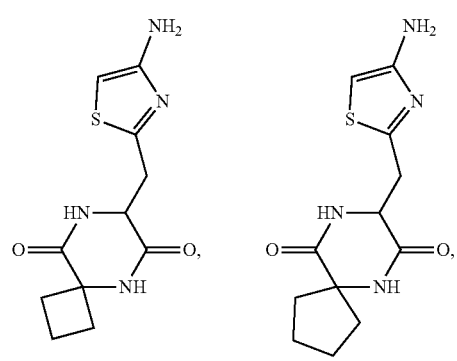
-continued
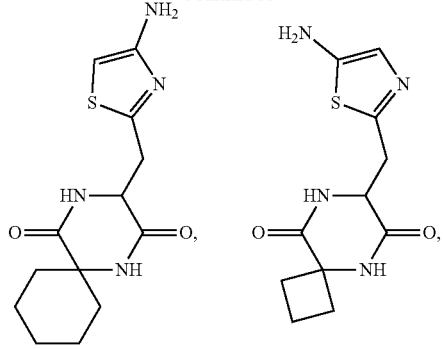
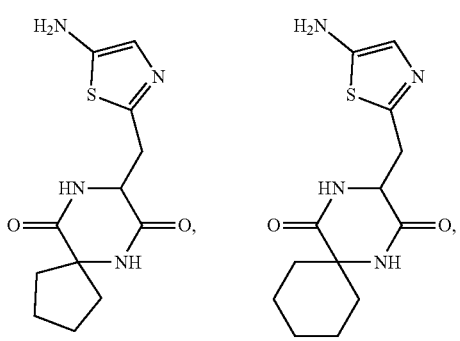
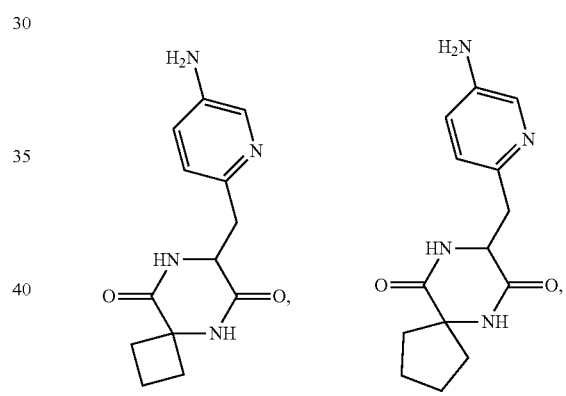
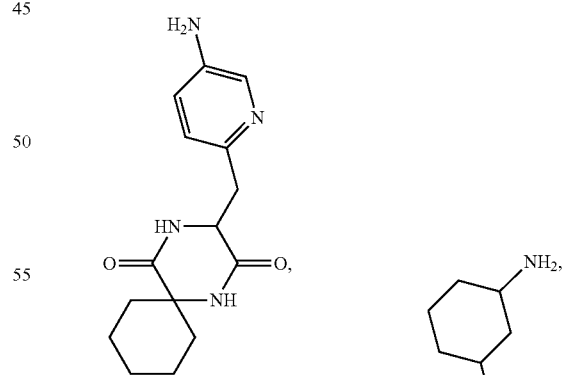
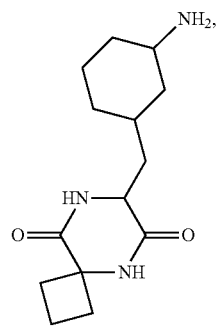

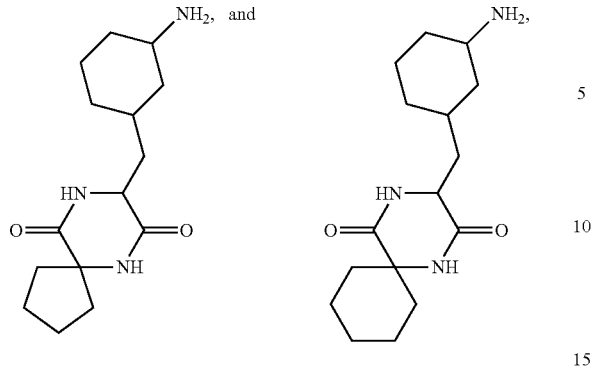
or a pharmaceutically acceptable salt thereof.
In one aspect, a compound can be selected from:
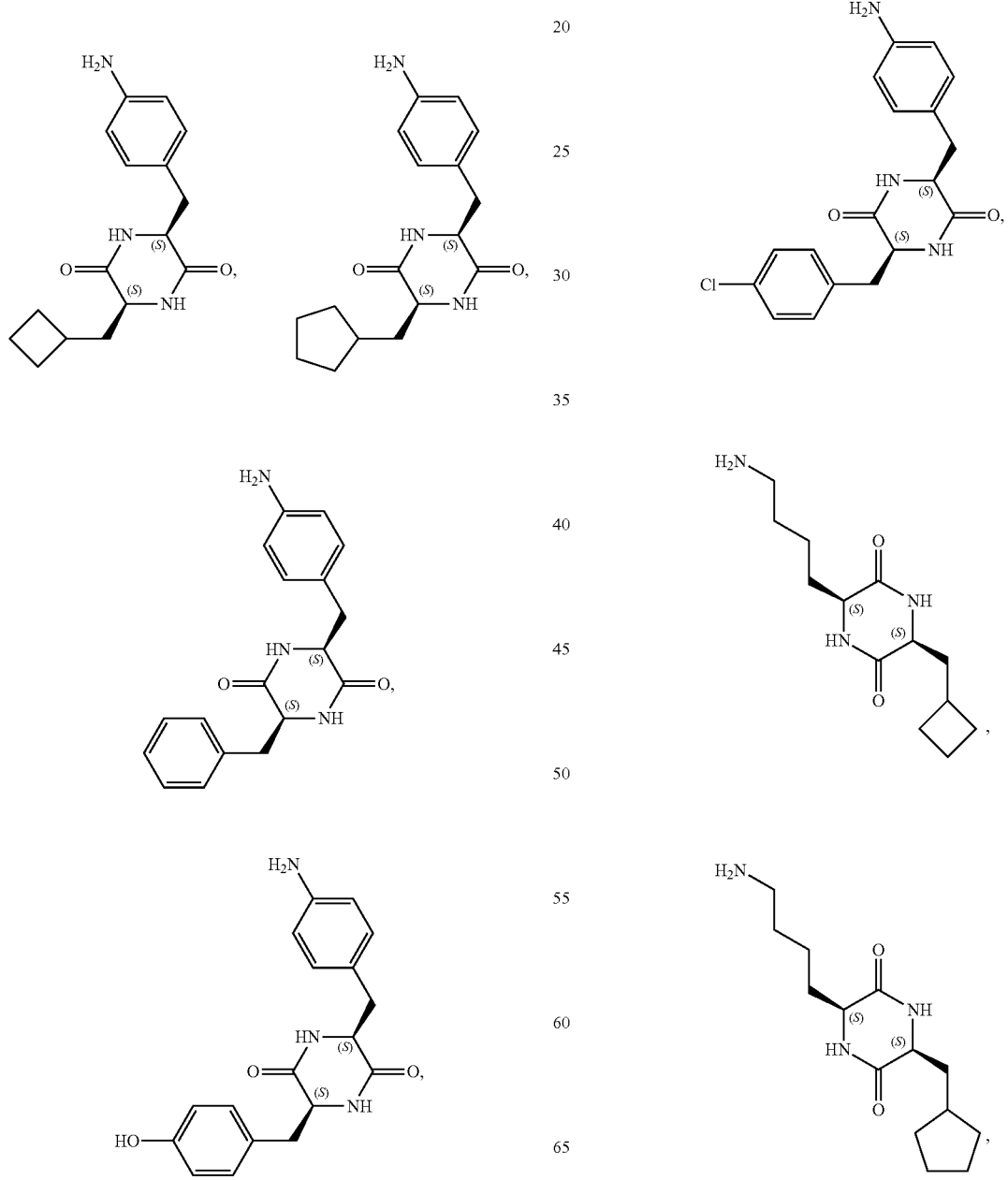

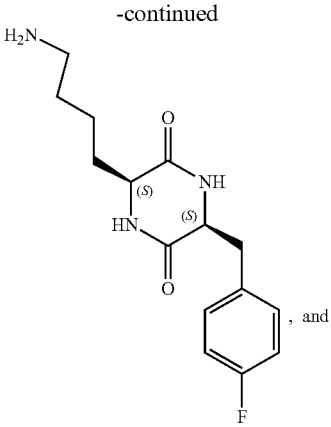
, and
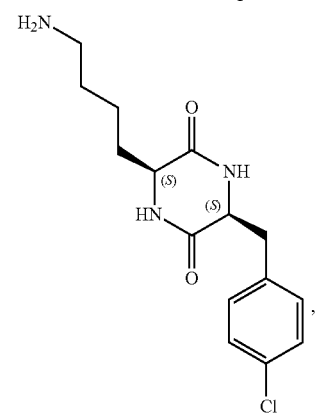
,
or a pharmaceutically acceptable salt thereof.
In one aspect, a compound can be selected from:
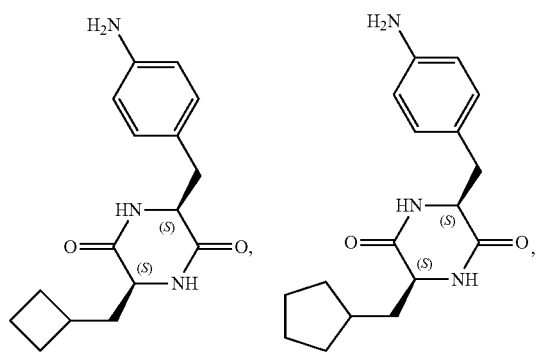
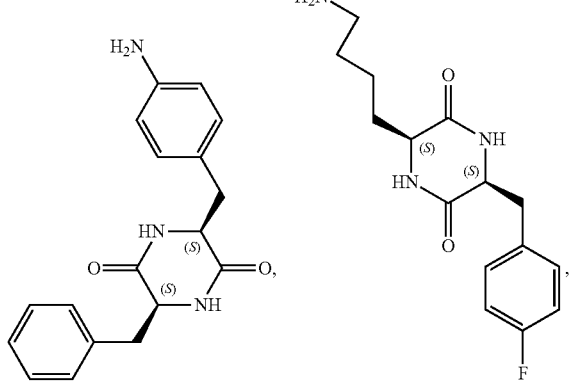
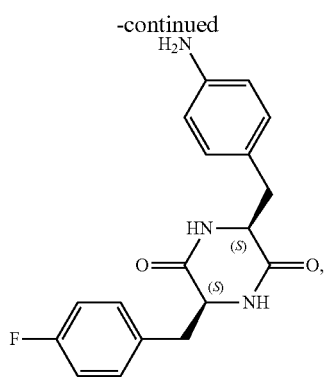
,
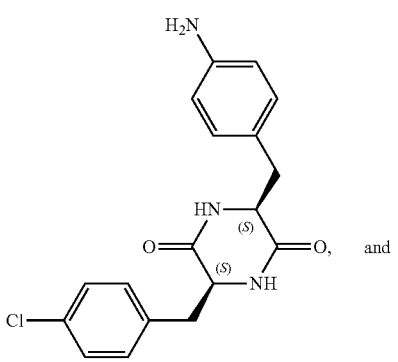
, and
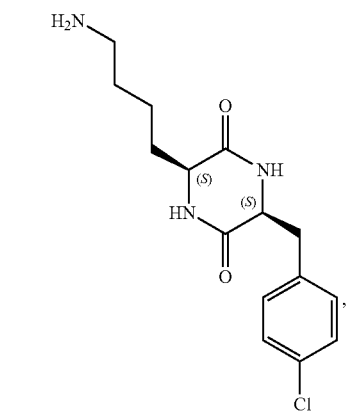
,
or a pharmaceutically acceptable salt thereof.
In one aspect, a compound can be selected from:
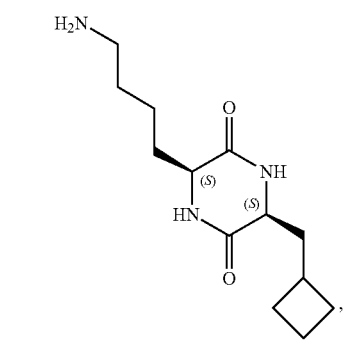
,

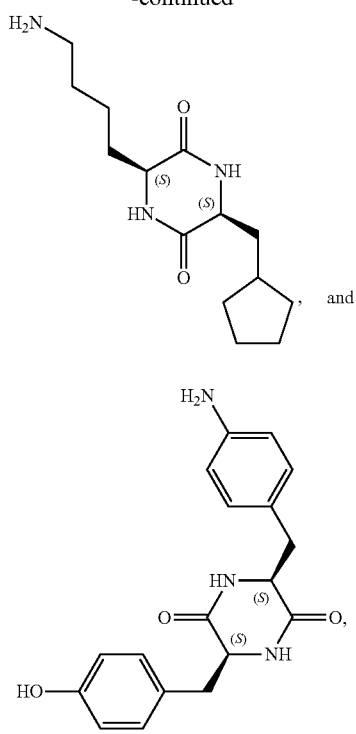

or a pharmaceutically acceptable salt thereof.

In one aspect, a compound can be selected from:

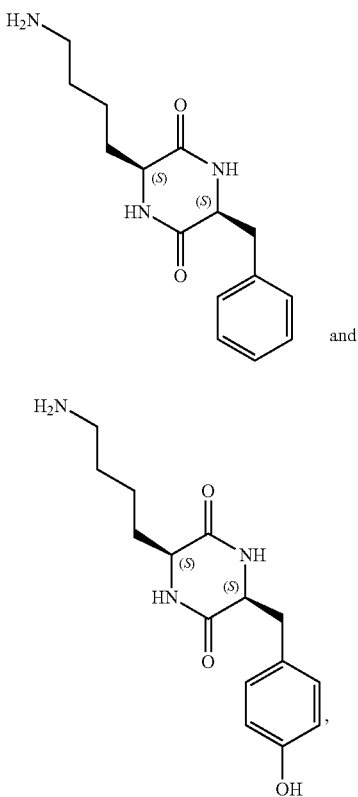

or a pharmaceutically acceptable salt thereof.

C. Pharmaceutical Compositions

In one aspect, the invention relates to pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of cancer. In a still further aspect, the mammal has been diagnosed with a need for treatment of cancer prior to the administering step.

In a further aspect, the pharmaceutical composition is administered following identification of the mammal in need of treatment of a fibrotic disorder. In a still further aspect, the mammal has been diagnosed with a need for treatment of a fibrotic disorder prior to the administering step.

In a further aspect, the pharmaceutical composition is administered following identification of the mammal in need of immunotherapy. In a still further aspect, the mammal has been diagnosed with a need for immunotherapy prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of TGF-β. The method also includes the administration of a therapeutically effect amount of the compound for the treatment of patient having a predisposition for being afflicted with a disorder associated with TGF-β activity. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the virus.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one agent known to treat cancer. In a still further aspect, the cancer is selected from multiple myeloma and a hematologic malignancy.

In a further aspect, the composition further comprises at least one agent known to have a side effect of increasing the risk of cancer.

In a further aspect, the composition further comprises at least one agent known to treat a fibrotic disorder. In a still further aspect, the fibrotic disorder is found in the liver, the lung, the cardiac muscle, the kidney, the skin or the eye. In yet a further aspect, the fibrotic disorder is found in the liver. In an even further aspect, fibrotic disorder is glaucoma, amyotropic lateral sclerosis, or muscular dystrophy.

In a further aspect, the composition further comprises at least one agent known to have a side effect of increasing the risk of a fibrotic disorder.

In a further aspect, the composition further comprises at least one agent known to treat an immune dysfunction.

In a further aspect, the composition further comprises at least one agent known to have a side effect of increasing the risk of an immune dysfunction.

It is understood that the disclosed compositions can be prepared from the disclosed compounds. It is also understood that the disclosed compositions can be employed in the disclosed methods of using.

D. Methods of Making the Compounds

In various aspects, the inventions relates to methods of making compounds useful to treat disorders associated with TGF-β activity such as, for example, cancers, in particular, multiple myeloma and hematologic malignancies, immune dysfunction, and fibrotic disorders, in particular, liver fibrosis, diabetic nephropathy, muscular dystrophy, amyotrophic lateral sclerosis, and glaucoma. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, piperazine-2,5-diones can be prepared as shown below.

SCHEME 1A.

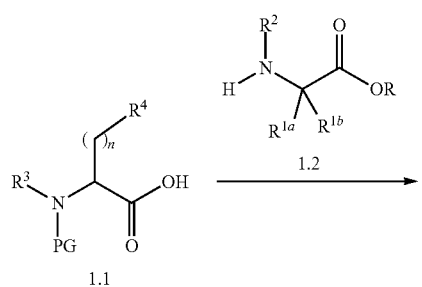

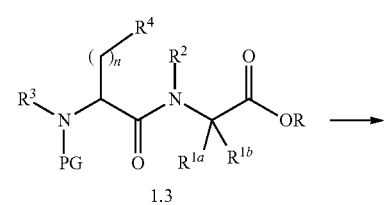

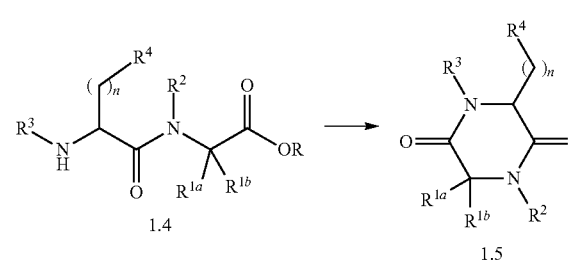

Compounds are represented in generic form, with substituents as noted in compound descriptions elsewhere herein, wherein PG is a protecting group, and wherein R is selected from methyl and ethyl. A more specific example is set forth below.

Scheme 1B.

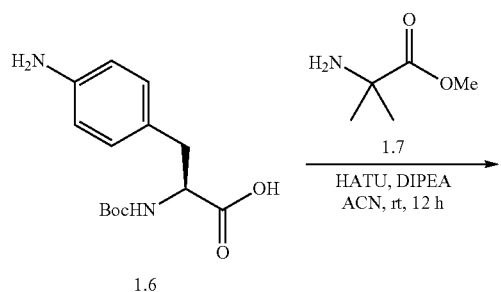

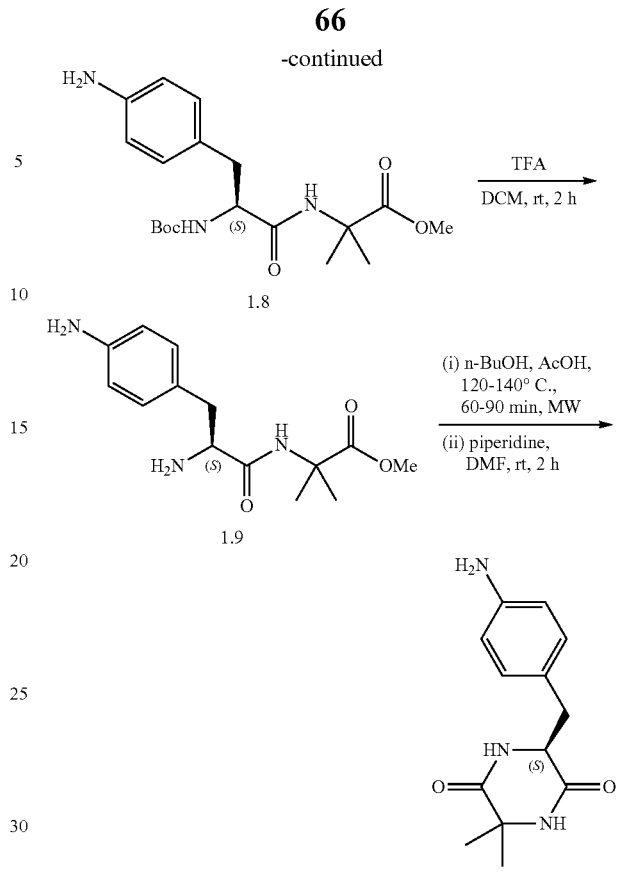

In one aspect, compounds of type 1.10, and similar compounds, can be prepared according to reaction Scheme 1B above. Thus, compounds of type 1.8 can be prepared by a coupling reaction of an appropriate carboxylic acid, e.g., 1.6 as shown above, and an appropriate amine, e.g., 1.7 as shown above. Appropriate carboxylic acids and appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethyl amine (DIPEA), in an appropriate solvent, e.g., acetonitrile, for an appropriate period of time, e.g., 12 hours. Compounds of type 1.9 can be prepared by deprotection of an appropriate amine, e.g., 1.8 as shown above. The deprotection is carried out in the presence of an appropriate acid, e.g., trifluoroacetic acid (TFA), in an appropriate solvent, e.g., dichloromethane, for an appropriate period of time, e.g., 2 hours. Compounds of type 1.10 can be prepared by cyclization of an appropriate ester, e.g., 1.9 as shown above. The cyclization is carried out in the presence of an appropriate acid, e.g., acetic acid, in an appropriate solvent, e.g., n-butanol, at an appropriate temperature, e.g., 120-140° C., for an appropriate period of time, e.g., 60-90 minutes hours, followed by addition of an appropriate base, e.g., piperidine, in an appropriate solvent, e.g., dimethylformamide, for an appropriate period of time, e.g., 2 hours. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide substituted piperazine-2,5-diones similar to Formula 1.5.

E. Methods of Using the Compounds

The compounds and pharmaceutical compositions of the invention are useful in treating or controlling disorders associated with TGF-β activity, in particular, cancers such as, for example, multiple myeloma and hematologic malignancies, immunotherapy, and fibrotic disorders such as, for example, liver fibrosis, amyoptrophic lateral sclerosis, diabetic nephropathy, muscular dystrophy, and glaucoma.

Examples of cancers for which the compounds and compositions can be useful in treating, include, but are not limited to carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas Examples of fibrotic disorders for which the compounds and compositions can be useful in treating, include, but are not limited to, pulmonary fibrosis, glomerulonephritis, liver cirrhosis, diabetic nephropathy, proliferative vitreoretinopathy, systemic sclerosis, scleroderma, muscular dystrophy, amyotrophic lateral sclerosis, and glaucoma.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cancer, immune dysfunction, or of a fibrotic disorder.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a cancer, immune dysfunction, or a fibrotic disorder.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with TGF-β activity, in particular, cancers, immune dysfunction, and fibrotic disorders. Thus, provided is a method comprising administering a therapeutically effective amount of a composition comprising a disclosed compound to a subject. In a further aspect, the method can be a method for treating cancer. In a still further aspect, the method can be a method for treating a fibrotic disorder. In a still further aspect, the method can be a method for treating immune dysfunction.

a. Treating Cancer

In one aspect, disclosed are methods of treating cancer associated with TGF-β activity in a mammal, the method comprising the step of administering to the mammal an effective amount of at least one disclosed compound, or a pharmaceutically acceptable salt thereof.

In one aspect, disclosed are methods for treating cancer in a subject, the method comprising the step of administering to the subject an effective amount of at least one compound having a structure represented by a formula:

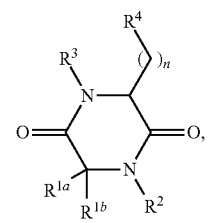

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from $-NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and $-C_6H_4R^{21}$ and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from $-(CH_2)_qNR^{31a}R^{31b}$ and $-C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is $-C_6H_4C(O)NR^{32a}R^{32b}$; or a pharmaceutically acceptable salt thereof, thereby treating cancer in the subject.

In one aspect, disclosed are methods for treating cancer in a subject, the method comprising the step of administering to the subject an effective amount of at least one compound having a structure represented by a formula:

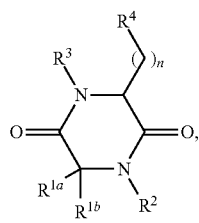

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from $-NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and $-C_6H_4R^{21}$ and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from $-(CH_2)_qNR^{31a}R^{31b}$ and $-C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is $-C_6H_4C(O)NR^{32a}R^{32b}$; provided that when n is 1 and each of $R^{1a}$ and $R^{1b}$ together comprise a 3-membered cycloalkyl then $Cy^1$, when present, is not monocyclic heteroaryl, and provided that when $R^4$ is $-NR^{20a}R^{20b}$ then each of $R^{1a}$ and $R^{1b}$ is independently C1-C4 alkyl, or a pharmaceutically acceptable salt thereof, thereby treating cancer in the subject.

In one aspect, disclosed are methods for treating cancer in a subject, the method comprising the step of administering to the subject an effective amount of at least one compound having a structure selected from:

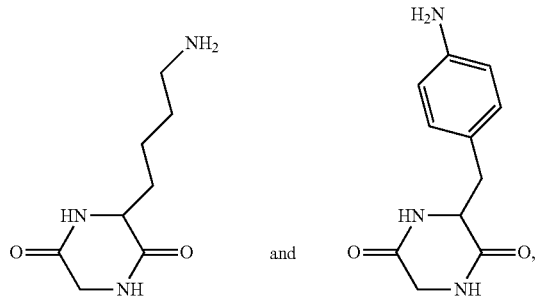

or a pharmaceutically acceptable salt thereof, thereby treating cancer in the subject.

Examples of cancers include, but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes, and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In an even further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from an ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopercytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In a further aspect, the subject has been diagnosed with a need for treatment of cancer prior to the administering step.

In a further aspect, the subject is a mammal. In a still further aspect, the mammal is a human.

In a further aspect, the method further comprises the step of identifying a subject in need of treatment of cancer.

In a further aspect, the method further comprises the step of administering a therapeutically effective amount of at least one chemotherapeutic agent. Examples of chemotherapeutic agents include, but are not limited to, alkylating agents such as busulfan, cis-platin, mitomycin C, and carboplatin; antimitotic agents such as colchicine, vinblastine, paclitaxel (e.g., TAXOL®), and docetaxel; topoisomerase I inhibitors such as camptothecin and topotecan; topoisomerase II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea, gemcitabine, capecitabine and thioguanine; antibodies such as HERCEPTIN® and RITUXAN®, as well as other known chemotherapeutics such as photofrin, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

b. Treating a Fibrotic Disorder

In one aspect, disclosed are methods of treating a fibrotic disorder associated with TGF-β activity in a mammal, the method comprising the step of administering to the mammal an effective amount of at least one disclosed compound, or a pharmaceutically acceptable salt thereof.

In one aspect, disclosed are methods for treating a fibrotic disorder in a subject, the method comprising the step of administering to the subject an effective amount of at least one compound having a structure represented by a formula:

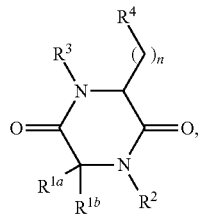

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$; provided that when n is 1 and each of $R^{1a}$ and $R^{1b}$ together comprise a 3-membered cycloalkyl then $Cy^1$, when present, is not monocyclic heteroaryl, and provided that when $R^4$ is —$NR^{20a}R^{20b}$ then each of $R^{1a}$ and $R^{1b}$ is independently C1-C4 alkyl, or a pharmaceutically acceptable salt thereof, thereby treating the fibrotic disorder in the subject.

In one aspect, disclosed are methods for treating a fibrotic disorder in a subject, the method comprising the step of administering to the subject an effective amount of at least one compound having a structure represented by a formula:

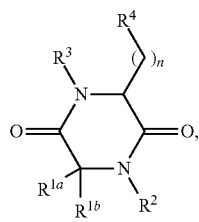

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$; or a pharmaceutically acceptable salt thereof, thereby treating the fibrotic disorder in the subject.

In one aspect, disclosed are methods for treating a fibrotic disorder in a subject, the method comprising the step of administering to the subject an effective amount of at least one compound having a structure selected from:

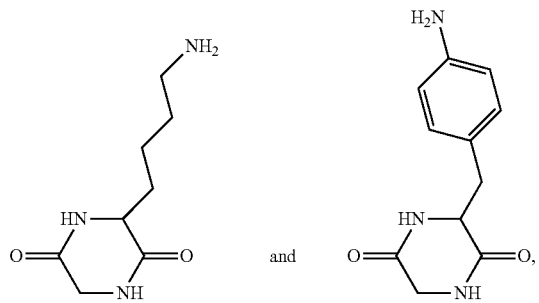 [SMILES: NCCCCC1NC(=O)CNC1=O ; "and" ; Nc1ccc(CC2NC(=O)CNC2=O)cc1]

or a pharmaceutically acceptable salt thereof, thereby treating the fibrotic disorder in the subject.

Examples of fibrotic disorders for which the compounds and compositions can be useful in treating, include, but are not limited to, pulmonary fibrosis, diabetic nephropathy, glomerulonephritis, liver cirrhosis, muscular dystrophy, proliferative vitreoretinopathy, systemic sclerosis, scleroderma, amyotrophic lateral sclerosis, and glaucoma.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the fibrotic disorder.

In a further aspect, the method further comprises the step of administering a therapeutically effective amount of at least one agent known to treat a fibrotic disorder. In a still further aspect, the at least one agent is selected from pirfenidone, nintedanib, a prostaglandin such as latanoprost and bimaotoprost, a beta blocker such as timolol and betaxolol, an alpha-adrenergic agonist such as apraclonidine and brimonidine, a carbonic anhydrase inhibitor such as dorzolamide and brinzolamide, a moitic or cholinergic agent such as pilocarpine, a diuretic, an angiotenisin-converting enzyme (ACE) inhibitor, an angiotensin II receptor blocker, an anti-inflammatory agent, and an anti-fibrotic agent.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

c. Treating an Immune Dysfunction

In one aspect, disclosed are methods of treating an immune dysfunction associated with TGF-β activity in a mammal, the method comprising the step of administering to the mammal an effective amount of at least one disclosed compound, or a pharmaceutically acceptable salt thereof.

In one aspect, disclosed are methods for treating an immune dysfunction in a subject, the method comprising the step of administering to the subject an effective amount of at least one compound having a structure represented by a formula:

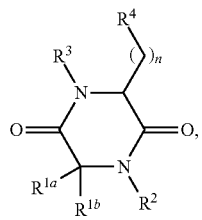

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$; or a pharmaceutically acceptable salt thereof, thereby treating the immune dysfunction in the subject.

In one aspect, disclosed are methods for treating an immune dysfunction in a subject, the method comprising the step of administering to the subject an effective amount of at least one compound having a structure selected from:

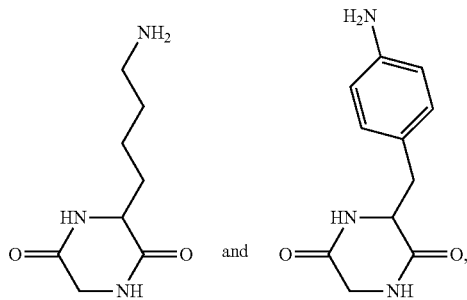 [SMILES: NCCCCC1NC(=O)CNC1=O ; Nc1ccc(CC2NC(=O)CNC2=O)cc1]

or a pharmaceutically acceptable salt thereof, thereby treating the immune dysfunction in the subject.

In a further aspect, the subject has been diagnosed with a need for immunotherapy prior to the administering step. Examples of immunotherapy include, but are not limited to injection immunotherapy, topical immunotherapy, BCG immunotherapy, dendritic cell-based pump-priming, T-cell adoptive transfer, administration of an immunomodulator, immune enhancement therapy, use of genetically engineered T-cells, antimicrobial immunotherapy, and immunosuppression.

In a further aspect, the subject is a mammal. In a still further aspect, the mammal is a human.

In a further aspect, the method further comprises the step of identifying a subject in need of immunotherapy.

In a further aspect, the method further comprises the step of administering a therapeutically effective amount of at least one agent known to treat an immune dysfunction. Examples of agents known to treat immune dysfunction include, but are not limited to, interleukins (i.e., IL-2, IL-7, and IL-12), cytokines (i.e., interferons, G-CSF, imiquimod), chemokines (i.e., CCL3, CCL26, and CXCL7), immunomodulatory imide drugs (i.e., thalidomide, lenalidomide, pomalidomide, and apremilast), cytosine phosphate-guanosine, oligodeoxynulceotides, glucans, cytostatic drugs, glucocorticoids, and immunosuppressive antibodies.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting TGF-B Activity in a Subject

In one aspect, disclosed are methods for inhibiting TGF-β activity in a subject, the method comprising the step of administering to the subject an effective amount of at least one compound having a structure represented by a formula:

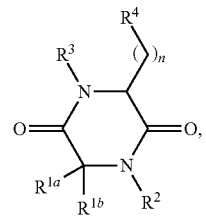

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4)

dialkylamino; and wherein R$^{21}$, when present, is selected from —(CH$_2$)$_q$NR$^{31a}$R$^{31b}$ and —C(O)NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$; or wherein R$^{1a}$ is hydrogen, R$^{1b}$ is —CH$_2$Cy$^3$ and R$^4$ is —C$_6$H$_4$R$^{21}$; wherein Cy$^3$ is selected from C3-C6 cycloalkyl, monocyclic heteroaryl, and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof, thereby inhibiting TGF-β activity in the subject.

In one aspect, disclosed are methods of inhibiting TGF-β activity in a mammal, the method comprising the step of administering to the mammal a therapeutically effective amount of at least one disclosed compound, or a pharmaceutically acceptable salt thereof.

In one aspect, disclosed are methods for inhibiting TGF-β activity in a subject, the method comprising the step of administering to the subject an effective amount of at least one compound having a structure represented by a formula:

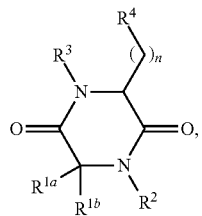

wherein n is selected from 1, 2, 3, and 4; wherein each of R$^{1a}$ and R$^{1b}$ is independently C1-C4 alkyl; or wherein each of R$^{1a}$ and R$^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of R$^2$ and R$^3$ is independently selected from hydrogen and C1-C4 alkyl; and wherein R$^4$ is selected from —NHR$^{20}$ and Cy$^1$; wherein R$^{20}$, when present, is selected from hydrogen and C1-C4 alkyl; wherein Cy$^1$, when present, is selected from C5-C6 cycloalkyl, monocyclic heteroaryl, and —C$_6$H$_4$R$^{21}$ and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein R$^{21}$, when present, is selected from —(CH$_2$)$_q$NR$^{31a}$R$^{31b}$ and —C(O)NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$; or a pharmaceutically acceptable salt thereof, thereby inhibiting TGF-β activity in the subject.

In one aspect, disclosed are methods for inhibiting TGF-β activity in a subject, the method comprising the step of administering to the subject an effective amount of at least one compound having a structure represented by a formula:

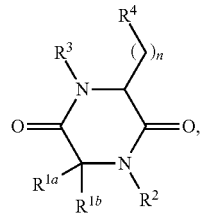

wherein n is selected from 1, 2, 3, and 4; wherein each of R$^{1a}$ and R$^{1b}$ is independently C1-C4 alkyl; or wherein each of R$^{1a}$ and R$^{1b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of R$^2$ and R$^3$ is independently selected from hydrogen and C1-C4 alkyl; and wherein R$^4$ is selected from —NHR$^{20}$ and Cy$^1$; wherein R$^{20}$, when present, is selected from hydrogen and C1-C4 alkyl; wherein Cy$^1$, when present, is selected from C5-C6 cycloalkyl, monocyclic heteroaryl, and —C$_6$H$_4$R$^{21}$ and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein R$^{21}$, when present, is selected from —(CH$_2$)$_q$NR$^{31a}$R$^{31b}$ and —C(O)NR$^{32a}$R$^{32b}$; wherein q, when present, is selected from 0 and 1; wherein each of R$^{31a}$, R$^{31b}$, R$^{32a}$, and R$^{32b}$, when present, is independently selected from hydrogen and C1-C4 alkyl; or wherein each of R$^{1a}$ and R$^{1b}$ is hydrogen and R$^4$ is —C$_6$H$_4$C(O)NR$^{32a}$R$^{32b}$; provided that when n is 1 and each of R$^{1a}$ and R$^{1b}$ together comprise a 3-membered cycloalkyl then Cy$^1$, when present, is not monocyclic heteroaryl, and provided that when R$^4$ is —NR$^{20a}$R$^{20b}$ then each of R$^{1a}$ and R$^{1b}$ is independently C1-C4 alkyl, or a pharmaceutically acceptable salt thereof, thereby inhibiting TGF-β activity in the subject.

In one aspect, disclosed are methods for inhibiting TGF-β activity in a subject, the method comprising the step of administering to the subject an effective amount of at least one compound having a structure selected from:

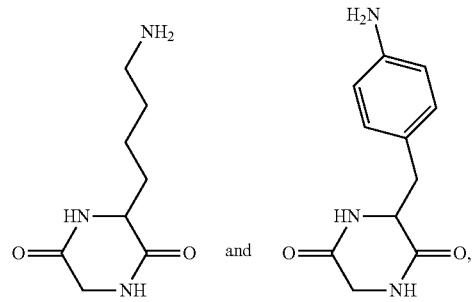

or a pharmaceutically acceptable salt thereof, thereby inhibiting TGF-β activity in the subject.

In a further aspect, the compound exhibits inhibition of TGF-β activity. In a still further aspect, the compound exhibits a decrease in TGF-β activity.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

3. Methods of Inhibiting a TGF-β in at Least One Cell

In one aspect, disclosed are methods for inhibiting TGF-β activity in at least one cell, the method comprising the step of contacting the at least one cell with an effective amount of at least one disclosed compound, or a pharmaceutically acceptable salt thereof.

In one aspect, disclosed are methods for inhibiting TGF-β activity in at least one cell, the method comprising the step of contacting the cell with an effective amount of at least one compound having a structure represented by a formula:

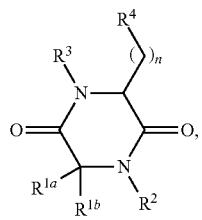

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$, or wherein $R^{1a}$ is hydrogen, $R^{1b}$ is —$CH_2Cy^3$ and $R^4$ is —$C_6H_4R^{21}$; wherein $Cy^3$ is selected from C3-C6 cycloalkyl, monocyclic heteroaryl, and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof, thereby TGF-β activity in the cell.

In one aspect, disclosed are methods for inhibiting TGF-β activity in at least one cell, the method comprising the step of contacting the cell with an effective amount of at least one compound having a structure represented by a formula:

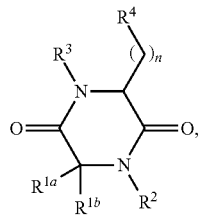

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^{31a}$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$, or a pharmaceutically acceptable salt thereof, thereby TGF-β activity in the cell.

In one aspect, disclosed are methods for inhibiting TGF-β activity in at least one cell, the method comprising the step of contacting the cell with an effective amount of at least one compound having a structure represented by a formula:

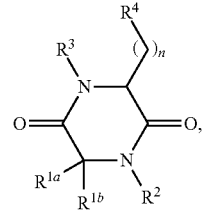

wherein n is selected from 1, 2, 3, and 4; wherein each of $R^{1a}$ and $R^{1b}$ is independently C1-C4 alkyl; or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein each of $R^2$ and $R^3$ is independently selected from hydrogen and C1-C4 alkyl; and wherein $R^4$ is selected from —$NHR^{20}$ and $Cy^1$; wherein $R^{20}$, when present, is selected from hydrogen and C1-C4 alkyl; wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and wherein $R^{21}$, when present, is selected from —$(CH_2)_qNR^{31a}R^{31b}$ and —$C(O)NR^{32a}R^{32b}$; wherein q, when present, is selected from 0 and 1; wherein each of $R^3$, $R^{31b}$, $R^{32a}$, and $R^{32b}$, when present, is independently selected from hydrogen and C1-C4 alkyl; or wherein each of $R^{1a}$ and $R^{1b}$ is hydrogen and $R^4$ is —$C_6H_4C(O)NR^{32a}R^{32b}$, provided that when n is 1 and each of $R^{1a}$ and $R^{1b}$ together comprise a 3-membered cycloalkyl then $Cy^1$, when present, is not monocyclic heteroaryl, and provided that when $R^4$ is —$NR^{20a}R^{20b}$ then each of $R^{1a}$ and $R^{1b}$ is independently C1-C4 alkyl, or a pharmaceutically acceptable salt thereof, thereby TGF-β activity in the cell.

In one aspect, disclosed are methods for inhibiting TGF-β activity in at least one cell, the method comprising the step of contacting the cell with an effective amount of at least one compound selected from:

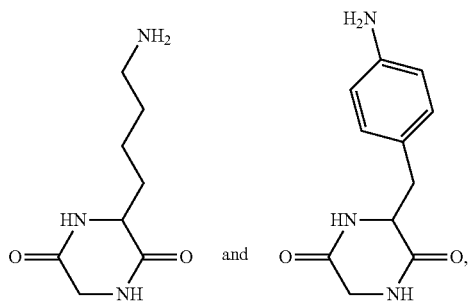 [SMILES: NCCCCC1NC(=O)CNC1=O ; Nc1ccc(CC2NC(=O)CNC2=O)cc1]

or a pharmaceutically acceptable salt thereof, thereby TGF-β activity in the cell.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of cancer in a mammal. In a still further aspect, a use relates to the manufacture of a medicament for the treatment of a fibrotic disorder in a mammal. In yet a further aspect, the use relates to the manufacture of a medicament for the treatment of immune dysfunction.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for antagonism of TGF-β activity. In one aspect, the use is characterized in that the mammal is a human. In one aspect, the use is characterized in that the disorder is a cancer or a fibrotic disorder. In one aspect, the use is characterized in that the disorder relates to immune dysfunction.

In a further aspect, the use relates to the manufacture of a medicament for the treatment of cancer in a mammal. In a still further aspect, the use relates to the manufacture of a medicament for the treatment of a fibrotic disorder in a mammal. In a still further aspect, the use relates to the manufacture of a medicament for the treatment of immune dysfunction.

In a further aspect, the use relates to antagonism of a TGF-β activity in a mammal. In a further aspect, the use relates to modulating TGF-β activity in a mammal. In a still further aspect, the use relates to modulating TGF-β activity in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of cancer in a mammal. In a further aspect, the cancer is selected from multiple myeloma and hematologic malignancy. In a further aspect, the invention relates to the use of a disclosed compound or a disclosed product in the manufacture of a medicament for the treatment of a fibrotic disorder in a mammal. In a further aspect, the fibrotic disorder is liver fibrosis, diabetic nephropathy, muscular dystrophy, or glaucoma. In a still further aspect, the use relates to the manufacture of a medicament for the treatment of immune dysfunction.

5. Manufacture of a Medicament

In one aspect, the invention relates to a method for the manufacture of a medicament for treating a disorder associated with TGF-β in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of TGF-β activity. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one disclosed compound and one or more of: (a) at least one agent known to increase TGF-β activity; (b) at least one agent known to treat cancer; (c) at least one agent known to treat a fibrotic disorder; (d) at least one agent known to treat an immune dysfunction; (e) instructions for treating a disorder associated with TGF-β dysfunction; (f) instructions for treating cancer; (g) instructions for treating a fibrotic disorder; and (h) instructions for treating an immune dysfunction.

Examples of cancers for which the compounds and compositions can be useful in treating, include, but are not limited to carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas Examples of fibrotic disorders for which the compounds and compositions can be useful in treating, include, but are not limited to, pulmonary fibrosis, diabetic nephropathy, glomerulonephritis, liver cirrhosis, proliferative vitreoretinopathy, systemic sclerosis, scleroderma, muscular dystrophy, and glaucoma.

Examples of agents known to treat cancer include, but are not limited to, alkylating agents such as busulfan, cis-platin, mitomycin C, and carboplatin; antimitotic agents such as colchicine, vinblastine, paclitaxel (e.g., TAXOL®), and docetaxel; topoisomerase I inhibitors such as camptothecin and topotecan; topoisomerase II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea, gemcitabine, capecitabine and thioguanine; antibodies such as HERCEPTIN® and RITUXAN®, as well as other known chemotherapeutics such as photofrin, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Thus, in various aspects, an agent known to treat cancer is melphalan.

Examples of agents known to treat fibrotic disorders include, but are not limited to, pirfenidone, nintedanib, a prostaglandin such as latanoprost and bimaotoprost, a beta blocker such as timolol and betaxolol, an alpha-adrenergic agonist such as apraclonidine and brimonidine, a carbonic anhydrase inhibitor such as dorzolamide and brinzolamide, a moitic or cholinergic agent such as pilocarpine, a diuretic, an angiotenisin-converting enzyme (ACE) inhibitor, an angiotensin II receptor blocker, an anti-inflammatory agent, and an anti-fibrotic agent.

Examples of agents known to treat immune dysfunction include, but are not limited to, interleukins (i.e., IL-2, IL-7, and IL-12), cytokines (i.e., interferons, G-CSF, imiquimod), chemokines (i.e., CCL3, CCL26, and CXCL7), immunomodulatory imide drugs (i.e., thalidomide, lenalidomide, pomalidomide, and apremilast), cytosine phosphate-guanosine, oligodeoxynulceotides, glucans, cytostatic drugs, glucocorticoids, and immunosuppressive antibodies.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following preparations and examples are given to enable those skilled in the art to more clearly understand and to practice the present invention. They should not be considered as limiting the scope of the invention, but merely as being illustrative and representative.

1. General Experimental Methods

The reactions were performed under a dry argon atmosphere and reaction temperatures were measured externally. Anhydrous solvents over molecular sieves were purchased from Aldrich and used as such in reactions. Purification of all compounds was carried out by utilizing a Teledyne Isco Combiflash® Rf automated chromatography machine. Universal RediSep solid sample loading pre-packed cartridges were used to absorb crude product and purified on silica RediSep Rf Gold Silica (20-40 μm spherical silica) columns using appropriate solvent gradients. Pure samples were dried overnight under high vacuum over $P_2O_5$ at 78° C. before analyses. The reactions were monitored by thin-layer chromatography (TLC) on pre-coated silica gel ($60F_{254}$) aluminium plates (0.25 mm) from E. Merck and visualized using UV light (254 nm). Pure samples were dried overnight under high vacuum over P₂O₅ at 78° C. before analyses. The HR-mass spectral data were obtained on an Agilent LC-MSTOF by electrospray ionization (ESI). ¹H NMR spectra were recorded at 400 MHz on Agilent/Varian MR-400 spectrometer in CDCl₃ or DMSO-d₆ as solvents. The chemical shifts (δ) are in ppm downfield from standard tetramethylsilane (TMS). Coupling constants (J) are reported in Hertz (Hz). Chemical shifts (δ) listed for multiplets were measured from the approximate centers, and relative integrals of peak areas agreed with those expected for the assigned structures. ESI-MS spectra were recorded on a BioTof-2 time-of-flight mass spectrometer.

2. General Synthesis of Piperazine-2,5-Diones

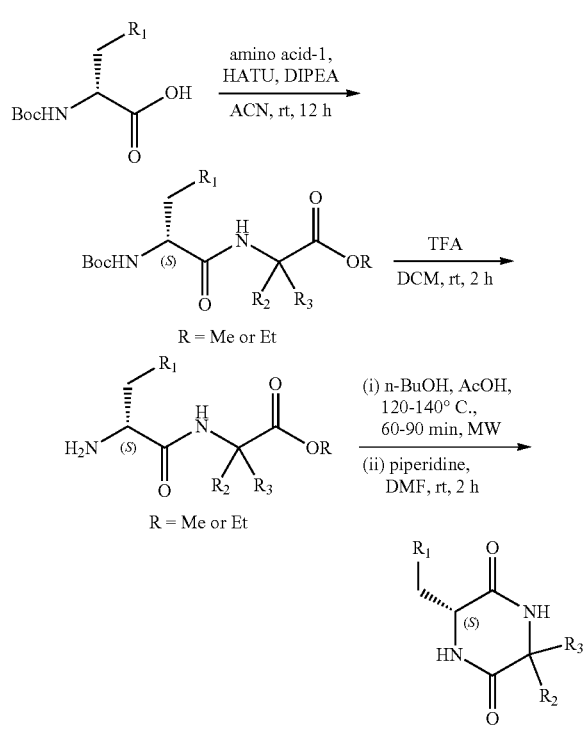

Step 1: To a stirred mixture/solution of carboxylic acid and amino acid-1 (1.1 eq.) in Acetonitrile/DMF was added DIPEA (2.5 eq.) followed by HATU (1.2 eq.) and the reaction mixture was stirred at rt for 12 h. Solvents were removed in vacuo and obtained residue was purified by Isco Teledyne Combiflash Rf200 using DCM and methanol as elutic solvents or in some cases solid crashed out, was filtered washed with diethyl ether and dried to afford the desired amide.

Step 2: To a stirred solution of amide in methylene chloride was added Trifluoroacetic acid (10 eq.) at 0° C. under inert atmosphere and the reaction mixture was stirred at rt for 2 h. Solvent was removed in vacuo and obtained residue was co-evaporated with methylene chloride twice and dried under vacuum to afford residue. This residue was dried under high vacuum and used in next step without further purification.

Step 3: To this residue in a microwave vial with a stir bar was added n-BuOH (0.15-0.2 M) followed by acetic acid (10 eq.) and the reaction mixture stirred for 5 min at room temperature. To this reaction mixture was added Toluene (0.075-0.1 M) and the reaction mixture was irradiated at 120/140° C. for 90 min. Solid crashed out, filtered, obtained solid was washed with diethyl ether and dried to afford the desired carbamate. Or in some cases solvents were removed in vacuo and the residue was purified by Isco Teledyne Combiflash Rf200 using DCM and methanol as elutic solvents to afford the desired carbamate.

Step 4: To a stirred solution of carbamate in DMF (0.5 M) was added piperidine (3 eq.) at rt under inert atmosphere and the reaction mixture was stirred at rt for 2 h. Solvents were removed in vacuo and obtained solid was washed with diethyl ether to afford the desired piperazine-2,5-dione.

A. Preparation of (S)-3-(4-Aminobutyl)Piperazine-2,5-Dione

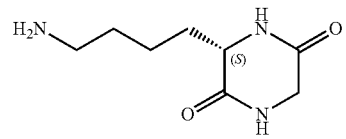

Step 1: General procedure was followed with (S)-6-((((9H-fluoren-9-yl)methoxy)carbonyl)amino)-2-((tert-butoxycarbonyl)amino)hexanoic acid and ethyl 2-aminoacetate as aminoacid-1 to obtain (S)-ethyl 2-(6-((((9H-fluoren-9-yl)methoxy)carbonyl)amino)-2-((tert-butoxycarbonyl)amino)hexanamido)acetate as a yellow solid, Yield 63.3%. ¹H NMR (400 MHz, Chloroform-d) δ 7.80-7.73 (m, 2H), 7.60 (d, J=7.5 Hz, 2H), 7.40 (dddd, J=8.2, 7.5, 1.6, 0.8 Hz, 2H), 7.30 (dd, J=1.0 Hz, 2H), 7.26 (d, 1H), 6.57 (s, 1H), 5.04-5.11 (s, 1H), 4.94 (s, 1H), 4.40 (s, 2H), 4.20 (q, J=7.2 Hz, 3H), 4.09-3.93 (m, 2H), 3.21 (d, J=6.8 Hz, 2H), 1.92-1.83 (m, 1H), 1.63-1.69 (m, 1H), 1.52-1.56 (m, 2H), 1.44 (s, 10H), 1.26 (t, J=7.1 Hz, 4H).

Step 2: General procedure was followed to (S)-ethyl 2-(6-((((9H-fluoren-9-yl)methoxy)carbonyl)amino)-2-aminohexanamido)acetate in Yield 91%. ¹H NMR (400 MHz, DMSO-d₆) δ 8.77 (t, J=5.9 Hz, 1H), 8.11 (s, 2H), 7.82 (d, J=7.5 Hz, 2H), 7.60 (d, J=7.6 Hz, 2H), 7.40-7.32 (m, 2H), 7.28 (td, J=7.4, 1.2 Hz, 2H), 7.13 (d, J=5.5 Hz, 1H), 4.35 (d, J=7.2 Hz, 1H), 4.24 (d, J=6.8 Hz, 3H), 4.14 (s, 3H), 2.91 (d, J=6.8 Hz, 2H), 1.66 (s, 2H), 1.34 (d, J=6.9 Hz, 2H), 1.27-1.3 (m, 1H), 1.21-1.26 (m, 2H), 1.11 (t, J=7.1 Hz, 3H).

Step 3: General procedure was followed to obtain (S)-(9H-fluoren-9-yl)methyl (4-(3,6-dioxopiperazin-2-yl)butyl) carbamate as yellow color solid, Yield 37%, ¹H NMR (400 MHz, Methanol-d₄) δ 7.79 (d, J=7.5 Hz, 2H), 7.64 (d, J=7.6 Hz, 2H), 7.38 (t, J=7.4 Hz, 2H), 7.30 (td, J=7.4, 1.2 Hz, 2H), 4.35 (d, J=6.9 Hz, 2H), 4.18 (q, J=6.9 Hz, 1H), 4.01-3.80 (m, 3H), 3.12 (q, J=6.9, 6.5 Hz, 2H), 1.85 (dq, J=19.8, 7.0, 6.6 Hz, 1H), 1.51 (q, J=6.9, 6.4 Hz, 2H), 1.42 (s, 1H), 1.31-1.17 (m, 1H), 0.87-0.96 (m, 1H). MS m/z 408 [M+H]⁺.

Step 4: General procedure was followed to obtain (S)-3-(4-aminobutyl)piperazine-2,5-dione as a yellow color solid, Yield 88%, ¹H NMR (400 MHz, DMSO-d₆) δ 8.16 (s, 1H), 7.96 (s, 1H), 3.78 (d, J=17.4 Hz, 1H), 3.73 (s, 1H), 3.66 (dd, J=17.0, 2.1 Hz, 1H), 2.94-2.86 (m, 1H), 2.56 (t, J=6.5 Hz, 1H), 1.66 (p, J=6.2 Hz, 2H), 1.38-1.26 (m, 4H).

b. Preparation of (S)-6-(4-Aminobutyl)-3,3-Dimethylpiperazine-2,5-Dione

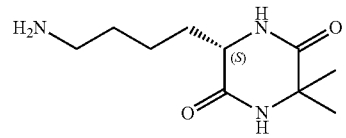

Step 1: General procedure was followed with (S)-6-((((9H-fluoren-9-yl)methoxy)carbonyl)amino)-2-((tert-butoxycarbonyl)amino)hexanoic acid and ethyl 2-amino-2-methylpropanoate as amino acid-1 to obtain (S)-ethyl 2-(6-((((9H-fluoren-9-yl)methoxy)carbonyl)amino)-2-((tert-butoxycarbonyl)amino)hexanamido)-2-methylpropanoate as a off-white solid Yield-85%. $^1$H NMR (400 MHz, DMSO-$d_6$) δ 8.09 (s, 1H), 7.91-7.84 (m, 2H), 7.66 (d, J=7.5 Hz, 2H), 7.43-7.36 (m, 2H), 7.31 (td, J=7.4, 1.1 Hz, 2H), 7.24 (t, J=5.7 Hz, 1H), 6.64 (d, J=8.5 Hz, 1H), 4.27 (d, J=6.9 Hz, 2H), 4.18 (t, J=6.9 Hz, 1H), 3.96 (q, J=7.0 Hz, 2H), 3.86 (d, J=7.1 Hz, 1H), 2.93 (d, J=6.2 Hz, 2H), 1.50 (s, 2H), 1.38-1.33 (m, 11H), 1.31 (s, 3H), 1.29 (s, 3H), 1.23 (d, J=10.3 Hz, 2H), 1.09 (t, J=7.1 Hz, 3H). MS m/z 582 [M+H]$^+$.

Step 2: General procedure was followed to obtain (S)-ethyl 2-(6-((((9H-fluoren-9-yl)methoxy)carbonyl)amino)-2-aminohexanamido)-2-methylpropanoate, TFA as a sticky solid, Yield-62.5%, $^1$H NMR (400 MHz, DMSO-$d_6$) δ 8.68 (s, 1H), 8.03 (s, 2H), 7.88 (dt, J=7.6, 1.0 Hz, 2H), 7.66 (d, J=7.5 Hz, 2H), 7.45-7.38 (m, 2H), 7.31 (td, J=7.4, 1.2 Hz, 2H), 7.22 (t, J=5.6 Hz, 1H), 4.29 (d, J=6.8 Hz, 2H), 4.19 (t, J=6.7 Hz, 1H), 4.02 (qd, J=7.1, 2.0 Hz, 2H), 3.69-3.63 (1, 1H), 3.13 (qd, J=7.3, 4.2 Hz, 1H), 2.95 (q, J=6.6 Hz, 1H), 1.67 (q, J=7.3 Hz, 2H), 1.39 (s, 3H), 1.34 (s, 3H), 1.30 (d, J=7.4 Hz, 2H), 1.22 (d, J=7.3 Hz, 2H), 1.13 (t, J=7.1 Hz, 3H). MS m/z 482 [M+H]$^+$.

Step 3: General procedure was followed to obtain (S)-(9H-fluoren-9-yl)methyl (4-(5,5-dimethyl-3,6-dioxopiperazin-2-yl)butyl)carbamate as a white solid, Yield-22%, $^1$H NMR (400 MHz, DMSO-$d_6$) δ 8.17 (s, 1H), 7.96 (s, 1H), 7.89-7.85 (m, 2H), 7.66 (d, J=7.6 Hz, 2H), 7.43-7.36 (m, 2H), 7.31 (td, J=7.4, 1.2 Hz, 2H), 7.25 (t, J=5.7 Hz, 1H), 4.29-4.24 (m, 2H), 4.19 (t, J=6.8 Hz, 1H), 3.87 (t, J=4.8 Hz, 1H), 3.15 (d, J=4.9 Hz, 1H), 3.00-2.87 (m, 1H), 1.66 (s, 2H), 1.41-1.31 (m, 2H), 1.28 (d, J=2.1 Hz, 7H), 1.19-1.25 (m, 1H). MS m/z 436 [M+H]$^+$.

Step 4: General procedure was followed to obtain (S)-6-(4-aminobutyl)-3,3-dimethylpiperazine-2,5-dione as a white solid, Yield-84%, $^1$H NMR (400 MHz, Methanol-$d_4$) δ 4.07 (t, J=5.1 Hz, 1H), 2.80 (t, J=7.3 Hz, 2H), 1.97-1.74 (m, 2H), 1.61 (q, J=7.7 Hz, 2H), 1.54-1.45 (m, 1H), 1.44 (d, J=2.2 Hz, 6H), 1.43-1.34 (m, 1H). HRMS m/z calcd for $C_{10}H_{19}N_3O_2$ [M+H]$^+$: 213.1477, found: 213.1473.

c. Preparation of (S)-3-(4-Aminobenzyl)Piperazine-2,5-Dione

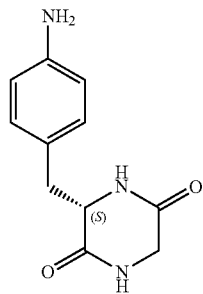

Step 1: General procedure was followed with (S)-3-(4-((((9H-fluoren-9-yl)methoxy)carbonyl)amino)phenyl)-2-((tert-butoxycarbonyl)amino)propanoic acid and ethyl 2-aminoacetate, HCl as amino acid-1 to obtain (S)-ethyl 2-(3-(4-((((9H-fluoren-9-yl)methoxy)carbonyl)amino)phenyl)-2-((tert-butoxycarbonyl)amino)propanamido)acetate as a white solid, Yield-74.3%. 1H NMR (400 MHz, DMSO-d6) δ 9.59 (s, 1H), 8.32 (t, J=5.9 Hz, 1H), 7.89 (dt, J=1.0, 7.5 Hz, 2H), 7.73 (d, J=7.4 Hz, 2H), 7.48-7.37 (m, 2H), 7.33 (td, J=1.2, 7.5 Hz, 3H), 7.13 (d, J=8.2 Hz, 2H), 6.85 (d, J=8.7 Hz, 1H), 4.44 (d, J=6.7 Hz, 2H), 4.28 (t, J=6.6 Hz, 1H), 4.07 (q, J=7.1 Hz, 3H), 3.83 (qd, J=5.9, 17.5 Hz, 2H), 2.90 (dd, J=4.1, 13.8 Hz, 1H), 2.68-2.56 (m, 1H), 1.28 (s, 9H), 1.17 (t, J=7.1 Hz, 3H). MS m z 488 [M−100 (for Boc)+1], 610 [M+Na]$^+$.

Step 2: General procedure was followed to obtain (S)-ethyl 2-(3-(4-((((9H-fluoren-9-yl)methoxy)carbonyl)amino)phenyl)-2-aminopropanamido)acetate, AcO— as a sticky solid, Yield-89%, $^1$H NMR (400 MHz, DMSO-$d_6$) δ 9.69 (s, 1H), 8.89 (t, J=5.9 Hz, 1H), 8.08 (s, 2H), 7.89 (d, J=7.5 Hz, 2H), 7.72 (d, J=7.4 Hz, 2H), 7.45-7.28 (m, 6H), 7.15 (d, J=8.1 Hz, 2H), 4.47 (d, J=6.7 Hz, 2H), 4.29 (t, J=6.5 Hz, 1H), 4.10 (q, J=7.1 Hz, 2H), 3.99 (d, J=7.8 Hz, 1H), 3.92 (dd, J=5.8, 3.8 Hz, 2H), 3.04 (dd, J=14.3, 5.2 Hz, 1H), 2.86 (dd, J=14.3, 7.8 Hz, 1H), 1.18 (t, J=7.1 Hz, 3H). MS m/z 488 [M+H]$^+$.

Step 3: General procedure was followed to obtain (S)-(9H-fluoren-9-yl)methyl(4-((3,6-dioxopiperazin-2-yl)methyl)phenyl)carbamate as a white solid, Yield-63.3%, $^1$H NMR (400 MHz, DMSO-$d_6$) δ 9.66 (s, 1H), 8.10 (d, J=2.7 Hz, 1H), 7.93-7.83 (m, 3H), 7.73 (d, J=7.5 Hz, 2H), 7.46-7.38 (m, 2H), 7.33 (td, J=7.5, 1.2 Hz, 4H), 7.03 (d, J=8.2 Hz, 2H), 4.45 (d, J=6.7 Hz, 2H), 4.29 (t, J=6.6 Hz, 1H), 4.02-3.96 (m, 1H), 3.37-3.33 (m, 1H), 3.01 (dd, J=13.6, 4.4 Hz, 1H), 2.84-2.72 (m, 2H). MS m/z 442 [M+H]$^+$.

Step 4: General procedure was followed to obtain (S)-3-(4-aminobenzyl)piperazine-2,5-dione as a light yellow solid, Yield-72.6%, 1H NMR (400 MHz, Methanol-d4) δ 6.99-6.86 (m, 2H), 6.69-6.61 (m, 2H), 4.16-4.05 (m, 1H), 3.39 (dd, J=17.6, 0.7 Hz, 1H), 3.11 (dd, J=13.9, 3.8 Hz, 1H), 2.89-2.73 (m, 2H), 2.65 (dd, J=17.6, 1.1 Hz, 1H). HRMS m/z calcd for $C_{11}H_{13}N_3O_2$[M+H]$^+$: 219.1008, found: 219.1004.

d. Preparation of (S)-6-(4-Aminobenzyl)-3,3-Dimethylpiperazine-2,5-Dione

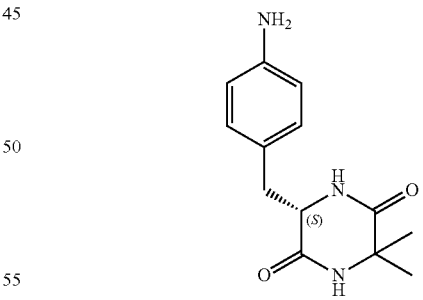

Step 1: General procedure was followed with (S)-3-(4-((((9H-fluoren-9-yl)methoxy)carbonyl)amino)phenyl)-2-((tert-butoxycarbonyl)amino)propanoic acid and methyl 2-amino-2-methylpropanoate, HCl as amino acid to obtain (S)-ethyl 2-(3-(4-((((9H-fluoren-9-yl)methoxy)carbonyl)amino)phenyl)-2-((tert-butoxycarbonyl)amino)propanamido)-2-methylpropanoate as a white fluffy solid, Yield-82%, 1H NMR (400 MHz, DMSO-d6) δ 9.60 (s, 1H), 8.19 (s, 1H), 7.89 (dt, J=7.5, 1.0 Hz, 2H), 7.73 (d, J=7.4 Hz, 2H), 7.41 (tdd, J=7.5, 1.2, 0.6 Hz, 2H), 7.33 (td, J=7.4, 1.2 Hz, 4H), 7.13 (d, J=8.0 Hz, 2H), 6.72 (d, J=8.9 Hz, 1H), 4.44 (d, J=6.7 Hz, 2H), 4.28 (t, J=6.7 Hz, 1H), 4.12-4.02 (m, 1H), 3.98 (q, J=7.0 Hz, 2H), 3.15 (d, J=5.2 Hz, 1H), 2.81 (dd, J=13.8, 4.6 Hz, 1H), 2.62 (dd, J=13.9, 10.2 Hz, 1H), 1.31 (d, J=12.3 Hz, 6H), 1.28 (s, 8H), 1.11 (t, J=7.1 Hz, 3H). MS m/z 516 [(M−100) for Boc+H]⁺.

Step 2: General procedure was followed to obtain (S)-ethyl 2-(3-(4-((((9H-fluoren-9-yl)methoxy)carbonyl)amino)phenyl)-2-aminopropanamido)-2-methylpropanoate, TFA as a yield over two steps-49%; 1H NMR (400 MHz, DMSO-d6) δ 9.69 (s, 1H), 8.67 (s, 1H), 8.06 (d, J=5.4 Hz, 2H), 7.90 (dt, J=7.7, 1.0 Hz, 2H), 7.74-7.68 (m, 2H), 7.44-7.38 (m, 4H), 7.33 (td, J=7.4, 1.2 Hz, 2H), 7.16 (d, J=8.3 Hz, 2H), 4.47 (d, J=6.6 Hz, 2H), 4.29 (t, J=6.6 Hz, 1H), 4.04 (q, J=7.1 Hz, 2H), 3.90 (d, J=6.7 Hz, 1H), 3.01 (dd, J=14.1, 5.7 Hz, 1H), 2.84 (dd, J=14.2, 8.0 Hz, 1H), 1.36 (s, 3H), 1.30 (s, 3H), 1.15 (t, J=7.1 Hz, 3H).

Step 3: General procedure was followed to obtain (S)-(9H-fluoren-9-yl)methyl(4-((5,5-dimethyl-3,6-dioxopiperazin-2-yl)methyl)phenyl)carbamate. 1H NMR (400 MHz, DMSO-d6) δ 9.60 (s, 1H), 8.07 (s, 1H), 7.99 (d, J=1.9 Hz, 1H), 7.89 (dt, J=7.5, 1.0 Hz, 2H), 7.72 (d, J=7.4 Hz, 2H), 7.44-7.37 (m, 2H), 7.33 (td, J=7.5, 1.2 Hz, 4H), 7.03 (d, J=8.3 Hz, 2H), 4.44 (d, J=6.7 Hz, 2H), 4.28 (t, J=6.7 Hz, 1H), 4.14 (s, 1H), 3.06 (dd, J=13.6, 3.6 Hz, 1H), 2.77 (dd, J=13.6, 4.9 Hz, 1H), 1.16 (s, 3H), 0.53 (s, 3H). MS m/z 470 [M+H]⁺.

Step 4: General procedure was followed to obtain (S)-6-(4-aminobenzyl)-3,3-dimethylpiperazine-2,5-dione as a white solid, Yield-62%, 1H NMR (400 MHz, DMSO-d6) δ 8.00 (s, 1H), 7.89-7.84 (m, 1H), 6.78 (d, J=8.0 Hz, 2H), 6.42 (d, J=8.0 Hz, 2H), 4.84 (s, 2H), 4.04 (s, 1H), 2.94 (d, J=13.7, 3.5 Hz, 1H), 2.64 (dd, J=13.5, 4.8 Hz, 1H), 1.15 (s, 3H), 0.56 (s, 3H). HRMS m/z calcd for $C_{13}H_{17}N_3O_2$ [M+H]⁺: 247.1321, found: 247.1327.

e. Preparation of (S)-6-(3-(Aminomethyl)Benzyl)-3,3-Dimethylpiperazine-2,5-Dione

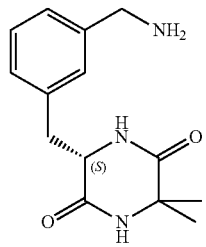

Step 1: General procedure was followed with (S)-3-(3-(((((9H-fluoren-9-yl)methoxy)carbonyl)amino)methyl)phenyl)-2-((tert-butoxycarbonyl)amino)propanoic acid and methyl 2-amino-2-methylpropanoate, HCl to obtain (S)-ethyl2-(3-(3-(((((9H-fluoren-9-1)methoxy)carbonyl)amino)methyl)phenyl)-2-((tert-butoxycarbonyl)amino)propanamido)-2-methylpropanoate as a white solid, Yield-68%, ¹H NMR (400 MHz, DMSO-d₆) δ 8.20 (s, 1H), 7.87 (dd, J=7.5, 1.2 Hz, 2H), 7.83-7.74 (m, 1H), 7.68 (d, J=7.4 Hz, 2H), 7.40 (td, J=7.4, 1.1 Hz, 2H), 7.37-7.26 (m, 2H), 7.18 (d, J=7.7 Hz, 1H), 7.13 (s, 2H), 7.03 (d, J=7.6 Hz, 1H), 6.77 (d, J=8.8 Hz, 1H), 4.31 (d, J=7.5 Hz, 2H), 4.21 (t, J=6.9 Hz, 1H), 4.14 (d, J=5.9 Hz, 3H), 3.98 (dt, J=14.2, 6.6 Hz, 3H), 2.95-2.79 (m, 1H), 1.31 (s, 3H), 1.28 (s, 9H), 1.23 (s, 3H), 1.10 (dd, J=8.0, 6.3 Hz, 3H). MS m/z 630 [M+H]⁺, 530 [(M−100) for Boc+H]⁺.

Step 2: General procedure was followed to obtain (S)-ethyl 2-(3-(3-(((((9H-fluoren-9-yl)methoxy)carbonyl)amino)methyl)phenyl)-2-aminopropanamido)-2-methylpropanoate as a sticky solid, ¹H NMR (400 MHz, DMSO-d₆) δ 8.78 (s, 1H), 8.21 (s, 2H), 7.98 (d, J=7.7 Hz, 2H), 7.88 (t, J=6.1 Hz, 1H), 7.78 (d, J=7.6 Hz, 2H), 7.51 (t, J=7.5 Hz, 2H), 7.46-7.34 (m, 3H), 7.29-7.19 (m, 3H), 4.44 (d, J=7.2 Hz, 2H), 4.30 (dd, J=23.8, 6.4 Hz, 3H), 4.13 (q, J=7.0 Hz, 2H), 4.05 (s, 1H), 3.14 (dd, J=14.1, 5.9 Hz, 1H), 3.00 (dd, J=14.0, 7.7 Hz, 1H), 1.45 (s, 3H), 1.38 (s, 3H), 1.29-1.20 (m, 3H). MS m/z 530 [M+H]⁺.

Step 3: General procedure was followed to obtain (S)-(9H-fluoren-9-yl)methyl 3-((5,5-dimethyl-3,6-dioxopiperazin-2-yl)methyl)benzylcarbamate as a white solid, Yield-54.8%, 1H NMR (400 MHz, DMSO-d6) δ 8.07 (s, 1H), 7.97 (s, 1H), 7.86 (d, J=7.5 Hz, 2H), 7.75 (t, J=6.1 Hz, 1H), 7.68 (d, J=7.4 Hz, 2H), 7.46-7.33 (m, 2H), 7.33-7.22 (m, 2H), 7.22-7.11 (m, 1H), 7.10-6.97 (m, 3H), 4.30 (d, J=6.9 Hz, 2H), 4.26-4.16 (m, 2H), 4.10 (d, J=6.1 Hz, 2H), 3.08 (dd, J=13.5, 3.9 Hz, 1H), 2.85 (dd, J=13.5, 4.9 Hz, 1H), 1.15 (s, 3H), 0.54 (s, 3H). MS m/z 484 [M+H]⁺.

Step 4: General procedure was followed to obtain (S)-6-(3-(aminomethyl)benzyl)-3,3-dimethylpiperazine-2,5-dione as a white solid, Yield-76%, 1H NMR (400 MHz, DMSO-d6) δ 8.06 (s, 1H), 7.98 (d, J=2.0 Hz, 1H), 7.17 (dd, J=5.9, 0.9 Hz, 2H), 7.09 (s, 1H), 7.06-6.94 (m, 1H), 4.16 (ddd, J=4.9, 3.7, 1.9 Hz, 1H), 3.63 (s, 2H), 3.09 (dd, J=13.4, 3.8 Hz, 1H), 2.89-2.78 (m, 1H), 1.14 (s, 3H), 0.47 (s, 3H). HRMS m/z calcd for $C_{14}H_{19}N_3O_2$ [M+H]⁺: 261.1477, found: 261.1485.

f. Preparation of (S)-8-(4-Aminobutyl)-6,9-Diazaspiro[4.5]Decane-7,10-Dione

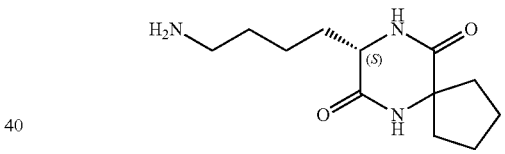

Step 1: General procedure was followed with (S)-6-(((((9H-fluoren-9-yl)methoxy)carbonyl)amino)-2-((tert-butoxycarbonyl)amino)hexanoic acid and methyl 1-aminocyclopentanecarboxylate, HCl to obtain (S)-methyl1-(6-(((((9H-fluoren-9-yl)methoxy)carbonyl)amino)-2-((tert-butoxycarbonyl)amino)hexanamido)cyclopentanecarboxylate as a white solid, Yield-52%, ¹H NMR (400 MHz, DMSO-d₆) δ 8.12 (s, 1H), 7.86 (dt, J=7.7, 1.0 Hz, 2H), 7.65 (d, J=7.4 Hz, 2H), 7.45-7.35 (m, 2H), 7.35-7.27 (m, 2H), 7.22 (t, J=5.7 Hz, 1H), 6.60 (d, J=8.4 Hz, 1H), 4.26 (d, J=6.9 Hz, 2H), 4.17 (t, J=6.8 Hz, 1H), 3.85 (d, J=7.2 Hz, 1H), 3.50 (s, 3H), 2.93 (d, J=7.0 Hz, 2H), 1.98 (dd, J=21.8, 12.3 Hz, 2H), 1.82 (d, J=13.0 Hz, 2H), 1.60-1.62 (m, 4H), 1.44 (s, 2H), 1.37-1.30 (m, 11H), 1.20-1.24 (m, 2H). MS m/z 594 [M+H]⁺.

Step 2: General procedure was followed to obtain (S)-methyl 1-(6-(((((9H-fluoren-9-yl)methoxy)carbonyl)amino)-2-aminohexanamido)cyclopentanecarboxylate in Yield-72% (Over step 2 and 3), ¹H NMR (400 MHz, DMSO-d₆) δ 8.74 (s, 1H), 8.03 (s, 1H), 7.87 (dt, J=7.6, 1.0 Hz, 2H), 7.68-7.61 (m, 2H), 7.42-7.36 (m, 2H), 7.31 (td, J=7.4, 1.2 Hz, 2H), 7.23 (t, J=5.7 Hz, 1H), 4.28 (d, J=6.8 Hz, 2H), 4.18 (t, J=6.7 Hz, 1H), 3.54 (s, 3H), 2.95 (q, J=6.7 Hz, 2H), 1.93-1.79 (m, 2H), 1.66 (d, J=15.6 Hz, 6H), 1.43-1.36 (m, 2H), 1.34-1.27 (m, 2H), 1.19-1.03 (m, 2H). MS m/z 494 [M+H]+

Step 3: General procedure was followed to obtain (S)-(9H-fluoren-9-yl)methyl (4-(7,10-dioxo-6,9-diazaspiro[4.5]

decan-8-yl)butyl)carbamate as a white solid, 1H NMR (400 MHz, DMSO-d6) δ 8.28 (s, 1H), 7.99 (d, J=2.0 Hz, 1H), 7.87 (dt, J=7.6, 0.9 Hz, 2H), 7.66 (d, J=7.4 Hz, 2H), 7.40 (ddd, J=8.5, 7.4, 1.0 Hz, 2H), 7.31 (td, J=7.4, 1.2 Hz, 2H), 7.24 (t, J=5.7 Hz, 1H), 4.27 (d, J=6.9 Hz, 2H), 4.19 (t, J=6.9 Hz, 1H), 3.86-3.78 (m, 1H), 2.95 (q, J=6.5 Hz, 2H), 2.04 (t, J=5.7 Hz, 2H), 1.64 (dt, J=14.1, 8.9 Hz, 8H), 1.40-1.32 (m, 2H), 1.12 (s, 2H). MS m/z 462 [M+H]⁺.

Step 4: General procedure was followed to obtain (S)-8-(4-aminobutyl)-6,9-diazaspiro[4.5]decane-7,10-dione as a white solid, Yield-77%, 1H NMR (400 MHz, Deuterium Oxide) δ 4.06 (t, J=5.3 Hz, 1H), 2.85 (t, J=7.7 Hz, 2H), 2.18-2.03 (m, 2H), 1.84-1.64 (m, 8H), 1.64-1.48 (m, 2H), 1.41-1.18 (m, 2H). HRMS m/z calcd for $C_{12}H_{21}N_3O_2$ [M+H]⁺: 239.1634, found: 239.1635.

g. Preparation of (S)-7-(4-Aminobutyl)-5,8-Diazaspiro[3.5]Nonane-6,9-Dione

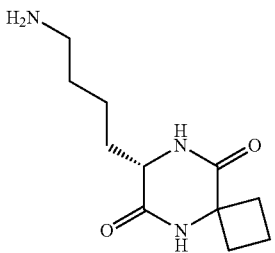

Step 1: General procedure was followed with (S)-6-((((9H-fluoren-9-yl)methoxy)carbonyl)amino)-2-((tert-butoxycarbonyl)amino)hexanoic acid and methyl 1-aminocyclobutanecarboxylate to obtain (S)-methyl 1-(6-((((9H-fluoren-9-yl)methoxy)carbonyl)amino)-2-((tert-butoxycarbonyl)amino)hexanamido)cyclobutanecarboxylate as a white solid, Yield-55%, ¹H NMR (400 MHz, DMSO-d₆) δ 8.55 (s, 1H), 7.86 (dt, J=7.6, 1.0 Hz, 2H), 7.65 (d, J=7.4 Hz, 2H), 7.43-7.35 (m, 2H), 7.35-7.27 (m, 2H), 7.23 (t, J=5.6 Hz, 1H), 6.63 (d, J=8.2 Hz, 1H), 4.26 (d, J=6.9 Hz, 2H), 4.17 (t, J=6.9 Hz, 1H), 3.87 (q, J=7.5 Hz, 1H), 3.54 (s, 3H), 2.94 (t, J=6.6 Hz, 2H), 2.66 (s, 2H), 2.39 (d, J=14.2 Hz, 1H), 2.17-2.00 (m, 2H), 1.93-1.78 (m, 2H), 1.48 (dt, J=22.6, 7.6 Hz, 1H), 1.34 (s, 10H), 1.23 (dd, J=6.6, 5.4 Hz, 3H). MS m/z 580 [M+H]⁺.

Step 2: General procedure was followed to obtain (S)-methyl 1-(6-((((9H-fluoren-9-yl)methoxy)carbonyl)amino)-2-aminohexanamido)cyclobutanecarboxylate in Yield-68% (Over step 2 and 3), 1H NMR (400 MHz, DMSO-d6) δ 9.11 (s, 1H), 8.04 (d, J=5.1 Hz, 2H), 7.87 (d, J=7.5 Hz, 2H), 7.65 (d, J=7.5 Hz, 2H), 7.42-7.36 (m, 2H), 7.31 (td, J=7.4, 1.2 Hz, 2H), 7.22 (t, J=5.7 Hz, 1H), 4.28 (d, J=6.8 Hz, 2H), 4.18 (t, J=6.8 Hz, 1H), 3.75-3.65 (m, 1H), 3.58 (s, 3H), 2.95 (q, J=6.6 Hz, 2H), 2.67 (s, 2H), 2.21-2.03 (m, 2H), 1.97-1.83 (m, 2H), 1.70 (q, J=7.4 Hz, 2H), 1.39 (q, J=7.1 Hz, 1H), 1.32-1.18 (m, 3H). MS m z 480 [M+H]⁺.

Step 3: General procedure was followed to obtain (S)-(9H-fluoren-9-yl)methyl (4-(6,9-dioxo-5,8-diazaspiro[3.5]nonan-7-yl)butyl)carbamate as a white solid, Yield-77%, ¹H NMR (400 MHz, DMSO-d₆) δ 8.63 (s, 1H), 8.00 (d, J=2.6 Hz, 1H), 7.87 (dt, J=7.6, 0.9 Hz, 2H), 7.66 (d, J=7.4 Hz, 2H), 7.43-7.35 (m, 2H), 7.32 (dd, J=7.4, 1.2 Hz, 2H), 7.23 (t, J=5.7 Hz, 1H), 4.26 (d, J=6.9 Hz, 2H), 4.18 (t, J=6.9 Hz, 1H), 3.69 (td, J=5.5, 2.5 Hz, 1H), 2.94 (q, J=6.5 Hz, 2H), 2.5-2.52 (m, 1H), 2.44 (s, 1H), 2.13 (td, J=11.4, 10.7, 8.9 Hz, 2H), 1.91-1.65 (m, 2H), 1.57 (d, J=6.6 Hz, 2H), 1.35 (q, J=7.0 Hz, 2H), 1.28-1.03 (m, 2H). MS m/z 470 [M+Na]⁺.

Step 4: General procedure was followed to obtain (S)-7-(4-aminobutyl)-5,8-diazaspiro[3.5]nonane-6,9-dione as a white solid, Yield-63.6%, ¹H NMR (400 MHz, Deuterium Oxide) δ 3.96 (t, J=5.4 Hz, 1H), 2.73 (t, J=7.6 Hz, 2H), 2.65-2.43 (m, 2H), 2.30-2.11 (m, 2H), 1.82 (pd, J=8.7, 4.3 Hz, 2H), 1.73-1.57 (m, 2H), 1.48 (p, J=7.6 Hz, 2H), 1.36-1.09 (m, 2H). HRMS m/z calcd for $C_{11}H_{19}N_3O_2$ [M+H]⁺: 225.1480, found: 225.1477.

h. Preparation of (S)-7-(4-Aminobenzyl)-5,8-Diazaspiro[3.5]Nonane-6,9-Dione

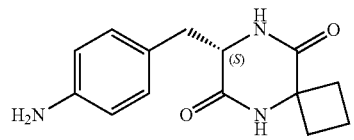

Step 1: General procedure was followed with (S)-3-(4-((((9H-fluoren-9-yl)methoxy)carbonyl)amino)phenyl)-2-((tert-butoxycarbonyl)amino)propanoic acid and methyl 1-aminocyclobutanecarboxylate to obtain (S)-methyl 1-(3-(4-((((9H-fluoren-9-yl)methoxy)carbonyl)amino)phenyl)-2-((tert-butoxycarbonyl)amino)propanamido)cyclobutanecarboxylate as an off-white solid, Yield-55%, ¹H NMR (400 MHz, DMSO-d₆) δ 9.59 (s, 1H), 8.63 (s, 1H), 8.13 (s, 1H), 7.89 (dt, J=7.7, 1.1 Hz, 2H), 7.72 (d, J=7.5 Hz, 2H), 7.40 (tdd, J=7.5, 1.2, 0.6 Hz, 2H), 7.32 (td, J=7.5, 1.2 Hz, 3H), 7.11 (d, J=8.1 Hz, 2H), 6.71 (d, J=8.7 Hz, 1H), 4.44 (d, J=6.7 Hz, 2H), 4.28 (t, J=6.7 Hz, 1H), 4.13-4.02 (m, 1H), 3.66-3.58 (m, 2H), 3.56 (d, J=11.0 Hz, 3H), 3.18-3.06 (m, 2H), 2.82 (dd, J=13.8, 5.2 Hz, 1H), 2.67-2.59 (m, 1H), 2.06 (q, J=9.0 Hz, 2H), 1.84 (s, 1H), 1.29 (s, 9H). MS m/z 514 [(M−100) for Boc+H]⁺.

Steps 2 and 3: General procedure was followed to obtain (S)-methyl 1-(3-(4-((((9H-fluoren-9-yl)methoxy)carbonyl)amino)phenyl)-2-aminopropanamido)cyclobutanecarboxylate, TFA in Yield-63.6% (Over step 2 and 3), ¹H NMR (400 MHz, DMSO-d₆) δ 9.58 (s, 1H), 8.53 (s, 1H), 7.95 (d, J=2.5 Hz, 1H), 7.88 (dt, J=7.6, 0.9 Hz, 2H), 7.72 (d, J=7.4 Hz, 2H), 7.40 (tt, J=7.4, 1.0 Hz, 2H), 7.32 (td, J=7.4, 1.2 Hz, 4H), 6.98 (d, J=8.2 Hz, 2H), 4.43 (d, J=6.7 Hz, 2H), 4.27 (t, J=6.6 Hz, 1H), 4.01 (td, J=4.6, 2.4 Hz, 1H), 2.95 (dd, J=13.6, 4.1 Hz, 1H), 2.74 (dd, J=13.5, 4.9 Hz, 1H), 2.36 (ddd, J=12.4, 8.6, 4.3 Hz, 1H), 1.98 (q, J=9.9, 8.6 Hz, 1H), 1.67-1.54 (m, 1H), 1.52-1.40 (m, 3H). MS m/z 482[M+H]⁺.

Step 4: General procedure was followed to obtain (S)-7-(4-aminobenzyl)-5,8-diazaspiro[3.5]nonane-6,9-dione as a white solid, Yield-46.4%, 1HNMR (400 MHz, Methanol-d₄) δ 6.94-6.86 (m, 2H), 6.69-6.60 (m, 2H), 4.13 (t, J=4.2 Hz, 1H), 3.06 (dd, J=13.9, 3.9 Hz, 1H), 2.78 (dd, J=13.9, 4.7 Hz, 1H), 2.57 (ddt, J=15.6, 8.9, 4.0 Hz, 1H), 2.14-2.01 (m, 2H), 1.81-1.72 (m, 1H), 1.71-1.60 (m, 2H), 1.60-1.46 (m, 1H). HRMS m/z calcd for $C_{14}H_{17}N_3O_2$ [M+H]⁺: 259.1321, found: 259.1322.

i. Preparation of (S)-8-(4-Aminobenzyl)-6,9-Diazaspiro[4.5]Decane-7,10-Dione

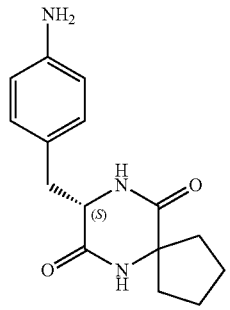

Step 1: General procedure was followed with (S)-6-((((9H-fluoren-9-yl)methoxy)carbonyl)amino)-2-((tert-butoxycarbonyl)amino)hexanoic acid and methyl 1-aminocyclopentanecarboxylate, HCl to obtain (S)-methyl 1-(6-((((9H-fluoren-9-yl)methoxy)carbonyl)amino)-2-((tert-butoxycarbonyl)amino)hexanamido)cyclopentanecarboxylate as an off-white solid, Yield-52%, $^1$H NMR (400 MHz, DMSO-d$_6$) δ 8.14 (s, 1H), 7.87 (dt, J=7.6, 1.0 Hz, 2H), 7.66 (d, J=7.4 Hz, 2H), 7.47-7.36 (m, 2H), 7.34-7.27 (m, 2H), 7.24 (t, J=5.7 Hz, 1H), 6.62 (d, J=8.3 Hz, 1H), 4.26 (d, J=6.9 Hz, 2H), 4.18 (t, J=6.8 Hz, 1H), 3.89-3.82 (m, 1H), 3.50 (s, 3H), 2.97-2.87 (m, 2H), 2.02-1.91 (m, 2H), 1.82 (dd, J=10.5, 4.2 Hz, 2H), 1.61 (d, J=5.1 Hz, 5H), 1.50-1.37 (m, 3H), 1.30-1.33 (s, 11H). MS m/z 594 [M+H]$^+$.

Step 2: General procedure was followed to obtain (S)-methyl 1-(6-((((9H-fluoren-9-yl)methoxy)carbonyl)amino)-2-aminohexanamido)cyclopentanecarboxylate in Yield-72% (Over step 2 and 3), $^1$H NMR (400 MHz, DMSO-d$_6$) δ 8.74 (s, 1H), 8.03 (s, 2H), 7.87 (dt, J=7.6, 1.0 Hz, 2H), 7.70-7.61 (m, 2H), 7.46-7.35 (m, 2H), 7.31 (td, J=7.4, 1.2 Hz, 2H), 7.23 (t, J=5.7 Hz, 1H), 4.28 (d, J=6.8 Hz, 2H), 4.18 (t, J=6.7 Hz, 2H), 3.54 (s, 3H), 2.95 (q, J=6.6 Hz, 2H), 1.93-1.77 (m, 2H), 1.64 (s, 6H), 1.44-1.27 (m, 4H), 1.20-1.02 (m, 2H). MS m/z 494 [M+H]$^+$.

Step 3: General procedure was followed to obtain (S)-(9H-fluoren-9-yl)methyl (4-(7,10-dioxo-6,9-diazaspiro[4.5]decan-8-yl)butyl)carbamate as a white solid, 1H NMR (400 MHz, DMSO-d6) δ 8.28 (s, 1H), 7.99 (d, J=2.0 Hz, 1H), 7.87 (dt, J=7.6, 0.9 Hz, 2H), 7.66 (d, J=7.4 Hz, 2H), 7.40 (ddd, J=8.5, 7.4, 1.0 Hz, 2H), 7.31 (td, J=7.4, 1.2 Hz, 2H), 7.24 (t, J=5.7 Hz, 1H), 4.27 (d, J=6.9 Hz, 2H), 4.19 (t, J=6.9 Hz, 1H), 3.86-3.78 (m, 1H), 2.95 (q, J=6.5 Hz, 2H), 2.04 (t, J=5.7 Hz, 2H), 1.64 (dt, J=14.1, 8.9 Hz, 8H), 1.40-1.32 (m, 2H), 1.12 (s, 2H). MS m/z 462 [M+H]$^+$.

Step 4: General procedure was followed to obtain (S)-8-(4-aminobenzyl)-6,9-diazaspiro[4.5]decane-7,10-dione as a off-white solid, Yield-98%, $^1$H NMR (400 MHz, Methanol-d$_4$) δ 6.97-6.89 (m, 2H), 6.72-6.62 (m, 2H), 4.20 (t, J=4.3 Hz, 1H), 3.11 (dd, J=13.9, 4.0 Hz, 1H), 2.83 (dd, J=13.9, 4.6 Hz, 1H), 2.27-2.12 (m, 1H), 1.75-1.61 (m, 2H), 1.61-1.50 (m, 3H), 1.42 (ddd, J=13.4, 8.6, 7.2 Hz, 1H), 0.80 (dt, J=13.3, 6.5 Hz, 1H). HRMS m/z calcd for C$_{15}$H$_{19}$N$_3$O$_2$ [M+H]$^+$: 273.1477, found: 273.148.

j. Preparation of (R)-6-(4-Aminobutyl)-3,3-Dimethylpiperazine-2,5-Dione

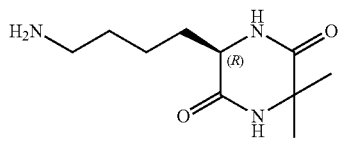

Step 1: General procedure was followed with (R)-6-((((9H-fluoren-9-yl)methoxy)carbonyl)amino)-2-((tert-butoxycarbonyl)amino)hexanoic acid and ethyl 2-amino-2-methylpropanoate, HCl to obtain (R)-ethyl 2-(6-((((9H-fluoren-9-yl)methoxy)carbonyl)amino)-2-((tert-butoxycarbonyl)amino)hexanamido)-2-methylpropanoate as a white solid, Yield-92%, $^1$H NMR (400 MHz, DMSO-d$_6$) δ 8.08 (s, 1H), 7.90-7.83 (m, 2H), 7.66 (d, J=7.6 Hz, 2H), 7.39 (tdd, J=7.5, 1.2, 0.6 Hz, 2H), 7.33-7.28 (m, 2H), 7.23 (t, J=5.7 Hz, 1H), 6.63 (d, J=8.4 Hz, 1H), 4.26 (d, J=6.9 Hz, 2H), 4.18 (t, J=6.9 Hz, 1H), 3.96 (q, J=7.1 Hz, 2H), 3.87 (s, 1H), 2.93 (s, 2H), 1.45 (s, 2H), 1.34 (s, 11H), 1.31 (s, 3H), 1.29 (s, 3H), 1.24 (s, 2H), 1.09 (t, J=7.1 Hz, 3H). MS m/z 582 [M+H]$^+$.

Step 2: General procedure was followed to obtain (R)-ethyl 2-(6-((((9H-fluoren-9-yl)methoxy)carbonyl)amino)-2-aminohexanamido)-2-methylpropanoate, TFA in Yield-49% (Over step 2 and 3)$^1$H NMR (400 MHz, Chloroform-d) δ 7.76 (dt, J=7.6, 0.9 Hz, 2H), 7.54 (dq, J=7.5, 0.9 Hz, 3H), 7.44-7.36 (m, 2H), 7.35-7.23 (m, 2H), 6.3 (s, 1H), 5.27 (s, 1H), 4.7-4.48 (bS, 1H), 4.41 (s, 1H), 4.22-4.13 (m, 3H), 3.16 (s, 1H), 3.11-302 (m, 1H), 1.87 (s, 2H), 1.56-1.53 (m, 1H), 1.5 (s, 3H), 1.48 (s, 3H), 1.41 (s, 3H), 1.24 (t, J=7.1 Hz, 3H). MS m/z 482 [M+H]$^+$.

Step 3: General procedure was followed to obtain (R)-(9H-fluoren-9-yl)methyl (4-(5,5-dimethyl-3,6-dioxopiperazin-2-yl)butyl)carbamate as a white solid, 1H NMR (400 MHz, DMSO-d6) δ 8.19 (s, 1H), 7.97 (s, 1H), 7.87 (dd, J=7.4, 1.0 Hz, 2H), 7.66 (d, J=7.4 Hz, 2H), 7.43-7.35 (m, 2H), 7.31 (td, J=7.5, 1.2 Hz, 2H), 7.26 (t, J=5.7 Hz, 1H), 4.27 (d, J=7.4 Hz, 2H), 4.18 (t, J=6.9 Hz, 1H), 3.91-3.83 (m, 1H), 2.94 (q, J=6.5 Hz, 2H), 1.65 (tt, J=14.0, 7.3 Hz, 2H), 1.44-1.31 (m, 1H), 1.28 (d, J=2.2 Hz, 8H), 1.20 (d, J=20.7 Hz, 1H). MS m/z 436 [M+H]$^+$.

Step 4: General procedure was followed to obtain (R)-6-(4-aminobutyl)-3,3-dimethylpiperazine-2,5-dione as a white solid, Yield-49%, $^1$H NMR (400 MHz, Deuterium Oxide) δ 4.17-4.08 (m, 1H), 2.79 (dd, J=8.5, 6.6 Hz, 2H), 1.87-1.77 (m, 1H), 1.76-1.66 (m, 1H), 1.53 (qd, J=8.1, 6.7 Hz, 2H), 1.37 (d, J=1.9 Hz, 7H), 1.31-1.18 (m, 1H). HRMS m/z calcd for C$_{10}$H$_{19}$N$_3$O$_2$ [M+H]$^+$: 213.1477, found: 213.1477.

k. Preparation of (S)-4-((5,5-Dimethyl-3,6-Dioxopiperazin-2-yl)Methyl)Benzamide

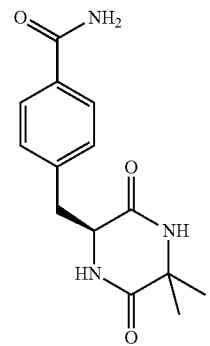 [SMILES: CC1(C)NC(=O)[C@H](Cc2ccc(C(N)=O)cc2)NC1=O]

Step 1: General procedure was followed with (S)-2-((tert-butoxycarbonyl)amino)-3-(4-carbamoylphenyl)propanoic acid and methyl 2-amino-2-methylpropanoate, HCl to obtain (S)-methyl 2-(2-((tert-butoxycarbonyl)amino)-3-(4-carbamoylphenyl)propanamido)-2-methylpropanoate as a white solid, Yield-73%, 1H NMR (400 MHz, Methanol-d4) δ 7.80 (d, J=7.9 Hz, 2H), 7.35 (d, J=7.9 Hz, 2H), 4.31 (dd, J=8.7, 6.0 Hz, 1H), 3.66 (s, 3H), 3.18-3.01 (m, 1H), 2.86 (dd, J=13.9, 8.7 Hz, 1H), 1.43 (s, 3H), 1.39 (s, 3H), 1.36 (s, 9H). MS m z 430 [M+Na]$^+$.

Step 2: General procedure was followed to obtain (S)-methyl 2-(2-amino-3-(4-carbamoylphenyl)propanamido)-2-methylpropanoate as a sticky solid, 1H NMR (400 MHz, Methanol-d4) δ 7.92-7.84 (m, 2H), 7.46-7.38 (m, 2H), 4.07 (dd, J=7.8, 6.7 Hz, 1H), 3.70 (s, 3H), 3.26 (dd, J=7.8, 6.2 Hz, 1H), 3.09 (dd, J=14.1, 7.8 Hz, 1H), 1.52-1.32 (m, 6H). MS m/z 308 [M+H]$^+$.

Step 3: General procedure was followed to obtain (S)-4-((5,5-dimethyl-3,6-dioxopiperazin-2-yl)methyl)benzamide as a white solid, Yield-32.8%, 1H NMR (400 MHz, DMSO-d6) δ 8.12 (s, 1H), 8.07 (d, J=1.9 Hz, 1H), 7.91 (s, 1H), 7.80-7.74 (m, 2H), 7.29 (s, 1H), 7.21 (d, J=8.3 Hz, 2H), 4.24 (ddd, J=5.3, 3.6, 1.8 Hz, 1H), 3.17 (dd, J=13.2, 3.7 Hz, 1H), 2.89 (dd, J=13.3, 5.0 Hz, 1H), 1.16 (s, 3H), 0.51 (s, 3H). HRMS m/z calcd for $C_{14}H_{17}N_3O_3$ [M+H]$^+$: 275.1270, found: 275.1272. HPLC-95.45% at $t_R$-1.87 min at 254 nm.

l. Preparation of (S)-4-((3,6-Dioxopiperazin-2-yl)Methyl)Benzamide

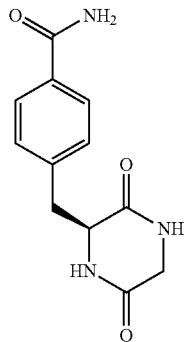 [SMILES: NC(=O)c1ccc(C[C@@H]2NC(=O)CNC2=O)cc1]

Step 1: General procedure was followed with (S)-2-((tert-butoxycarbonyl)amino)-3-(4-carbamoylphenyl)propanoic acid and ethyl 2-aminoacetate, HCl to obtain (S)-ethyl 2-(2-((tert-butoxycarbonyl)amino)-3-(4-carbamoylphenyl)propanamido)acetate as a white solid, Yield-73%, 1H NMR (400 MHz, Methanol-d4) δ 7.90-7.69 (m, 2H), 7.36 (d, J=8.3 Hz, 2H), 4.39 (dd, J=9.6, 5.0 Hz, 1H), 4.18 (q, J=7.1 Hz, 2H), 3.93 (d, J=6.9 Hz, 2H), 3.28-3.13 (m, 1H), 2.88 (dd, J=13.9, 9.6 Hz, 1H), 1.38-1.29 (m, 9H), 1.26 (t, J=7.1 Hz, 3H). MS m/z 294 [(M−100) for Boc+H]$^+$.

Step 2: General procedure was followed to obtain (S)-ethyl 2-(2-amino-3-(4-carbamoylphenyl)propanamido)acetate as a sticky solid, 1H NMR (400 MHz, DMSO-d6) δ 8.95 (t, J=5.8 Hz, 1H), 8.16 (d, J=5.6 Hz, 2H), 8.09 (s, 1H), 7.95 (s, 1H), 7.87-7.79 (m, 2H), 7.37-7.30 (m, 2H), 4.10 (q, J=7.1 Hz, 2H), 4.04-3.89 (m, 2H), 3.67 (d, J=5.6 Hz, 1H), 3.15 (dd, J=14.1, 5.3 Hz, 1H), 2.99 (dd, J=14.1, 8.0 Hz, 1H), 1.33-1.06 (m, 3H). MS m/z 294 [M+H]$^+$.

Step 3: General procedure was followed to obtain (S)-4-((3,6-dioxopiperazin-2-yl)methyl)benzamide as a white solid, Yield-33.9%, 1H NMR (400 MHz, DMSO-d6) δ 8.18 (d, J=2.6 Hz, 1H), 7.92 (s, 2H), 7.83-7.60 (m, 1H), 7.32 (s, 1H), 7.27-7.15 (m, 2H), 4.09 (d, J=2.8 Hz, 1H), 3.48-3.35 (m, 1H), 3.12 (dd, J=13.4, 4.6 Hz, 1H), 2.99-2.79 (m, 2H). HRMS m/z calcd for $C_{12}H_{13}N_3O_3$ [M+H]$^+$: 247.0957, found: 247.0961.

m. Preparation of (S)-4-((7,10-Dioxo-6,9-Diazaspiro[4.5]Decan-8-yl)Methyl)Benzamide

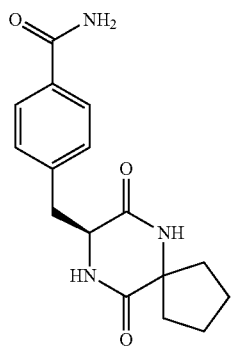 [SMILES: NC(=O)c1ccc(C[C@@H]2NC(=O)C3(CCCC3)NC2=O)cc1]

Step 1: General procedure was followed with (S)-2-((tert-butoxycarbonyl)amino)-3-(4-carbamoylphenyl)propanoic acid and methyl 1-aminocyclopentanecarboxylate to obtain (S)-methyl 1-(2-((tert-butoxycarbonyl)amino)-3-(4-carbamoylphenyl)propanamido)cyclopentanecarboxylate as a white solid, Yield-68.6%, 1H NMR (400 MHz, Methanol-d4) δ 7.81 (d, J=8.0 Hz, 2H), 7.36 (d, J=8.1 Hz, 2H), 4.33 (dd, J=8.6, 6.3 Hz, 1H), 3.64 (s, 3H), 3.09 (dd, J=13.7, 6.2 Hz, 1H), 2.88 (dd, J=13.8, 8.6 Hz, 1H), 2.15 (s, 1H), 2.13 (s, 1H), 1.97-1.88 (m, 1H), 1.86 (dd, J=13.3, 8.6 Hz, 1H), 1.73-1.56 (m, 4H), 1.37 (s, 9H). MS m/z 456 [M+Na]$^+$.

Step 2: General procedure was followed to obtain (S)-methyl 1-(2-amino-3-(4-carbamoylphenyl)propanamido)cyclopentanecarboxylate as a sticky solid, 1H NMR (400 MHz, DMSO-d6) δ 8.79 (s, 1H), 8.17 (d, J=5.4 Hz, 2H), 7.95 (s, 1H), 7.84 (d, J=8.2 Hz, 2H), 7.37-7.29 (m, 2H), 4.01 (q, J=6.3 Hz, 2H), 3.56 (s, 3H), 3.10 (dd, J=13.9, 6.2 Hz, 1H), 2.99 (dd, J=14.0, 7.6 Hz, 1H), 2.12-1.94 (m, 2H), 1.84 (ddd, J=12.6, 7.4, 4.3 Hz, 1H), 1.73 (ddd, J=12.4, 8.2, 4.2 Hz, 1H), 1.67-1.42 (m, 4H). MS m/z 334 [M+H]$^+$.

Step 3: General procedure was followed to obtain (S)-4-((7,10-dioxo-6,9-diazaspiro[4.5]decan-8-yl)methyl)benzamide as a white solid, Yield-34.7%, $^1$H NMR (400 MHz, DMSO-d$_6$) δ 8.24 (s, 1H), 8.06 (d, J=2.0 Hz, 1H), 7.91 (s, 1H), 7.79-7.72 (m, 2H), 7.28 (s, 1H), 7.24-7.17 (m, 2H), 4.26-4.14 (m, 1H), 3.14 (dd, J=13.2, 4.2 Hz, 1H), 2.93-2.84 (m, 1H), 2.03-1.91 (m, 1H), 1.66-1.55 (m, 1H), 1.53-1.45 (m, 3H), 1.34 (ddt, J=20.7, 15.1, 6.4 Hz, 2H), 0.78-0.66 (m, 1H). HRMS m/z calcd for $C_{16}H_{19}N_3O_3$ [M+H]$^+$: 301.1426, found: 301.1422; HPLC-96.47% at $t_R$-9.87 min at 240 nm.

n. Preparation of (S)-8-(3-Aminopropyl)-6,9-Diazaspiro[4.5]Decane-7,10-Dione

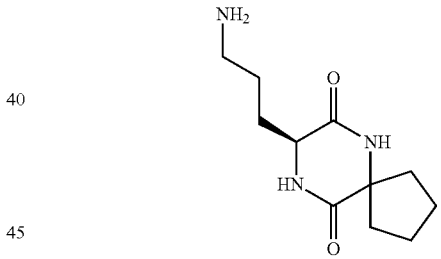

Step 1: General procedure was followed with (S)-5-((((9H-fluoren-9-yl)methoxy)carbonyl)amino)-2-((tert-butoxycarbonyl)amino)pentanoic acid and methyl 1-aminocyclopentanecarboxylate to obtain (S)-methyl 1-(5-((((9H-fluoren-9-yl)methoxy)carbonyl)amino)-2-((tert-butoxycarbonyl)amino)pentanamido)cyclopentanecarboxylate as a off-white solid, Yield-74.6%, $^1$H NMR (400 MHz, Methanol-d$_4$) δ 7.79 (d, J=7.5 Hz, 2H), 7.76-7.60 (m, 2H), 7.38 (tt, J=7.5, 1.0 Hz, 2H), 7.34-7.28 (m, 2H), 4.34 (dd, J=6.9, 1.5 Hz, 2H), 4.20 (t, J=6.9 Hz, 1H), 4.02 (d, J=7.9 Hz, 1H), 3.62 (s, 3H), 3.12 (hept, J=7.1 Hz, 2H), 2.24-2.07 (m, 2H), 1.94 (dt, J=12.7, 6.2 Hz, 2H), 1.73 (p, J=4.1 Hz, 5H), 1.61-1.45 (m, 3H), 1.43 (s, 9H). MS m/z 580 [M+H]$^+$.

Step 2: General procedure was followed to obtain (S)-methyl 1-(5-((((9H-fluoren-9-yl)methoxy)carbonyl)amino)-2-aminopentanamido)cyclopentanecarboxylate as a fluffy solid, Yield-65% (over step 2 and 3), 1H NMR (400 MHz, Chloroform-d) δ 7.85 (s, 1H), 7.79-7.71 (m, 2H), 7.53 (d, J=7.5 Hz, 2H), 7.39 (t, J=7.5 Hz, 2H), 7.29 (tdd, J=7.5, 2.1, 1.2 Hz, 2H), 4.39 (t, J=8.7 Hz, 1H), 4.30 (t, J=8.8 Hz, 1H), 4.23-4.08 (m, 2H), 3.63 (s, 3H), 3.36-3.09 (m, 1H), 2.26-1.98 (m, 2H), 1.89 (s, 4H), 1.69 (s, 6H). MS m/z 480 [M+H]$^+$.

Step 3: General procedure was followed to obtain (S)-(9H-fluoren-9-yl)methyl (3-(7,10-dioxo-6,9-diazaspiro[4.5]decan-8-yl)propyl)carbamate, $^1$H NMR (400 MHz, DMSO-d$_6$) δ 8.32 (s, 1H), 8.06-8.01 (m, 1H), 7.87 (d, J=7.5 Hz, 2H), 7.66 (d, J=7.5 Hz, 2H), 7.46-7.36 (m, 2H), 7.31 (td, J=7.5, 2.5 Hz, 3H), 4.26 (d, J=6.8 Hz, 2H), 4.19 (t, J=6.9 Hz, 1H), 3.87-3.80 (m, 1H), 2.96 (q, J=6.7 Hz, 2H), 2.18-1.91 (m, 2H), 1.70 (d, J=7.5 Hz, 2H), 1.68-1.55 (m, 6H), 1.45 (dq, J=15.5, 7.8, 7.1 Hz, 2H). MS m/z 448 [M+H]$^+$.

Step 4: General procedure was followed to obtain (S)-8-(3-aminopropyl)-6,9-diazaspiro[4.5]decane-7,10-dione as a white solid, Yield-63.6%, $^1$H NMR (400 MHz, DMSO-d$_6$) δ 8.30 (d, J=5.5 Hz, 1H), 8.09 (d, J=30.9 Hz, 2H), 6.67 (s, 1H), 3.82 (dd, J=7.0, 3.6 Hz, 1H), 2.89 (q, J=6.7 Hz, 1H), 2.52 (m, 1H), 2.15-1.95 (m, 2H), 1.77-1.72 (m, 1H), 1.72-1.69 (m, 1H), 1.68 (s, 1H), 1.66 (dd, J=4.2, 2.4 Hz, 1H), 1.64 (d, J=3.7 Hz, 1H), 1.63-1.61 (m, 1H), 1.61-1.59 (m, 1H), 1.59-1.55 (m, 1H), 1.38 (dt, J=15.8, 6.5 Hz, 2H). HRMS m/z calcd for C$_{11}$H$_{19}$N$_3$O$_2$ [M+H]$^+$: 225.1477, found: 225.1478.

o. Preparation of (S)-3-(4-Aminobenzyl)-1,4-Diazaspiro[5.5]Undecane-2,5-Dione

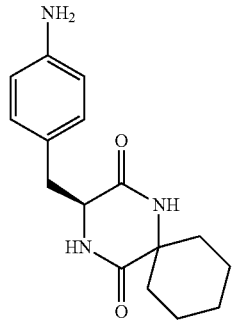 [SMILES: Nc1ccc(C[C@@H]2NC(=O)C3(CCCCC3)NC2=O)cc1]

Step 1: General procedure was followed with (S)-3-(4-((((9H-fluoren-9-yl)methoxy)carbonyl)amino)phenyl)-2-((tert-butoxycarbonyl)amino)propanoic acid and methyl 1-aminocyclohexanecarboxylate to obtain (S)-methyl 1-(3-(4-((((9H-fluoren-9-yl)methoxy)carbonyl)amino)phenyl)-2-((tert-butoxycarbonyl)amino)propanamido)cyclohexanecarboxylate as a pale-yellow solid, Yield-86%, $^1$H NMR (400 MHz, DMSO-d$_6$) δ 9.61 (s, 1H), 7.96-7.89 (m, 2H), 7.89-7.84 (m, 2H), 7.73 (d, J=7.4 Hz, 2H), 7.41 (tt, J=7.4, 0.9 Hz, 2H), 7.33 (td, J=7.5, 1.2 Hz, 3H), 7.14 (d, J=8.0 Hz, 2H), 6.79 (d, J=8.8 Hz, 1H), 4.44 (d, J=6.7 Hz, 2H), 4.28 (t, J=6.6 Hz, 1H), 4.15 (td, J=9.2, 4.7 Hz, 1H), 2.87 (s, 3H), 2.85-2.76 (m, 1H), 2.65-2.60 (m, 1H), 1.91 (d, J=12.1 Hz, 2H), 1.62 (d, J=12.2 Hz, 2H), 1.46 (s, 4H), 1.29 (s, 11H). MS m/z 664 [M+Na]$^+$ Step 2: General procedure was followed to obtain (S)-methyl 1-(3-(4-((((9H-fluoren-9-yl)methoxy)carbonyl)amino)phenyl)-2-aminopropanamido)cyclohexanecarboxylate in Yield-15% (over step 2 and 3), $^1$H NMR (400 MHz, DMSO-d$_6$) δ 9.69 (s, 1H), 8.44 (s, 1H), 8.07 (d, J=5.1 Hz, 2H), 7.95-7.86 (m, 3H), 7.72 (dd, J=7.5, 1.0 Hz, 2H), 7.41 (tt, J=7.4, 0.9 Hz, 3H), 7.33 (td, J=7.5, 1.2 Hz, 2H), 7.18 (d, J=8.2 Hz, 2H), 4.47 (d, J=6.7 Hz, 2H), 4.29 (t, J=6.6 Hz, 1H), 4.03 (d, J=10.3 Hz, 1H), 3.56 (s, 3H), 3.03 (dd, J=14.1, 5.9 Hz, 1H), 2.86-2.79 (m, 1H), 1.91 (dd, J=14.4, 4.6 Hz, 1H), 1.83 (d, J=13.7 Hz, 1H), 1.75-1.58 (m, 2H), 1.43 (d, J=15.5 Hz, 4H), 1.23 (s, 2H). MS m/z 542 [M+H]$^+$.

Step 3: (S)-(9H-fluoren-9-yl)methyl(4-((2,5-dioxo-1,4-diazaspiro[5.5]undecan-3-yl)methyl)phenyl)carbamate, $^1$H NMR (400 MHz, DMSO-d$_6$) δ 9.59 (s, 1H), 8.05 (s, 1H), 7.96-7.83 (m, 3H), 7.72 (d, J=7.5 Hz, 2H), 7.44-7.37 (m, 2H), 7.32 (td, J=7.4, 1.2 Hz, 4H), 7.04 (d, J=8.2 Hz, 2H), 4.44 (d, J=6.7 Hz, 2H), 4.27 (t, J=6.7 Hz, 1H), 4.14 (s, 1H), 3.05 (dd, J=13.5, 3.9 Hz, 1H), 2.79 (dd, J=13.7, 4.8 Hz, 1H), 1.74-1.63 (m, 1H), 1.52 (dd, J=23.4, 13.2 Hz, 1H), 1.47-1.38 (m, 2H), 1.35 (d, J=11.6 Hz, 2H), 1.29-1.18 (m, 2H), 1.10 (t, J=11.9 Hz, 1H), 0.43 (d, J=12.5 Hz, 1H). MS m/z 510 [M+H]$^+$.

Step 4: General procedure was followed to obtain (S)-3-(4-aminobenzyl)-1,4-diazaspiro[5.5]undecane-2,5-dione as a white solid, yield-60.8%, 1H NMR (400 MHz, Methanol-d4) δ 6.98-6.83 (m, 2H), 6.70-6.54 (m, 2H), 4.21 (t, J=4.2 Hz, 1H), 3.13 (dd, J=13.9, 4.0 Hz, 1H), 2.92-2.74 (m, 1H), 1.89 (td, J=14.1, 13.3, 4.2 Hz, 1H), 1.70-1.57 (m, 1H), 1.57-1.46 (m, 3H), 1.46-1.35 (m, 1H), 1.35-1.13 (m, 3H), 0.47-0.30 (m, 1H). HRMS m/z calcd for C$_{16}$H$_{21}$N$_3$O$_2$ [M+H]$^+$: 287.1634, found: 287.1641.

3. Screening Assays for Compound Activity

For initial screening, an ELISA-based screening assay was used in which purified human platelet TSP-1 was incubated with compounds and then incubated with recombinant latent TGF-β1 (purchased from R&D Systems). Activity is measured in a commercially available ELISA which detects only active TGF-β (R &D Systems). Activity in the presence of compounds is compared to activity in TSP-1+latent TGF-β samples without inhibitory compounds (Lu et al. (2016) *Am J Pathol* 186:678-690).

To specifically assess activity of compounds in liver cell specific assays, two different assays were used. In the first, human hepatic stellate cells were incubated overnight in low serum media to condition the media with secreted latent TGF-3. Purified TSP1 either preincubated with compounds or not will be added to cultures and then conditioned media harvested to assess TGF-β biological activity using the R&D Systems ELISA as above. Hepatic stellate cells will be purchased from commercial sources. Although hepatic stellate cells are the primary drivers of liver fibrosis, conditions which drive liver fibrosis can induce hepatocyte TSP-1 expression which can then have paracrine effects on controlling TGF-β activation in hepatic stellate cells. Furthermore, TGF-β can negatively impact hepatocyte regeneration following injury. Therefore, the ability of compounds to block TSP-1 activation of latent TGF-β will also be assessed in cultured primary human hepatocytes following the protocol described for the hepatic stellate cells. Similar approaches have successfully been used to screen compounds which inhibit human myeloma cell derived latent TGF-β activation by TSP-1 (Lu et al. (2016) *Am J Pathol* 186:678-690).

4. TSP1 and TGF-B Decrease Osteoblast Differentiation and TSP1 Inhibitory Peptide LSKL Increases Osteoblast Differentiation by MSCs Under Osteogenic Conditions Referring to FIG. 1A, MSCs were grown to confluence in basal (control) media. Cells were treated with control growth media, osteogenic media, or osteogenic media with TGF-β (5 ng/mL) or stripped TSP1 (10 nM), TSP1+LSKL (25 μM), TSP1+SLLK (25 μM control peptide), or TSP1+anti-TGF-β (5 μg/mL). Cultures were fed daily for 20 days. Alkaline phosphatase staining is representative of triplicate wells.

Figure 1B:
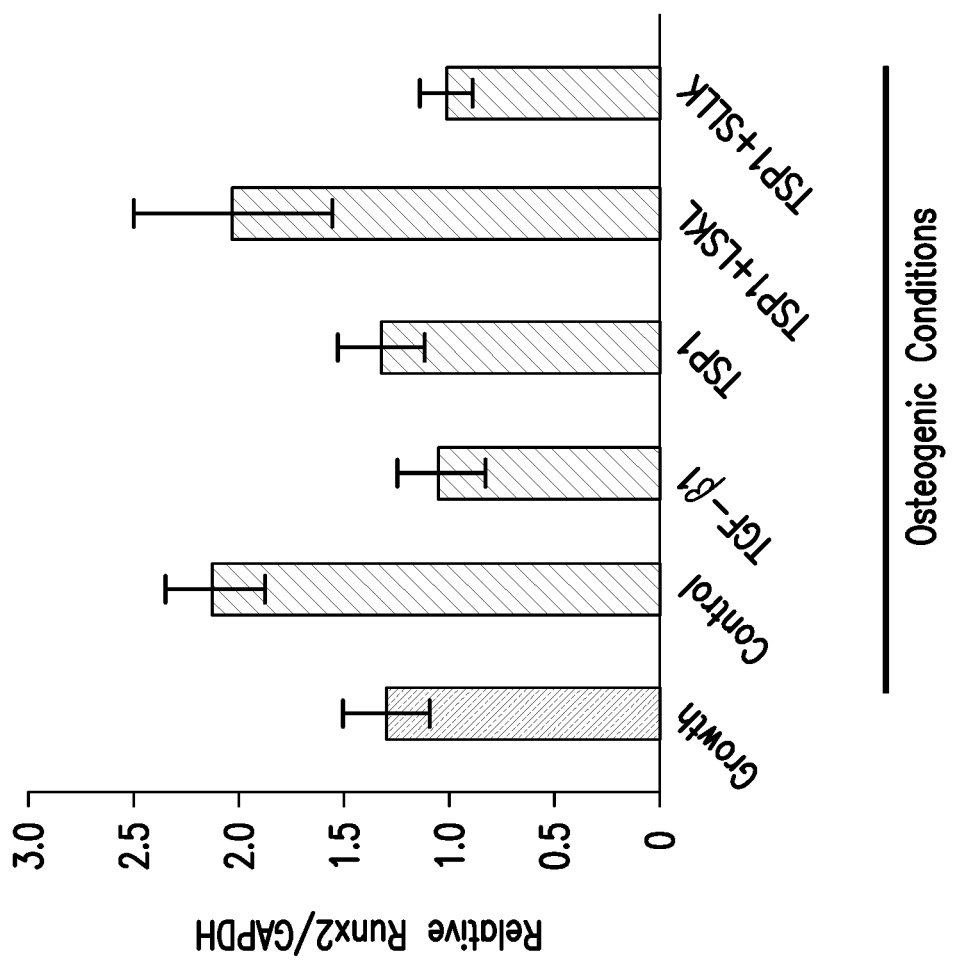

Referring to FIG. 1B, cells were treated every 2 days for 20 days with MSC growth media (control) or osteogenic media with TGF-β (5 ng/mL) or TSP1 (10 nM)±daily treatment with 25 μM LSKL or SLLK peptides. RNA isolated from cells was used for RT-PCR analysis of Runx2 expression. Samples were run in duplicate and each experimental treatment in triplicate.

5. LSKL Peptide Treatment Reduces MM Tumor Burden in the SCID-Tibia MM Model

Figures 2A, 2B:
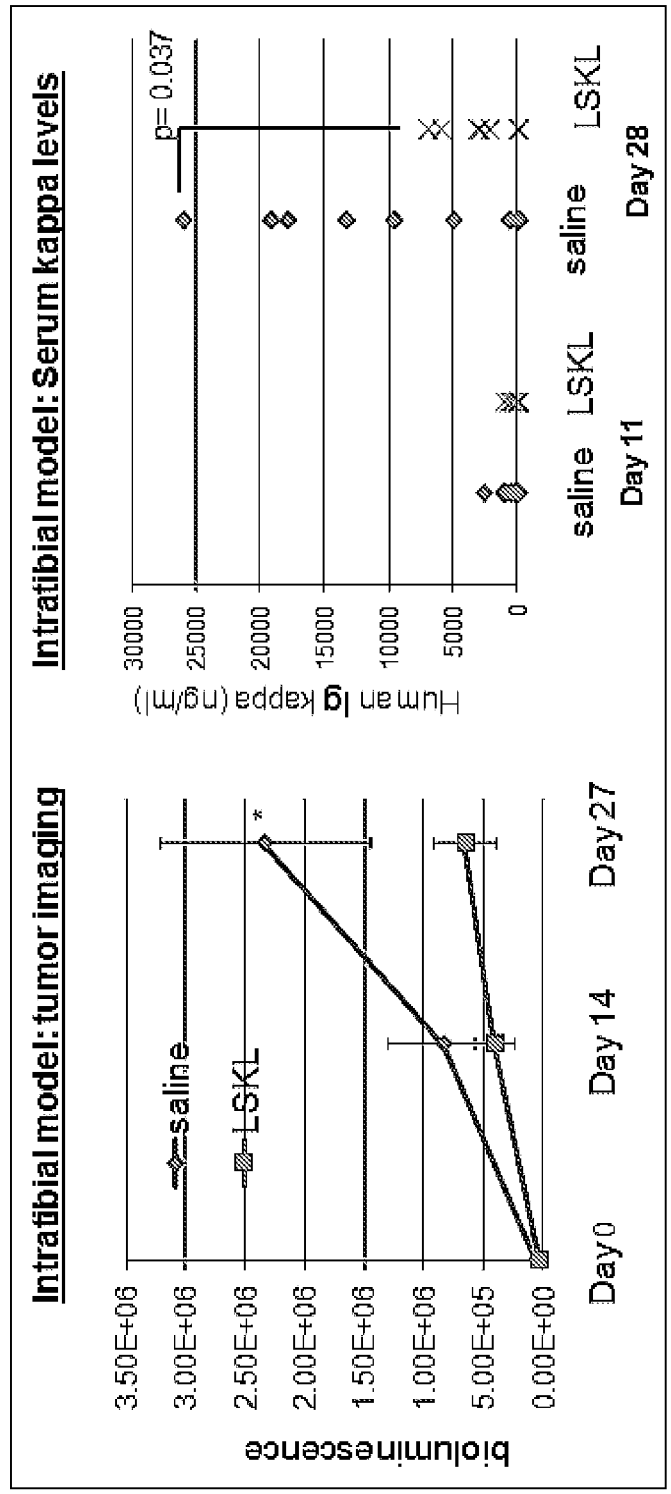
FIG. 2A and FIG. 2B show representative data illustrating the impact of LSKL treatment on tumor burden in the SCID-tibia MM model.

Referring to FIG. 2A and FIG. 2B, CAG human myeloma cells were injected into the intratibial marrow space of SCID mice. After 2 weeks, tumors were imaged by bioluminescence and serum 1 g kappa levels measured. Mice were randomized to equalize 1 g kappa levels. Osmotic pumps were implanted subcutaneously to deliver saline or LSKL peptide (30 mg/kg/day) (n=10/group). Tumors were imaged and serum 1 g kappa levels measured at 2 and 4 weeks of treatment. Data are means±SEM. Bioluminescence; *p=0.019 ANOVA, serum kappa; p=0.037, t-test.

6. LSKL Reduces Phospho-Smad 2 in the Bone Marrow

Figure 3A:
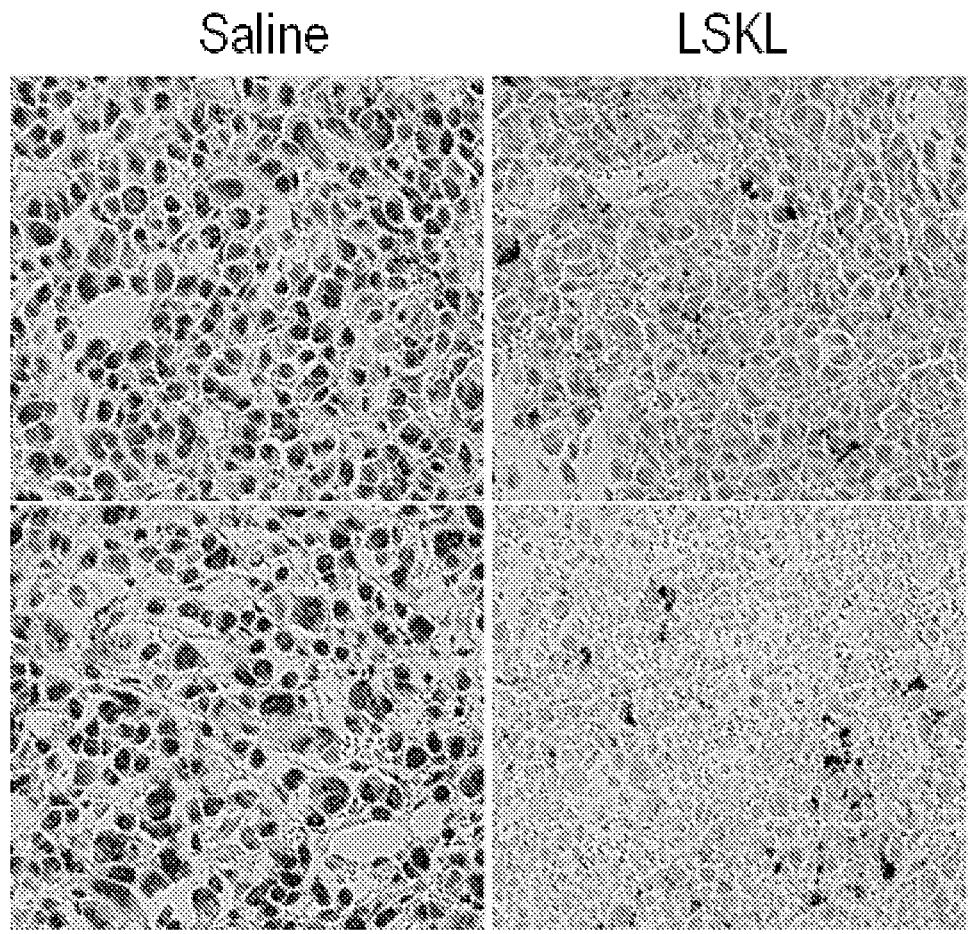
FIG. 3A-C show representative data illustrating the impact of LSKL treatment on Smad 2 phosphorylation in bone marrow myeloma cells.
Figures 3B, 3C:
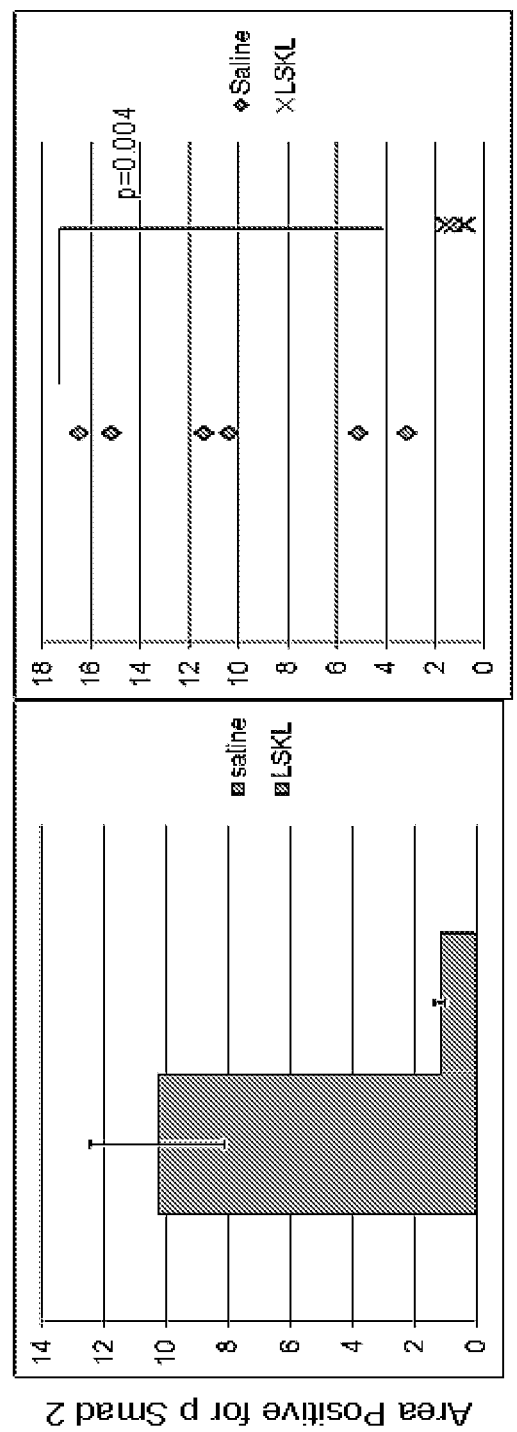

Referring to FIG. 3A-C, at 4 weeks of treatment, tibiae from mice injected with CAG MM cells were fixed and stained with antibody to phosphor-Smad 2. Left panels are from 2 different saline treated mice and the right panels are from LSKL-treated mice. Pixels of brown staining were quantified in 4 fields per animal. 5-6 animals per group were analyzed. Data are the percent area exceeding the threshold for positive staining (FIG. 3A). FIG. 3B represents the mean±SEM and FIG. 3C shows the data for individuals. P=0.004.

7. TSP1 Induces TGF-B Activity in Cag MM Cells and LSKL Reduces TGF-B Activity

Figure 4A:
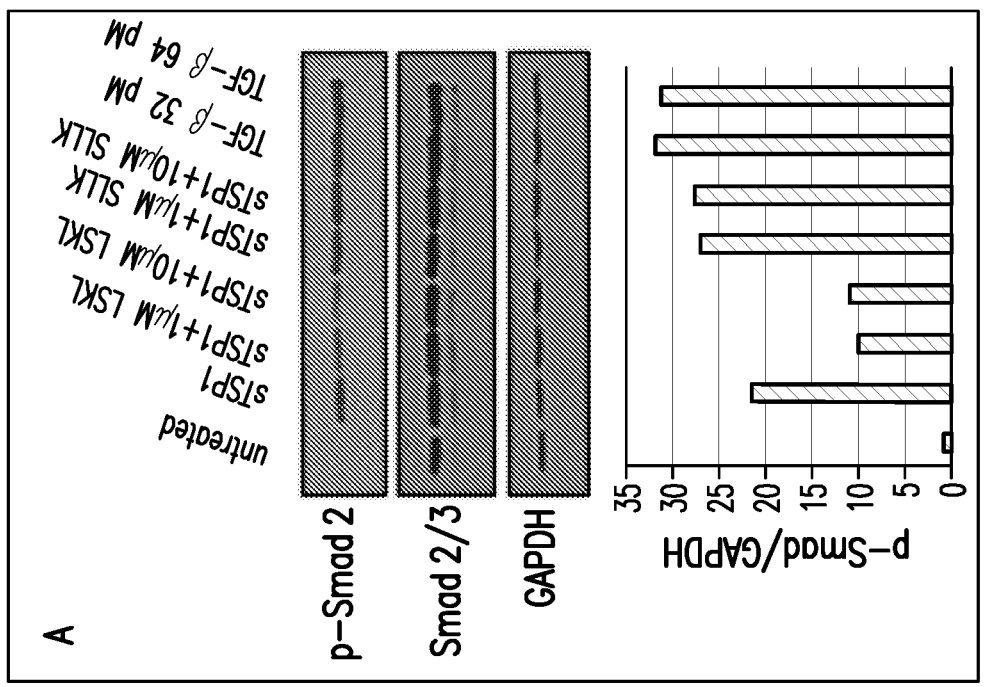
FIG. 4A and FIG. 4B show representative data illustrating the impact of TSP1 and LSKL on TGF-β activity in CAG MM cells.

Referring to FIG. 4A, CAG MM cells were incubated with 30 nM TSP1 for 6 hrs±LSKL or SLLK. Cell lysates were immunoblotted for phosphor-Smad 2. Blots were stripped and reprobed for total Smad 2/3 and GAPDH. Results are normalized to GAPDH (untreated controls=1). LSKL reduces TSP1 induced treatment or luciferase activity in cells treated with active TGF-β (not shown).

Figure 4B:
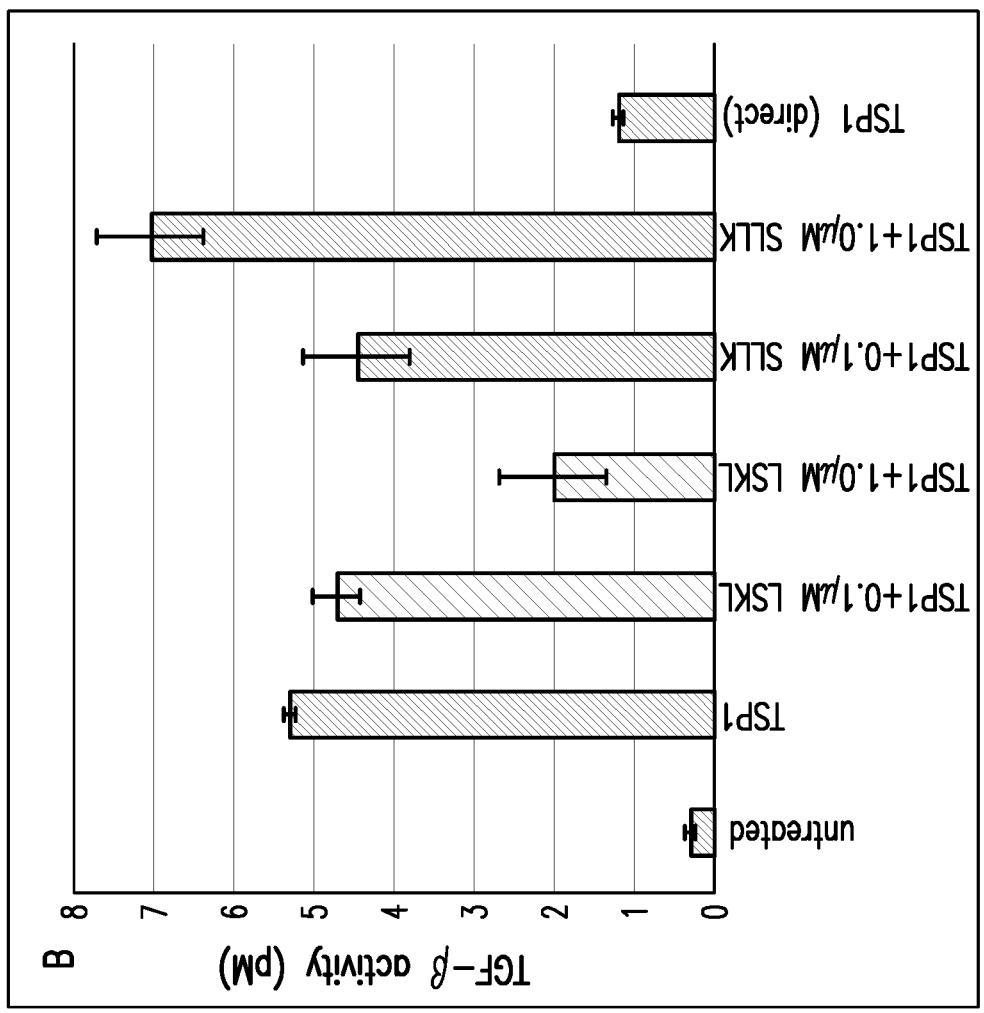
Figure 5:
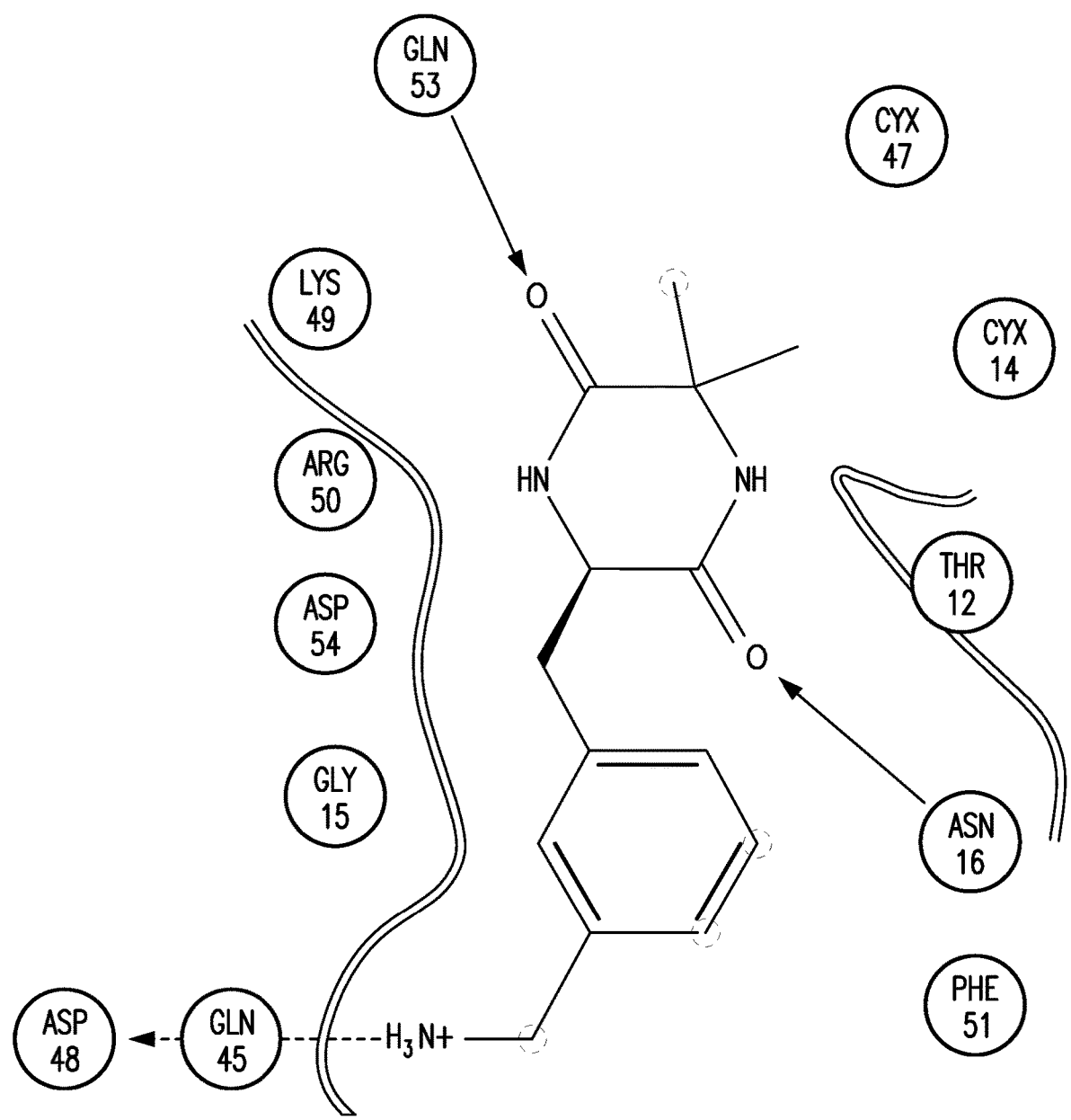
FIG. 5 shows a representative image of potentially significant interactions in the binding pocket.

Referring to FIG. 4B, CAG-heparanase MM cells were treated with 67 nM TSP1 and conditioned media were assessed for TGF-β activity using PAI-1 promoter luciferase reporter assay. There is ~1.19 μM TGF-β in the added TSP1 and LSKL blocks 80% of the CAG-heparanase MM cell generated TGF-β activity.

8. Evaluation of Inhibitory Activity Against TGF-B

Table 1 below illustrates the effects of the disclosed compounds on TGF-β mediated by TSP-1.

TABLE 1

| No. | Structure | Inhibition of TGF-β mediated by TSP-1 in vitro Elisa assay at [Inhibitor] | Inhibition of TGF-β mediated by TSP-1 cell-based assay at [Inhibitor] | $IC_{50}$ (nm) |
|---|---|---|---|---|
| 1 | [structure] | At 10 pM = −67%<br>At 50 pM = −4%<br>At 100 pM = 37% | At 10 nM = 38%<br>At 100 nM = 59%<br>At 1 μM = 74.5% | ND |
| 2 | [structure] | At 10 pM = 73%<br>At 50 pM = 91%<br>At 100 pM = 89% | At 10 nM = 38%<br>At 100 nM = 71%<br>At 1 μM = 76% | ND |
| 3 | [structure] | At 10 pM = 66%<br>At 50 pM = 68%<br>At 100 pM = 90% | At 10 nM = 13%<br>At 100 nM = 32%<br>At 1 μM = 75% | ND |
| 4 | [structure] | ND | At 10 nM = 80%<br>At 100 nM = 78%<br>At 1 μM = 83% | 1 |

TABLE 1-continued

| No. | Structure | Inhibition of TGF-β mediated by TSP-1 in vitro Elisa assay at [Inhibitor] | Inhibition of TGF-β mediated by TSP-1 cell-based assay at [Inhibitor] | IC$_{50}$ (nm) |
|---|---|---|---|---|
| 5 | (structure) | ND | At 10 nM = 45%<br>At 100 nM = 85%<br>At 1 μM = >100% | 2.4 |
| 6 | (structure) | ND | At 10 nM = 75%<br>At 100 nM = 96%<br>At 1 μM = 97% | 1 |
| 7 | (structure) | ND | At 10 nM = 72%<br>At 100 nM = 89%<br>At 1 μM = 92% | 0.85 |
| 8 | (structure) | ND | At 10 nM = 62%<br>At 100 nM = 89%<br>At 1 μM = 92% | 4 |
| 9 | (structure) | ND | At 10 nM = 40%<br>At 100 nM = 92%<br>At μM = >100% | 11 |
| 10 | (structure) | ND | Inactive | ND |
| 11 | (structure) | ND | At 10 nM = 25%<br>At 100 nM = 39%<br>At 1 μM = 40% | ND |

TABLE 1-continued

| No. | Structure | Inhibition of TGF-β mediated by TSP-1 in vitro Elisa assay at [Inhibitor] | Inhibition of TGF-β mediated by TSP-1 cell-based assay at [Inhibitor] | IC$_{50}$ (nm) |
|---|---|---|---|---|
| 12 | (structure) | ND | At 10 nM = 40%<br>At 100 nM = 65.6%<br>At 1 μM = 68% | ND |
| 13 | (structure) | ND | At 10 nM = 8%<br>At 100 nM = 24.6%<br>At 1 μM = 19.6% | ND |
| 14 | (structure) | ND | At 10 nM = 54%<br>At 100 nM = 85%<br>At 1 μM = 90% | ND |
| 15 | (structure) | ND | At 10 nM = 49%<br>At 100 nM = 85%<br>At 1 μM = 94% | ND |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

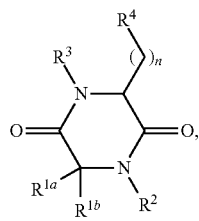

wherein n is selected from 1, 2, 3, and 4;
wherein each of $R^{1a}$ and $R^{1b}$ is independently C1-C4 alkyl;
or wherein each of $R^{1a}$ and $R^{1b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; and
wherein each of $R^2$ and $R^3$ is independently selected from hydrogen and C1-C4 alkyl; and
wherein $R^4$ is selected from —$NR^{20a}R^{20b}$ and $Cy^1$;
 wherein each of $R^{20a}$ and $R^{20b}$, when present, is independently selected from hydrogen, C1-C4 alkyl, C1-C4 haloalkyl, cycloalkyl, and heteroaryl;
 wherein $Cy^1$, when present, is selected from C5-C6 cycloalkyl, monocyclic heteroaryl, and —$C_6H_4R^{21}$ and is substituted with 0-4 non-hydrogen groups independently selected from halogen, —$NH_2$, C1-C4 alkyl, C1-C4 haloalkylh, C1-C4 hydroxyalkyl, C1-C4 alkoxy, C1-C4 alkylamino, and (C1-C4)(C1-C4) dialkylamino; and
  wherein $R^{21}$, when present, is selected from —$(CH_2)_qNR^{31a}R^{31b}$ and —$C(O)NR^{32a}R^{32b}$;
   wherein q, when present, is selected from 0 and 1;
   wherein each of $R^{31a}$, $R^{31b}$, $R^{32a}$, and $R^{32b}$, when present, is independently selected from hydrogen and C1-C4 alkyl;
or wherein each of $R^{1a}$ and $R^{1b}$ is hydrogen and $R^4$ is —$C_6H_4C(O)NR^{32a}R^{32b}$;
or wherein $R^{1a}$ is hydrogen, $R^{1b}$ is —$CH_2Cy^2$, and $R^4$ is —$C_6H_4R^{21}$;
 wherein $Cy^2$ is selected from C3-C6 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
provided that when n is 1 and each of $R^{1a}$ and $R^{1b}$ together comprise a 3-membered cycloalkyl then $Cy^1$, when present, is not monocyclic heteroaryl, and
provided that when $R^4$ is $NR^{20a}R^{20b}$ then each of $R^{1a}$ and $R^{1b}$ is independently C1-C4 alkyl,
or a pharmaceutically acceptable salt thereof.

2. The compound of claim 1, wherein n is 1.
3. The compound of claim 1, wherein each of $R^2$ and $R^3$ is hydrogen.
4. The compound of claim 1, wherein $R^4$ is $NHR^{20a}$.
5. The compound of claim 1, wherein each of $R^{20a}$ and $R^{20b}$ is hydrogen.
6. The compound of claim 1, wherein $R^4$ is $Cy^1$.

7. The compound of claim 1, having a structure represented by a formula:

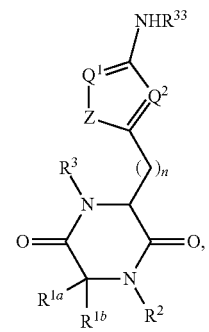

wherein Z is selected from O, S, and $NR^{40}$;
 wherein $R^{40}$, when present, is selected from hydrogen and C1-C4 alkyl;
wherein each of $Q^1$ and $Q^2$ is independently selected from CH and N; and
wherein $R^{33}$ is selected from hydrogen and C1-C4 alkyl.

8. The compound of claim 1, having a structure represented by a formula:

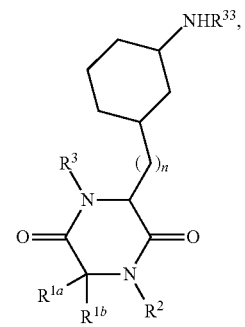

wherein $R^{33}$ is selected from hydrogen and C1-C4 alkyl.

9. The compound of claim 1, having a structure represented by a formula:

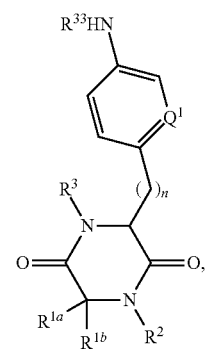

wherein $Q^1$ is selected from CH and N; and
wherein $R^{33}$ is selected from hydrogen and C1-C4 alkyl.

10. The compound of claim 1, having a structure selected from:
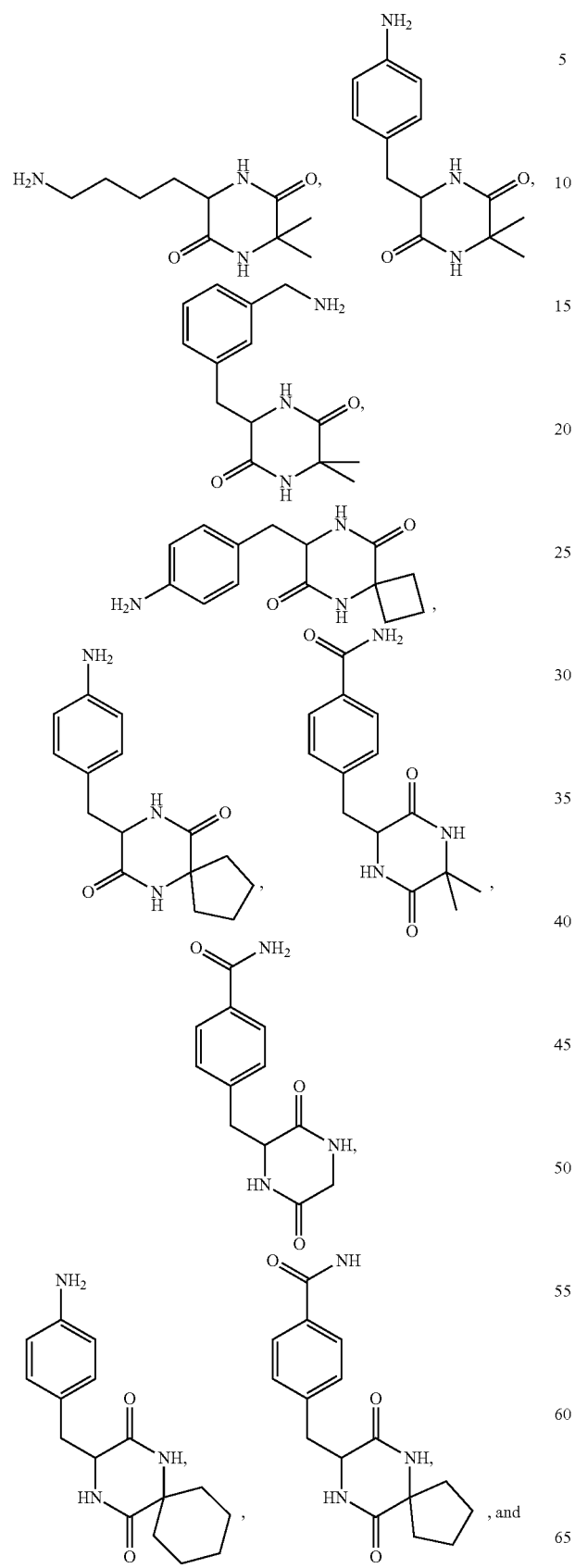
11. The compound of claim 1, having a structure selected from:
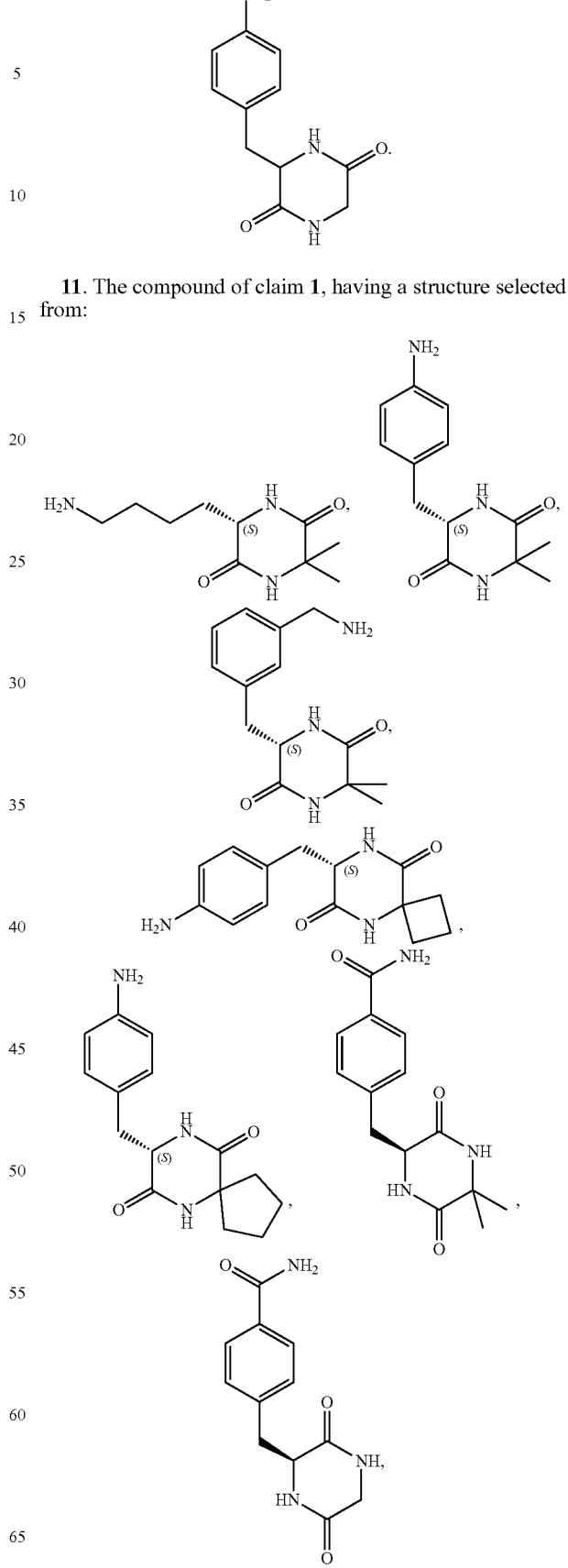

-continued
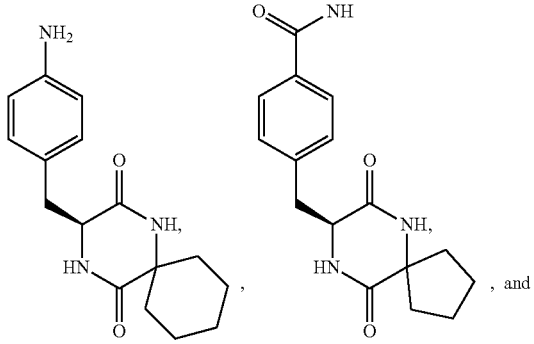
, and
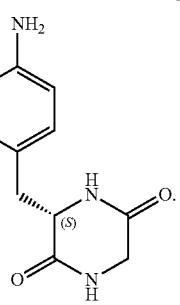
.
12. A pharmaceutical composition comprising a therapeutically effective amount of at least one compound of claim 1 and a pharmaceutically acceptable carrier.
* * * * *